US011124769B2

(12) United States Patent
Murphy et al.

(10) Patent No.: US 11,124,769 B2
(45) Date of Patent: Sep. 21, 2021

(54) PRODUCTION OF RED BLOOD CELLS AND PLATELETS FROM STEM CELLS

(71) Applicants: BOSTON MEDICAL CENTER CORPORATION, Boston, MA (US); TRUSTEES OF BOSTON UNIVERSITY, Boston, MA (US)

(72) Inventors: George J. Murphy, Boston, MA (US); David H. Sherr, West Roxbury, MA (US); Sarah S. Rozelle, Jamaica Plain, MA (US); Brenden W. Smith, Warwick, RI (US)

(73) Assignees: BOSTON MEDICAL CENTER CORPORATION, Boston, MA (US); TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/898,526

(22) Filed: Feb. 17, 2018

(65) Prior Publication Data

US 2018/0291344 A1 Oct. 11, 2018

Related U.S. Application Data

(60) Division of application No. 14/421,191, filed as application No. PCT/US2013/055160 on Aug. 15, 2013, now Pat. No. 9,896,660, which is a continuation-in-part of application No. 13/828,357, filed on Mar. 14, 2013, now Pat. No. 9,074,186.

(60) Provisional application No. 61/683,246, filed on Aug. 15, 2012.

(51) Int. Cl.
| | |
|---|---|
| *A61K 35/19* | (2015.01) |
| *A61K 31/404* | (2006.01) |
| *C12N 5/0789* | (2010.01) |
| *C12N 5/078* | (2010.01) |
| *A61K 35/18* | (2015.01) |
| *G01N 33/50* | (2006.01) |
| *A61K 45/06* | (2006.01) |
| *A61K 31/655* | (2006.01) |
| *G01N 33/80* | (2006.01) |
| *G01N 33/86* | (2006.01) |
| *A61K 35/12* | (2015.01) |

(52) U.S. Cl.
CPC .......... *C12N 5/0647* (2013.01); *A61K 31/404* (2013.01); *A61K 31/655* (2013.01); *A61K 35/18* (2013.01); *A61K 35/19* (2013.01); *A61K 45/06* (2013.01); *C12N 5/0641* (2013.01); *C12N 5/0644* (2013.01); *G01N 33/5044* (2013.01); *G01N 33/80* (2013.01); *G01N 33/86* (2013.01); *A61K 2035/124* (2013.01); *C12N 2501/60* (2013.01); *C12N 2501/998* (2013.01); *C12N 2501/999* (2013.01); *C12N 2506/03* (2013.01); *C12N 2506/45* (2013.01); *G01N 2500/10* (2013.01)

(58) Field of Classification Search
CPC .............................. C12N 5/0644; A61K 35/19
See application file for complete search history.

(56) References Cited

U.S. PATENT DOCUMENTS

| | | | |
|---|---|---|---|
| 9,074,186 B2 | 7/2015 | Murphy et al. | |
| 2010/0183564 A1 | 7/2010 | Boitano et al. | |
| 2015/0335680 A1 | 11/2015 | Murphy et al. | |
| 2015/0335682 A1 | 11/2015 | Murphy et al. | |

FOREIGN PATENT DOCUMENTS

| | | |
|---|---|---|
| WO | 99/10494 | 3/1999 |
| WO | 00/57891 | 10/2000 |
| WO | 2006/047569 A2 | 5/2006 |

(Continued)

OTHER PUBLICATIONS

Giammona et al. "Nicotinamide (vitamin B3) increases the polyploidisation proplatelet formation of cultured primary human megakaryocytes" (2006) British J of Haematology, vol. 135: 554-566. (Year: 2006).*

(Continued)

*Primary Examiner* — Teresa E Knight

(74) *Attorney, Agent, or Firm* — Arrigo, Lee, Guttman & Mouta-Bellum LLP

(57) ABSTRACT

This disclosure provides methods of making a megakaryocyte-erythroid progenitor cell (MEP), comprising differentiating a MEP precursor cell into a MEP in culture in the presence of an aryl hydrocarbon receptor (AhR) modulator. In some embodiments the AhR modulator is an AhR antagonist. In some embodiments the AhR modulator is an AhR agonist. In some embodiments the methods comprise culturing MEP precursor cells in the presence of an AHR antagonist and then culturing MEP precursor cells in the presence of an AHR agonist. In some embodiments the stem cell is a pluripotent stem cell. In some embodiments the MEP co-expresses CD41 and CD235. In some embodiments the number of MEPs produced in the culture increases exponentially. Methods of making a red blood cell (RBC) by culturing a MEP in the presence of an AhR modulator are also provided. Methods of making a megakaryocyte and/or a platelet, comprising culturing a MEP in the presence of an AhR modulator are also provided. In some embodiments the AhR modulator is an AhR antagonist. This disclosure also provides compositions comprising at least 1 million MEPs per ml and compositions in which at least 50% of the cells are MEPs, among other things.

4 Claims, 38 Drawing Sheets

(56) References Cited

FOREIGN PATENT DOCUMENTS

| WO | 2010/039997 A2 | 4/2010 |
| --- | --- | --- |
| WO | 2010/108005 A2 | 9/2010 |
| WO | 2011/115308 A1 | 9/2011 |
| WO | 2012/061146 A1 | 5/2012 |
| WO | 2014/028749 A2 | 2/2014 |

OTHER PUBLICATIONS

Diani-Moore et al. "Identification of the Aryl Hydrocarbon Receptor Target Gene TiPARP as a Mediator of Suppression of Hepatic Gluconeogenesis by 2,3,7,8-Tetrachlorodibenzo-p-dioxin and of Nicotinamide as a Corrective Agent for this Effect" (2010) J Biol Chem, vol. 285, No. 50: 38801-38810 (Year: 2010).*

Allan, L.L. and D.H. Sherr, Constitutive activation and environmental chemical induction of the aryl hydrocarbon receptor/transcription factor in activated human B lymphocytes. Mol Pharmacol, 2005. 67(5): p. 1740-50.

Apetoh, L., et al., The aryl hydrocarbon receptor interacts with c-Maf to promote the differentiation of type 1 regulatory T cells induced by IL-27. Nat Immunol, 2010. 11(9): p. 854-61.

Boitano, A.E., et al., Aryl hydrocarbon receptor antagonists promote the expansion of human hematopoietic stem cells. Science, 2010. 329(5997): p. 1345-8.

Chang, K.H., et al., Definitive-like erythroid cells derived from human embryonic stem cells coexpress high levels of embryonic and fetal globins with little or no adult globin. Blood, 2006. 108(5): p. 1515-23.

Funatake, C.J., et al., Cutting edge: activation of the aryl hydrocarbon receptor by 2,3,7,8-tetrachlorodibenzo-p-dioxin generates a population of CD4+ CD25+ cells with characteristics of regulatory T cells. J Immunol, 2005. 175(7): p. 4184-8.

Giarratana et al., Blood, vol. 118, pp. 5071-5079 (2011).

Greenberg, S. M., et al., Characterization of a New Megakaryocytic Cell Line: The Dami Cell. Blood, 1988. 72(6): p. 1968-1977.

Hirabayashi, Y. and T. Inoue, Aryl hydrocarbon receptor biology and xenobiotic responses in hematopoietic progenitor cells. Biochem Pharmacol, 2009. 77(4): p. 521-35.

Li, Y., et al., Exogenous Stimuli Maintain Intraepithelial Lymphocytes via Aryl Hydrocarbon Receptor Activation. Cell, 2011. 147(3): p. 629-40.

Lindsey, S. and E.T. Papoutsakis, The aryl hydrocarbon receptor (AHR) transcription factor regulates megakaryocytic polyploidization. Br J Haematol, 2011. 152(4): p. 469-84.

Lu, S.J., et al., CD34+CD38− hematopoietic precursors derived from human embryonic stem cells exhibit an embryonic gene expression pattern. Blood, 2004. 103(11): p. 4134-41.

Ma, F., et al., Generation of functional erythrocytes from human embryonic stem cell-derived definitive hematopoiesis. Proc Natl Acad Sci U S A, 2008. 105(35): p. 13087-92.

Martin, B., et al., Interleukin-17-Producing gammadelta T Cells Selectively Expand in Response to Pathogen Products and Environmental Signals. Immunity, 2009.

Pang et al., J Clin Invest, vol. 115, No. 12, pp. 3332-3338 (2005).

Qiu, C., et al., Globin switches in yolk sac-like primitive and fetal-like definitive red blood cells produced from human embryonic stem cells. Blood, 2008. 111(4): p. 2400-8.

Quintana, F.J., et al., An endogenous aryl hydrocarbon receptor ligand acts on dendritic cells and T cells to suppress experimental autoimmune encephalomyelitis. Proc Natl Acad Sci U S A, 2010.

Quintana, F.J., et al., Control of T(reg) and T(H)17 cell differentiation by the aryl hydrocarbon receptor. Nature, 2008. 453(7191): p. 65-71.

Response to Written Opinion of the International Searching Authority, Application No. PCT/US2013/055160, filed Jun. 13, 2014.

Search Report, Application No. PCT/US2013/055160, dated Mar. 7, 2014.

Singh, K.P., et al., Aryl hydrocarbon receptor-null allele mice have hematopoietic stem/progenitor cells with abnormal characteristics and functions. Stem Cells Dev, 2011. 20(5): p. 769-84.

Takayama, N., et al., Generation of functional platelets from human embryonic stem cells in vitro via ES-sacs, VEGF-promoted structures that concentrate hematopoietic progenitors. Blood, 2008. 111(11): p. 5298-306.

Thurmond, T.S., et al., The aryl hydrocarbon receptor has a role in the in vivo maturation of murine bone marrow B lymphocytes and their response to 2,3,7,8-tetrachlorodibenzo-p-dioxin. Toxicol Appl Pharmacol, 2000. 165(3): p. 227-36.

Veldhoen, M., et al., Natural agonists for aryl hydrocarbon receptor in culture medium are essential for optimal differentiation of Th17 T cells. J Exp Med, 2009. 206(1): p. 43-9.

Veldhoen, M., et al., The aryl hydrocarbon receptor links T(H)17-cell-mediated autoimmunity to environmental toxins. Nature, 2008.

Vodyanik, M. A., et al., Blood, vol. 108, No. 6, pp. 2095-2105 (2006).

Written Opinion, Application No. PCT/US2013/055160, dated Mar. 7, 2014.

International Preliminary Report on Patentability, Application No. PCT/US2013/055160, dated Jan. 29, 2015.

Chang, Chan-Jung, et al., "Production of Embryonic and Fetal-Like Red Blood Cells from Human Induced Pluripotent Stem Cells," PLoS One 6(10): e25761, doi:10.1371/journal.pone.0025761.

Ebihara, Yasuhiro, et al., "Generation of red blood cells from human embryonicfinduced pluripotent stem cells fro blood transfusion," Int. J. Hematol. (2012) 95:610-616.

Gaur, M., "Megakaryocytes derived from human embryonic stem cells: a genetically tractable system to study megakaryocytopoiesis and integrin function," (2006) Journal of Thrombosis and Haemostasis, 4: 436-442.

* cited by examiner

PRODUCTION OF RED BLOOD CELLS AND PLATELETS FROM STEM CELLS

CROSS-REFERENCE TO RELATED APPLICATIONS

This application is a divisional of application Ser. No. 14/421,191 (now U.S. Pat. No. 9,896,660). Application Ser. No. 14/421,191 is a national stage entry of PCT/US2013/055160, which claims priority to U.S. Provisional Application No. 61/683,246, filed Aug. 15, 2012, and to U.S. application Ser. No. 13/828,357, filed Mar. 14, 2013, both of which are hereby incorporated herein by reference.

GOVERNMENT FUNDING

This invention was made with Government Support under Contract Nos. HL107443, ES11624, and ES007381 awarded by the National Institutes of Health. The Government has certain rights in the invention.

INTRODUCTION

Blood transfusion is an indispensable cell therapy, and the safety and adequacy of the blood supply are national and international concerns. In 2009 alone, the National Blood Data Resource Center reported that blood-banking institutions collected more than 17 million units of whole blood and red cells with hospitals in the US transfusing over 15 million patients yearly. Due to substantial polymorphisms of blood group antigens, there are, even in developed countries, chronic shortages of blood for some patient groups. In the US, more than 40% of Sickle Cell Anemia patients, who are largely of African descent, experience immune reactions when transfused with blood from donors, who are mostly of Caucasian decent. Sporadic shortages of blood can also occur in association with natural or man-made disasters. There is also increasing concern that the blood supply may be curtailed by new restrictions on donor eligibility as new blood transmissible diseases are discovered and/or emerge and spread to new geographical locations. Lastly, blood usage by the growing numbers of individuals greater than 60 years of age is predicted to increase, leading to an insufficient blood supply by 2050.

For these and other reasons, there is a need in the art for new methods of making red blood cells and platelets. There is also a need for new methods of making myeloid-erythroid progenitor cells (MEPs), which for example enable production of red blood cells and/or platelets.

SUMMARY

The inventors have made novel observations regarding the roles of aryl hydrocarbon receptor (AhR) signaling in the differentiation of red blood cells (RBCs) and platelets, as well as cell types that are precursors of RBCs and platelets. The inventors have applied their findings to provide inventions in this disclosure in the fields of methods of making megakaryocyte-erythroid progenitor cells (MEPs), methods of making RBCs, methods of making megakaryocytes (Mks), and methods of making platelets. The inventors have also applied their findings to provide inventions in this disclosure in the fields of RBCs, Mks, platelets, MEPs, MEP precursor cells, and compositions comprising at least one of these cell types. The disclosure also provides methods of providing at least one of RBCs, Mks, and platelets to a subject and methods of screening a compound for an effect on at least one of RBCs, Mks, and platelets. Methods of increasing RBC count and methods of increasing platelet count by administering AhR modulators are also provided. These and other aspects of this disclosure are described more fully below.

This disclosure provides, among other things, new methods of making a megakaryocyte-erythroid progenitor cell (MEP). In some embodiments the methods comprising differentiating a MEP precursor cells into a MEP in culture in the presence of an aryl hydrocarbon receptor (AhR) modulator. In some embodiments the MEP precursor cell is a pluripotent stem cell. In some embodiments the methods comprise culturing MEP precursor cells in the presence of an AHR antagonist. In some embodiments the methods comprise culturing MEP precursor cells in the presence of an AHR agonist. In some embodiments the methods comprise culturing MEP precursor cells in the presence of an AHR antagonist and then culturing MEP precursor cells in the presence of an AHR agonist. In some embodiments of the methods the culture does not comprise serum. In some embodiments of the methods the culture does not comprise feeder cells.

In some embodiments the methods comprise differentiating a pluripotent stem cell into a MEP in culture in the presence of at least one protein selected from BMP-4, vVEGF, WNT3a, bFGF, hSCF, FLT3, TPO, and EPO. In some embodiments the methods comprise differentiating a pluripotent stem cell into a MEP in culture in the presence of BMP-4, vVEGF, WNT3a, bFGF, hSCF, FLT3, TPO, and EPO. In some embodiments the methods further comprise culturing MEP precursor cells in the presence of an aryl hydrocarbon receptor (AhR) modulator. In some embodiments the methods further comprise culturing MEP precursor cells in the presence of an aryl hydrocarbon receptor (AhR) antagonist. In some embodiments the methods further comprise culturing MEP precursor cells in the presence of an aryl hydrocarbon receptor (AhR) agonist. In some embodiments the methods further comprise culturing MEP precursor cells in the presence of an AHR antagonist and then culturing MEP precursor cells in the presence of an AHR agonist.

In some embodiments the methods comprise a) culturing the pluripotent stem cell in RPMI media supplemented with BMP-4, VEGF, Wnt3a, and knockout serum replacement (KOSR); b) culturing the cell obtained from step a) in RPMI media supplemented with BMP-4, VEGF, bFGF and KOSR; c) culturing the cell obtained from step b) in StemPro 34 media supplemented with BMP-4, VEGF, and bFGF; d) culturing the cell obtained from step c) in StemPro 34 media supplemented with VEGF, and bFGF; e) culturing the cell obtained from step d) in a mixture of IMDM and Hams F12 supplemented with B27, N2-supplement, BSA, VEGF, bFGF, hSCF, and Flt3 ligand; and f) culturing the cell obtained from step e) in a mixture of IMDM and Hams F12 supplemented with B27, N2-supplement, BSA, VEGF, bFGF, hSCF, Flt3 ligand, hTPO, IL-6, and EPO. In some embodiments the media in at least one of culture steps a) to e) further comprises an AhR antagonist. In some embodiments the culture media in step f) further comprises an AhR agonist.

In some embodiments of the methods the pluripotent stem cell is chosen from an embryonic stem (ES) cell, an induced pluripotent stem cell (iPSC), and a cell produced by nuclear transfer. In some embodiments the iPCS cell expresses OCT4, KLF4, SOX2, and cMYC. In some embodiments the MEP co-expresses CD41 and CD235. In some embodiments the MEP does not express CD34. In some embodiments the culture begins to make MEP cells within 10 days. In some embodiments the culture begins to make MEP cells within 7 days. In some embodiments the culture continues to produce new MEP cells for at least 30 days. In some embodiments the number of MEPs produced in the culture increases exponentially or substantially exponentially wherein "substantially exponentially" means at least 97% of the theoretical "exponential growth" over the relative time period. In some embodiments the number of MEPs produced in the culture increases exponentially over a culture period of 1 hour, 2 hours, 3, hours, 4 hours, 5 hours, 6 hours, 7, hours, 8 hours, 9 hours, 10 hours, 11 hours, 12 hours, 15 hours, 18 hours, 24 hours, 48 hours, 72 hours or 96 hours. In some embodiments the culture comprises at least 1 million MEPs per ml. In some embodiments the culture comprises at least 10 million MEPs per ml. In some embodiments at least 10% of the cells in the culture are MEPs. In some embodiments at least 50% of the cells in the culture are MEPs. In some embodiments the culture produces at least 10 million MEPs. In some embodiments the culture produces at least 100 million MEPs.

A MEP made by a method of this disclosure is also provided.

A cell culture comprising MEPs made by a method of this disclosure is also provided.

Methods of making a red blood cell (RBC) are also provided. In some embodiments the methods of making a RBC comprise making a MEP by a method of this disclosure, and culturing the MEP under conditions sufficient to make a RBC. In some embodiments the conditions sufficient to make a RBC comprise culturing the MEP in the presence of an AhR agonist. In some embodiments the conditions sufficient to make a RBC comprise culturing in erythroid specification media. In some embodiments the conditions sufficient to make a RBC further comprise culturing in erythroid specification media and culturing in the presence of an AhR agonist.

In some embodiments the methods of making a RBC comprise providing a MEP that was made by a method of this disclosure, and culturing the MEP under conditions sufficient to make a RBC. In some embodiments the conditions sufficient to make a RBC comprise culturing the MEP in the presence of an AhR agonist. In some embodiments the conditions sufficient to make a RBC comprise culturing in erythroid specification media. In some embodiments the conditions sufficient to make a RBC further comprise culturing in erythroid specification media and culturing in the presence of an AhR agonist.

In some embodiments the methods of making a RBC comprise culturing a MEP in the presence of an AhR agonist. The MEP may be from any source. In some embodiments the methods further comprise culturing the MEP in erythroid specification media.

In some embodiments of the methods, the culture comprises at least 1 million RBCs per ml. In some embodiments the culture comprises at least 10 million RBCs per ml. In some embodiments at least 10% of the cells in the culture are RBCs. In some embodiments at least 50% of the cells in the culture are RBCs. In some embodiments the culture produces at least 10 million RBCs. In some embodiments the culture produces at least 100 million RBCs.

An RBC made by a method of this disclosure is also provided.

Transfusion compositions comprising an RBC made by a method of this disclosure are also provided.

A culture comprising RBCs made by a method of this disclosure are also provided.

This disclosure also provides methods of making a megakaryocyte (Mk). In some embodiments the methods comprise making a MEP by a method of this disclosure, and culturing the MEP under conditions sufficient to make a Mk. In some embodiments the conditions sufficient to make a Mk comprise culturing the MEP in the presence of an AhR modulator. In some embodiments the AhR modulator is an AhR antagonist. In some embodiments, the methods comprise culturing the MEP in the presence of an AhR agonist and then culturing in the presence of an AhR antagonist. In some embodiments the conditions sufficient to make a Mk comprise culturing the MEP in the presence of megakaryocyte specification media. In some embodiments the conditions sufficient to make a Mk comprise culturing a MEP in the presence of an AhR modulator and culturing the MEP in the presence of megakaryocyte specification media. In some such embodiments the AhR modulator is an AhR antagonist. In some such embodiments the methods comprise culturing the MEP in the presence of an AhR agonist and then culturing in the presence of an AhR antagonist.

In some embodiments the methods of making a Mk comprise providing a MEP that was made by a method of this disclosure, and culturing the MEP under conditions sufficient to make a Mk. In some embodiments the conditions sufficient to make a Mk comprise culturing the MEP in the presence of an AhR modulator. In some embodiments the AhR modulator is an AhR antagonist. In some embodiments, the methods comprise culturing the MEP in the presence of an AhR agonist and then culturing in the presence of an AhR antagonist. In some embodiments the conditions sufficient to make a Mk comprise culturing the MEP in the presence of megakaryocyte specification media. In some embodiments the conditions sufficient to make a Mk comprise culturing the MEP in the presence of an AhR modulator and culturing the MEP in the presence of megakaryocyte specification media. In some embodiments the AhR modulator is an AhR antagonist. In some embodiments the conditions sufficient to make a Mk comprise culturing the MEP in the presence of megakaryocyte specification media, and further comprise culturing the MEP in the presence of an AhR agonist and then culturing in the presence of an AhR antagonist.

In some embodiments the methods of making an Mk comprise culturing a MEP in the presence of an AhR modulator. In some embodiments the AhR modulator is an AhR antagonist. The MEP may be from any source. In some embodiments the methods further comprise culturing the MEP in megakaryocyte specification media.

A Mk made by a method of this disclosure is also provided.

A culture comprising Mks made by a method of this disclosure are also provided.

This disclosure also provides methods of making a platelet. In some embodiments the methods of making a platelet comprise making a MEP by a method of this disclosure, culturing the MEP under conditions sufficient to make a Mk, and culturing the Mk under conditions sufficient for differentiation of a platelet from the Mk. In some embodiments the conditions sufficient to make a Mk comprise culturing the MEP in the presence of an AhR modulator. In some embodiments the AhR modulator is an AhR antagonist. In some embodiments the conditions sufficient to make a Mk comprise culturing the MEP in the presence of megakaryocyte specification media. In some embodiments the conditions sufficient to make a Mk comprise culturing the MEP in the presence of an AhR modulator and culturing the MEP in the presence of megakaryocyte specification media. In some embodiments the AhR modulator is an AhR antagonist. In some embodiments culturing the Mk under conditions sufficient for differentiation of a platelet from the Mk comprise culturing the Mk in the presence of an AhR modulator. In some embodiments the AhR modulator is an AhR antagonist. In some embodiments of the methods, the conditions sufficient to make a Mk comprise culturing the MEP in the presence of an AhR agonist and then culturing in the presence of an AhR antagonist. In some embodiments, the conditions sufficient for differentiation of a platelet from the Mk comprise culturing in the presence of an AhR antagonist.

In some embodiments the methods of making a platelet comprise providing a MEP that was made by a method of this disclosure, culturing the MEP under conditions sufficient to make a Mk, and culturing the Mk under conditions sufficient for differentiation of a platelet from the Mk. In some embodiments the conditions sufficient to make a Mk comprise culturing the MEP in the presence of an AhR modulator. In some embodiments the AhR modulator is an AhR antagonist. In some embodiments the conditions sufficient to make a Mk comprise culturing the MEP in the presence of megakaryocyte specification media. In some embodiments the conditions sufficient to make a Mk comprise culturing the MEP in the presence of an AhR modulator and culturing the MEP in the presence of megakaryocyte specification media. In some embodiments the AhR modulator is an AhR antagonist. In some embodiments culturing the Mk under conditions sufficient for differentiation of a platelet from the Mk comprise culturing the Mk in the presence of an AhR modulator. In some embodiments the AhR modulator is an AhR antagonist. In some embodiments of the methods, the conditions sufficient to make a Mk comprise culturing the MEP in the presence of an AhR agonist and then culturing in the presence of an AhR antagonist. In some embodiments, the conditions sufficient for differentiation of a platelet from the Mk comprise culturing in the presence of an AhR antagonist.

In some embodiments the methods of making a platelet comprise culturing a MEP in the presence of an AhR modulator. In some embodiments the AhR modulator is an AhR antagonist. The MEP may be from any source. In some embodiments the methods further comprise culturing the MEP in megakaryocyte specification media. In some embodiments the methods further comprise culturing the resulting Mk under conditions sufficient for differentiation of a platelet. In some embodiments culturing the Mk under conditions sufficient for differentiation of a platelet from the Mk comprise culturing the Mk in the presence of an AhR modulator. In some embodiments the AhR modulator is an AhR antagonist. In some embodiments of the methods, the conditions sufficient to make a Mk comprise culturing the MEP in the presence of an AhR agonist and then culturing in the presence of an AhR antagonist. In some embodiments, the conditions sufficient for differentiation of a platelet from the Mk comprise culturing in the presence of an AhR antagonist.

Methods of differentiating a platelet from a Mk are also provided. In some embodiments the methods comprise culturing the Mk in the presence of an AhR modulator. In some embodiments the AhR modulator is an AhR antagonist. In some embodiments the AhR modulator increases the rate of proplatelet formation in the culture.

A platelet made by a method of this disclosure is also provided.

Transfusion compositions comprising a platelet made by a method of this disclosure are also provided.

This disclosure also provides compositions comprising at least 1 million MEPs per ml. In some embodiments the compositions comprise at least 10 million MEPs per ml. In some embodiments the composition further comprises megakaryocyte erythroid progenitor cells. In some embodiments the composition further comprises RBCs. In some embodiments the composition further comprises megakaryocytes. In some embodiments the composition further comprises platelets.

This disclosure also provides compositions comprising cells, wherein at least 10% of the cells are MEPs. In some embodiments at least 50% of the cells are MEPs. In some embodiments the composition comprises at least 1 million MEPs per ml. In some embodiments the composition comprises at least 10 million MEPs per ml. In some embodiments the composition further comprises megakaryocyte erythroid progenitor cells. In some embodiments the composition further comprises RBCs. In some embodiments the composition further comprises megakaryocytes. In some embodiments the composition further comprises platelets. In some embodiments the composition is a cell culture.

This disclosure also provides methods of providing RBCs to a patient in need thereof. In some embodiments the methods comprise transfusing a composition comprising RBCs made by a method of this disclosure into the circulatory system of the patient.

This disclosure also provides methods of treating anemia in a patient in need thereof. In some embodiments the methods comprise transfusing a composition comprising RBCs made by a method of this disclosure into the circulatory system of the patient. In some embodiments the anemia is caused by at least one of impaired production of RBCs, increased destruction of RBCs, blood loss, and fluid overload. In some embodiments the anemia is caused by thalassemia. In some embodiments the anemia is sickle cell anemia. In some embodiments the RBCs are blood type matched to the patient. In some embodiments the RBCs are differentiated from pluripotent stem cells isolated from the patient.

This disclosure also provides methods of providing platelets to a patient in need thereof. In some embodiments the methods comprise transfusing a composition comprising platelets made by a method of this disclosure into the circulatory system of the patient.

This disclosure also provides methods of treating thrombocytopenia in a patient in need thereof. In some embodiments the methods comprise transfusing a composition comprising platelets made by a method of this disclosure into the circulatory system of the patient. In some embodiments the thrombocytopenia is caused by at least one of decreased production of platelets, increased destruction of platelets, and a medication. In some embodiments the platelets are blood type matched to the patient. In some embodiments the platelets are differentiated from pluripotent stem cells isolated from the patient.

This disclosure also provides methods of screening a compound for an effect on a RBC. In some embodiments the methods comprise a) making a RBC by a method of this disclosure, b) contacting the RBC with the compound, and c) observing a change in the RBC. In some embodiments the method further comprises obtaining an RBC precursor cell from a subject and the RBC is made from the RBC precursor cell obtained from the subject. In some embodiments the RBC precursor cell is a somatic cell.

This disclosure also provides alternative methods of screening a compound for an effect on a RBC. The methods comprise a) providing a RBC that was made by a method of this disclosure, b) contacting the RBC with the compound, and c) observing a change in the RBC. In some embodiments the method further comprises obtaining an RBC precursor cell from a subject and the RBC is made from the RBC precursor cell obtained from the subject. In some embodiments the RBC precursor cell is a somatic cell.

This disclosure also provides methods of screening a compound for an effect on a Mk. In some embodiments the methods comprise a) making a Mk by a method of this disclosure, b) contacting the Mk with the compound, and c) observing a change in the Mk. In some embodiments the method further comprises obtaining a Mk precursor cell from a subject and the Mk is made from the Mk precursor cell obtained from the subject. In some embodiments the Mk precursor cell is a somatic cell.

This disclosure also provides alternative methods of screening a compound for an effect on a Mk. In some embodiments the methods comprise a) providing a Mk that was made by a method of this disclosure, b) contacting the Mk with the compound, and c) observing a change in the Mk. In some embodiments the method further comprises obtaining a Mk precursor cell from a subject and the Mk is made from the Mk precursor cell obtained from the subject. In some embodiments the Mk precursor cell is a somatic cell.

This disclosure also provides methods of screening a compound for an effect on a platelet. In some embodiments the methods comprise a) making a platelet by a method of this disclosure, b) contacting the platelet with the compound, and c) observing a change in the platelet. In some embodiments the method further comprises obtaining a platelet precursor cell from a subject and the platelet is made from the platelet precursor cell obtained from the subject. In some embodiments the platelet precursor cell is a somatic cell.

This disclosure also provides alternative methods of screening a compound for an effect on a platelet. In some embodiments the methods comprise providing a platelet that was made by a method of this disclosure, b) contacting the platelet with the compound, and c) observing a change in the platelet. In some embodiments the method further comprises obtaining a platelet precursor cell from a subject and the platelet is made from the platelet precursor cell obtained from the subject. In some embodiments the platelet precursor cell is a somatic cell.

This disclosure also provides methods of increasing the platelet count of a mammal. In some embodiments the methods comprise administering an effective amount of an AhR agonist to the mammal.

This disclosure also provides methods of treating thrombocytopenia in a mammal. In some embodiments the methods comprise administering an effective amount of an AhR agonist to the mammal.

This disclosure also provides methods of making a platelet comprising culturing an Mk in the presence of an AhR modulator. In some embodiments the AhR modulator is an AhR antagonist. In some embodiments the AhR antagonist has the effect of increasing the rate of production of pro-platelets in the culture.

DETAILED DESCRIPTION

Figure 1A:
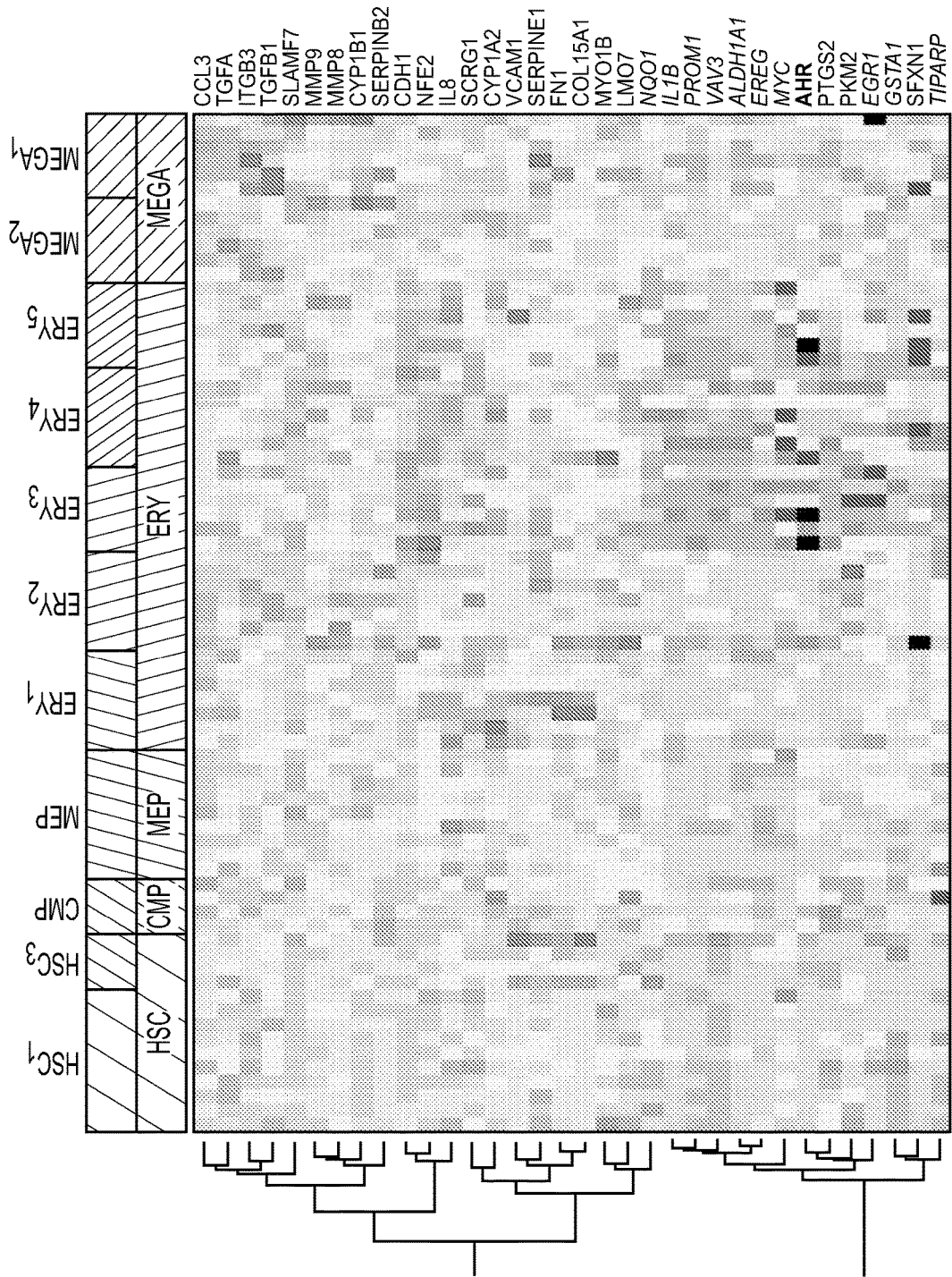
FIGS. 1A to 1B shows an analysis of human hematopoietic cell differentiation genomic mapping (dMap) data. A computational analysis of comprehensive microarray data obtained through the Broad Institute's Differential Map Portal (dMAP) was performed. The genes were sorted based on hierarchical clustering with 1-Pearson correlation as the distance metric, and average linkage as the agglomeration rule (1A). The normalized expression level of AhR within each cell population (sub-population) was computed and visualized by means of box-and-whiskers plots (1B). For each population, the plot reports the median (thick mid line), the middle half (the box), and the Interquartile Range (IQR, the distance between the "whiskers") of the distribution of AhR values. The difference in the expression level of AhR among cell populations was tested by standard analysis-of-variance (anova).

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all Genbank or other sequence database records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3d ed., Cold Spring Harbor Laboratory Press, Cold Spring Harbor, N.Y. (2001); Ausubel et al., Current Protocols in Molecular Biology, Greene Publishing Associates (1992, and Supplements to 2002); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999).

This disclosure refers to sequence database entries (e.g., Genbank and UniProt records) for certain amino acid and nucleic acid sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The MEPs, RBCs, megakaryocytes, and platelets of this disclosure are typically mammalian or marsupial cells. As used herein "mammal" and "mammalian" refers to any member of the taxonomic class mammal, including without limitation, all primates including humans; rodents, including mice and rats; farm animals including pigs, horses, cattle, sheep, and goats; and companion animals including dogs and cats.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, a protein has "homology" or is "homologous" to a second protein if the nucleic acid sequence that encodes the protein has a similar sequence to the nucleic acid sequence that encodes the second protein. Alternatively, a protein has homology to a second protein if the two proteins have similar amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89.

The following six groups each contain amino acids that are conservative substitutions for one another: 1) Serine, Threonine; 2) Aspartic Acid, Glutamic Acid; 3) Asparagine, Glutamine; 4) Arginine, Lysine; 5) Isoleucine, Leucine, Methionine, Alanine, Valine, and 6) Phenylalanine, Tyrosine, Tryptophan.

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

An exemplary algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

Exemplary parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, or at least about 20 residues, or at least about 24 residues, or at least about 28 residues, or more than about 35 residues. When searching a database containing sequences from a large number of different organisms, it may be useful to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990). For example, percent sequence identity between amino acid sequences can be determined using FASTA with its default parameters (a word size of 2 and the PAM250 scoring matrix), as provided in GCG Version 6.1, herein incorporated by reference.

In some embodiments, polymeric molecules (e.g., a polypeptide sequence or nucleic acid sequence) are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotides sequences or amino acid sequences). In some embodiments, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. In some embodiments of nucleotide sequences less than 60 nucleotides in length, homology is determined by the ability to encode a stretch of at least 4-5 uniquely specified amino acids. In some embodiments, two protein sequences are considered to be homologous if the proteins are at least about 50% identical, at least about 60% identical, at least about 70% identical, at least about 80% identical, or at least about 90% identical for at least one stretch of at least about 20 amino acids.

As used herein, a "modified derivative" refers to polypeptides or fragments thereof that are substantially homologous in primary structural sequence to a reference polypeptide sequence but which include, e.g., in vivo or in vitro chemical and biochemical modifications or which incorporate amino acids that are not found in the reference polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands that bind to labeled antiligands (e.g., antibodies), fluorophores, chemiluminescent agents, enzymes, and antiligands that can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., Current Protocols in Molecular Biology, Greene Publishing Associates (1992, and Supplements to 2002).

As used herein, "polypeptide mutant" or "mutein" refers to a polypeptide whose sequence contains an insertion, duplication, deletion, rearrangement or substitution of one or more amino acids compared to the amino acid sequence of a reference protein or polypeptide, such as a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the reference protein, and/or truncations of the amino acid sequence at either or both the amino or carboxy termini. A mutein may have the same or a different biological activity compared to the reference protein.

In some embodiments, a mutein has, for example, at least 85% overall sequence homology to its counterpart reference protein. In some embodiments, a mutein has at least 90% overall sequence homology to the wild-type protein. In other embodiments, a mutein exhibits at least 95% sequence identity, or 98%, or 99%, or 99.5% or 99.9% overall sequence identity.

As used herein, the term "agonist" refers to an agent that triggers a response that is at least one response triggered by binding of an endogenous ligand of a receptor to the receptor. In some embodiments, the agonist may act directly or indirectly on a second agent that itself modulates the activity of the receptor. In some embodiments, the at least one response of the receptor is an activity of the receptor that can be measured with assays including but not limited to physiological, pharmacological, and biochemical assays. Exemplary assays include but are not limited to assays that measure the binding of an agent to the receptor, the binding of the receptor to a substrate such as but not limited to a nuclear receptor and a regulatory element of a target gene, the effect on gene expression assayed at the mRNA or resultant protein level, and the effect on an activity of proteins regulated either directly or indirectly by the receptor. For example, AhR receptor activity may be measures by monitoring the expression of an AhR-target gene, such as CYP1B1.

As used herein, the term "antagonist" refers to an agent that inhibits a response that is at least one response triggered by binding of an agonist of a receptor to the receptor. In some embodiments, the antagonist may act directly or indirectly on a second agent that itself modulates the activity of the receptor. In some embodiments, the at least one response of the receptor is an activity of the receptor that can be measured with assays including but not limited to physiological, pharmacological, and biochemical assays. Exemplary assays include but are not limited to assays that measure the binding of an agent to the receptor, the binding of the receptor to a substrate such as but not limited to a nuclear receptor and a regulatory element of a target gene, the effect on gene expression assayed at the mRNA or resultant protein level, and the effect on an activity of proteins regulated either directly or indirectly by the receptor. For example, AhR receptor activity may be measures by monitoring the expression of an AhR-target gene, such as CYP1B1.

As used herein, the term "agent" or "active agent" refers to a substance including, but not limited to a chemical compound, such as a small molecule or a complex organic compound, a protein, such as an antibody or antibody fragment or a protein comprising an antibody fragment, or a genetic construct which acts at the DNA or mRNA level in an organism.

As used herein, the term "modulating" and "modulate" refers to changing or altering an activity, function, or feature. The term "modulator" refers to an agent which modulates an activity, function, or feature. For example, an agent may modulate an activity by increasing or decreasing the activity compared to the effects on the activity in the absence of the agent. In some embodiments, a modulator that increases an activity, function, or feature is an agonist. In some embodiments, a modulator that increases an activity, function, or feature is an antagonist.

As used herein, the terms "treat," "treatment," "treating," and "amelioration" refer to therapeutic treatments, wherein the object is to reverse, alleviate, ameliorate, inhibit, slow down and/or stop the progression or severity of a condition associated with a disease or disorder. The terms include reducing or alleviating at least one adverse effect or symptom of a condition, disease or disorder associated with a deficiency in the number or defect in the quality of at least one blood cell type, such as platelets. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The terms "treat," "treatment," "treating," and "amelioration" in reference to a disease also include providing relief from the symptoms or side-effects of the disease (including palliative treatment).

As used herein, "co-administered" and "co-administration" refer to administration of at least two agents to a mammal to treat a condition, wherein the at least two agents are administered for therapeutic dosing periods that overlap for administration of at least one does of each agent. For example, if agent A is administered on day 1, agent B is administered on day 2, and agent A is administered on day 3 then agents A and B are co-administered. Therapeutic dosing periods may comprise 1, 2, 3, 4, 5, 6, 7, 8, 9, or 10 or more administrations of an agent. Administration may be daily, three times a week, two times a week, weekly, every two weeks, or monthly, for example.

A. Introduction to the Disclosure

The differentiation of HSCs into all eight blood cell lineages is a tightly regulated and critical physiological process that changes in subtle but important ways during the lifespan of the individual. Disruption of this regulation can have a profound downstream effect on multiple hematopoietic cell types, potentially leading to myelodysplasia, mixed lineage leukemias, CIVIL, lymphomas, stem cell exhaustion, thrombocytopenia, anemia and other blood cell disorders. However, definition of the molecular mechanisms that control specification of primary human blood cells has been hampered by a lack of platforms with which sufficient numbers of stem or progenitor cells can be grown and the absence of practical and efficient techniques for directing differentiation of those cells into end stage cells. For example, several teams have published proof-of-principle examples of the derivation of megakaryocytes (Mks) (1) and erythroid-lineage cells (2) from embryonic stem cells (ESC) and induced pluripotent stem cells (iPSC). However, development of a model system which results in robust expansion of these cell populations and with which molecular signals driving cell differentiation can readily be studied has been problematic.

Our conceptual approach to addressing this glaring unmet need has been to mimic the natural sequences of hematopoietic cell development in vitro to derive the number and range of cells types needed for the creation of a genetically tractable iPSC-based platform. A key component of this new platform, as shown here, is the demonstration that aryl hydrocarbon receptor (AhR) hyper-activation enables outgrowth of myeloid-erythroid progenitor cells and production of Mk and erythroid-lineage cells from iPSCs.

The AhR is a member of the evolutionarily conserved Per/ARNT/SIM (PAS) family of transcription factors. It is the only PAS family member known to be activated by endogenous or exogenous ligands. PAS proteins contribute to several important physiological processes. Historically, the evolutionarily conserved AhR was studied in the context of its activation by a variety of ubiquitous environmental pollutants including dioxins, polychlorinated biphenyls, and polycyclic aromatic hydrocarbons, and subsequent transactivation of cytochrome P450-encoding genes, the products of which catalyze production of mutagenic or toxic intermediates. However, the AhR field has recently undergone a major paradigm shift following the demonstration that the AhR plays important physiological roles in the absence of environmental ligands. For example, several studies demonstrate that the AhR contributes to regulation of autoimmune responses, inflammation, cell growth, cell migration, apoptosis and cancer progression. Specifically with regard to hematopoietic cells, several high profile studies demonstrate that the AhR regulates development of Th17 cells, regulatory T cells subsets, and gut-associated T cells.

Importantly, recent breakthrough studies suggest that the AhR plays a critical role in nominal HSC growth and differentiation. For example, AhR−/− mice are characterized by an increased number of bone marrow HSCs and a commensurate increased propensity to develop lymphomas. Furthermore, AhR−/− mice produce decreased numbers of erythrocytes and platelets, lower-ploidy Mks, and increased numbers of B lineage and myeloid cells. These results led to the hypothesis that the AhR, activated by endogenous ligands, regulates stem cell growth and/or differentiation.

Despite these early results, many important questions remain. Specifically, little is known of the effects of AhR modulation on the development of Mk or erythroid-lineage cells from bipotential progenitors. That the AhR is involved in this process is suggested by decreased numbers of HSCs, erythrocytes and platelets in young AhR−/− mice and the skewing of the blood cell repertoire towards myeloid and B lineage cells as AhR−/− mice age.

To build on these studies and to develop a robust system for studying Mk and erythroid cell differentiation, we developed a novel, feeder-free and chemically-defined protocol for the directed differentiation of iPSCs into hematopoietic progenitor cells and their progeny. A necessary component of this system was shown to be the hyper-activation of the AhR with a potent AhR agonist, 6-formylindole(3,2-b)carbazole (FICZ). The in vitro system described herein allows, in some embodiments, the capture in culture and expansion of pure populations of megakaryocyte-erythroid progenitors that exist transiently during in vivo development in the production of end stage red blood cells (RBCs) and Mks. This platform in some embodiments allows for unprecedented efficiency and consistency in the derivation of bi-potential hematopoietic progenitors and progeny production from pluripotent stem cells using AhR modulation. In addition to demonstrating a critical role for the AhR in MEP, Mk, and RBC development, the platform provides an important and genetically tractable system for studying blood cell differentiation at multiple, defined stages of development. Perhaps most importantly, the platform presented here represents a significant step forward towards the in vitro production of therapeutic, patient-specific platelets and RBC.

Furthermore, this work indicates that AhR has a physiological and functional role in hematopoiesis, and that modulation of the receptor in bi-potential hematopoietic progenitors can direct cell fate.

B. Stem Cells

Stem cells are cells in multicellular organisms that can divide and differentiate into diverse specialized cell types and can self-renew to produce more stem cells that have the same property. A "pluripotent stem cell" as used herein is a stem cell that has the potential to differentiate into any of the three germ layers: endoderm (e.g., interior stomach lining, gastrointestinal tract, the lungs), mesoderm (e.g., muscle, bone, blood, urogenital system), and ectoderm (e.g., epidermal tissues and nervous system). Pluripotent stem cells can give rise to any fetal or adult cell type. For the purposes of this disclosure a "pluripotent stem cell" may include a totipotent stem cell, which is a cell that can construct a complete, viable organism. These cells are produced from the fusion of an egg and sperm cell. Cells produced by the first few divisions of the fertilized egg are also totipotent. Pluripotent stem cells include but are not limited to embryonic stem (ES) cells, induced pluripotent stem cells (iPSC), and cells produced by somatic cell nuclear transfer (SCNT).

ES cells are totipotent stem cells derived from the inner cell mass of the blastocyst of an early-stage mammalian embryo. Methods of deriving mammalian ES cells are well known in the art as are numerous established ES cell lines that may be used in conjunction with certain embodiments of this disclosure.

iPSCs are a type of pluripotent stem cell artificially derived from a non-pluripotent cell—typically an adult somatic cell—by inducing the "forced" expression of specific genes. Induced pluripotent stem cells are similar to natural pluripotent stem cells, such as embryonic stem (ES) cells, in many aspects, such as, in some embodiments, at least one of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

iPSCs are typically derived by transfection of certain stem cell-associated genes into non-pluripotent cells, such as adult fibroblasts. Transfection is typically achieved through viral vectors, such as retroviruses. Transfected genes may include the master transcriptional regulators Oct-3/4 (Pou5f1) and Sox2. Over time following transfection small numbers of transfected cells begin to become morphologically and biochemically similar to pluripotent stem cells, and are typically isolated through at least one of morphological selection, doubling time, a reporter gene and antibiotic selection.

In some embodiments the iPSC is formed by a method comprising transfecting a somatic cell with open reading frames that encode the Oct-3/4, SOX2, c-Myc, and Klf4 proteins. In some embodiments the iPSC is formed by a method comprising transfecting a somatic cell with open reading frames that encode the OCT4, SOX2, NANOG, and LIN28 proteins. In some embodiments the transfection comprises introducing a retroviral vector into the somatic cell. In alternative embodiments, the iPSC is formed by a method comprising treating the somatic cell with at least one small molecule inducer of iPSC formation. In some embodiments the iPSC is formed by a method comprising treating the somatic cell with at least one small molecule inducer of iPSC formation and transfecting the somatic cell with open reading frames that encodes a protein inducer of iPSC formation. In such embodiments the at least one protein may be selected from Oct-3/4, SOX2, c-Myc, Klf4, NANOG, and LIN28.

iPSCs can give rise to multipotent stem cells. In the hematopoietic lineage an iPSC or ES cell can give rise to a cell in a hemangioblastic state. The hemangioblastic cell then in turn gives rise to a hematopoietic stem cell which gives rise to MEP cells.

As will be apparent to a skilled artisan reading this disclosure, any pluripotent stem cell or any multipotent stem cell capable of differentiating into a MEP may be used in embodiments of the methods disclosed herein to make RBCs and/or platelets.

C. Hematopoietic Cell Types

All cellular blood components are derived from hematopoietic stem cells (HSCs). In a healthy adult person, approximately $10^{11}$-$10^{12}$ new blood cells are produced daily in order to maintain steady state levels in the peripheral circulation. HSCs reside in the medulla of the bone (bone marrow) and have the unique ability to give rise to all of the different mature blood cell types. HSCs are self-renewing: when they proliferate, at least some of their daughter cells remain as HSCs, so the pool of stem cells does not become depleted. The other daughters of HSCs (myeloid and lymphoid progenitor cells), however, can each commit to any of the alternative differentiation pathways that lead to the production of one or more specific types of blood cells, but cannot self-renew. HSCs give rise to common myeloid progenitor cells and common lymphoid progenitor cells. This disclosure identifies a cell type downstream of the common myeloid progenitor cell, termed a myeloid-erythroid progenitor cell (MEP), which can give rise to red blood cells and megakaryocytes (which in turn can differentiate into platelets).

1. Myeloid-Erythroid Progenitor Cells

A "myeloid-erythroid progenitor cell" (or MEP) as used herein, is a cell that gives rise to megakaryocytes and erythrocytes. It is most commonly derived from a common myeloid progenitor cell. In some embodiments the MEP is characterized by co-expression of glycophorin A (also known as CD235 in humans) protein (e.g., Uniprot #P02724 in humans), a marker of the erythroid lineage, and integrin alpha 2b (CD41 in humans) protein (e.g., Uniprot #P08514 in humans), a marker of megakaryocyte lineage (Klimchenko et. al., Blood, 2009, 114(8):1506-17). In some embodiments the MEP does not express CD34.

2. Red Blood Cells

Red blood cells, or erythrocytes, are the most common type of blood cell and the vertebrate organism's principal means of delivering oxygen ($O_2$) to the body tissues via the blood flow through the circulatory system. They take up oxygen in the lungs or gills and release it while squeezing through the body's capillaries. The cytoplasm of RBCs is rich in haemoglobin, an iron-containing biomolecule that can bind oxygen and is responsible for the blood's red color.

In humans, mature red blood cells are oval and flexible biconcave disks. They lack a cell nucleus and most organelles to accommodate maximum space for haemoglobin. 2.4 million new erythrocytes are produced per second. The cells develop in the bone marrow and circulate for about 100-120 days in the body before their components are recycled by macrophages. Each circulation takes about 20 seconds. Approximately a quarter of the cells in the human body are red blood cells.

In some embodiments a "red blood cell" is a cell that co-expresses glycophorin A (also known as CD235 in humans) protein (e.g., Uniprot #P02724 in humans) and transferrin receptor (CD71 in humans) protein (e.g., Uniprot #P02786 in humans) (Hattangadi et. al., Blood, 2011, 118 (24):6258-68.). In some embodiments the red blood cell further expresses at least one hemoglobin gene. In some embodiments the red blood cell expresses fetal hemoglobin (HbF), and both the alpha and beta subunits of adult type hemoglobin (HbA and HbB). Typically, the cells resemble hematopoietic progenitor cells, and with maturity, reduce in size and display chromatin condensation (both also signs of maturing RBCs).

3. Megakaryocytes

The megakaryocyte is a bone marrow cell responsible for the production of blood thrombocytes (platelets), which are necessary for normal blood clotting. Megakaryocytes normally account for 1 out of 10,000 bone marrow cells but can increase in number nearly 10-fold during the course of certain diseases. In general, megakaryocytes are 10 to 15 times larger than a typical red blood cell, averaging 50-100 μm in diameter. During its maturation, the megakaryocyte grows in size and replicates its DNA without cytokinesis in a process called endomitosis. As a result, the nucleus of the megakaryocyte can become very large and lobulated, which, under a light microscope, can give the false impression that there are several nuclei. In some cases, the nucleus may contain up to 64N DNA, or 32 copies of the normal complement of DNA in a human cell. The cytoplasm, just as the platelets that bud off from it, contains α-granula and Dense bodies.

In some embodiments a "megakaryocyte" is a cell that co-expresses integrin alpha 2b (CD41 in humans) protein (e.g., Uniprot #P08514 in humans) and glycoprotein Ib (CD42 in humans) protein (e.g., Uniprot #P07359 in humans) (Yu and Cantor, Methods Mol Biol, 2012; 788: 291-303). In some embodiments the megakaryocyte expresses GP1balpha. In some embodiments the megakaryocyte further expresses the vWF (von Willebrand's receptor) as well as CD62P (p selectin). In some embodiments a "megakaryocyte" is a cell that exhibits at least one of a characteristic polyploidy, the ability to endoreplicate in the production of cells up to at least 8N or at least 16N, and noticeable proplatelet extrusions at the surface of the cells (Kaushansky, J Clin Invest, 2005 December; 115(12):3339-47). In some embodiments a megakaryocyte is 2N or 4N.

4. Platelets

Platelets, or thrombocytes, are small, irregularly shaped clear cell fragments (i.e. cells that do not have a nucleus containing DNA), 2-3 μm in diameter, which are derived from fragmentation of precursor megakaryocytes. The average lifespan of a platelet is normally just 5 to 9 days. Platelets are a natural source of growth factors. They circulate in the blood of mammals and are involved in hemostasis, leading to the formation of blood clots.

In some embodiments platelets are identified by expression of mature megakaryocyte markers, such as CD62P. For functionality, platelet adhesion assays are performed or inside out and outside in signaling assays in which the GPIIb/GPIIIa (CD41a/CD42b) complex is interrogated.

5. Precursor Cells

Figure 19:
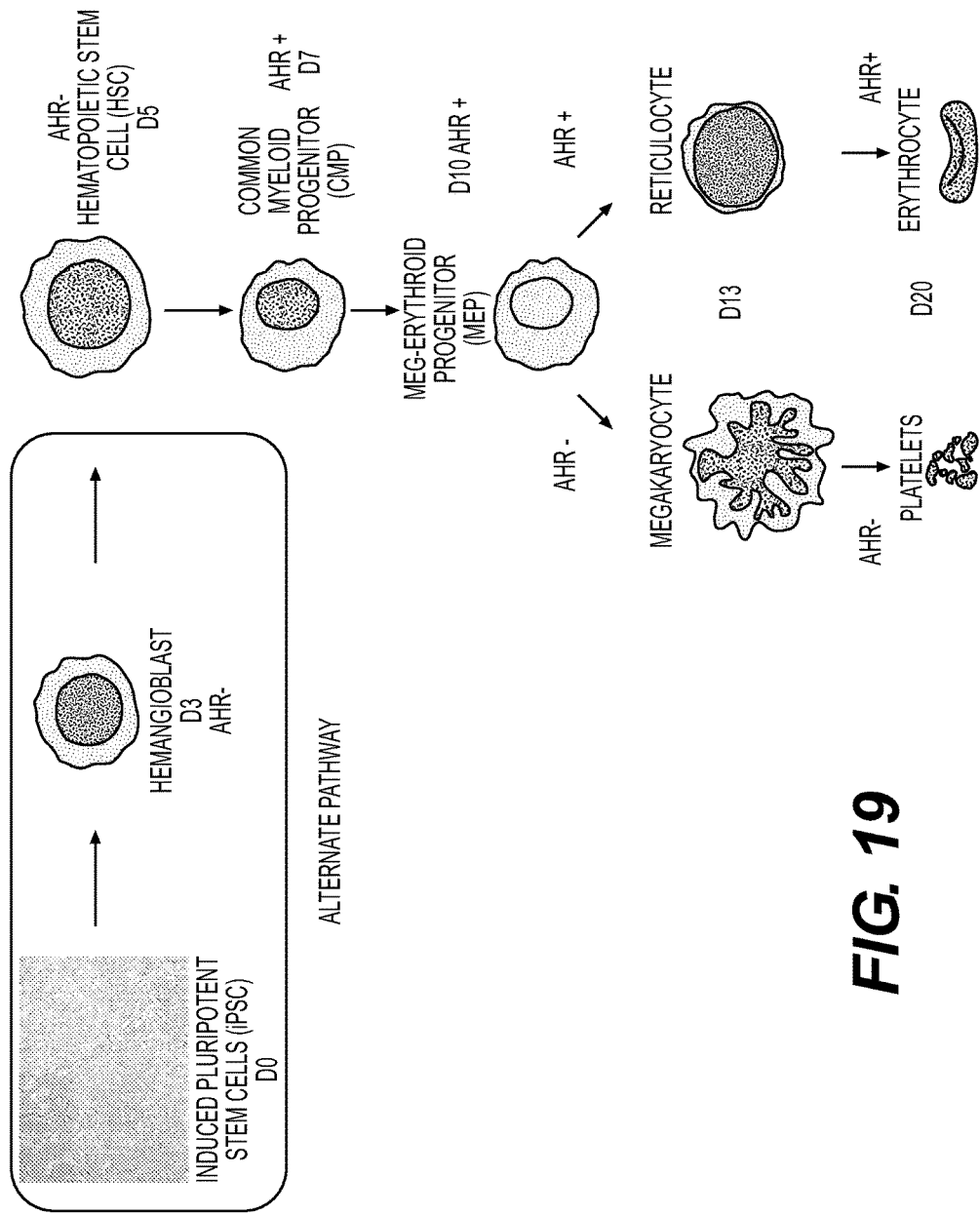
FIG. 19 shows a schematic representation of the roles of AhR modulation in the differentiation of cultured red blood cells (cRBCs) and platelets. In this process, both AhR agonism (AHR+) and AhR antagonism (AHR−) are employed.

FIG. 19 presents a series of cell types formed during differentiation of a pluripotent stem cell into a platelet or RBC. For any give cell type identified in FIG. 19, all upstream cell types that have the potential to differentiate into the given cell type are "precursor" cells of that given cell type. Thus, precursor cells of HSCs include PSCs and hemangioblasts.

For the purpose of this disclosure, a "MEP precursor cell" is any cell with the potential to differentiate into a MEP. The term includes, without limitation, pluripotent stem cells, hemangioblasts, hematopoietic stem cells (HSCs), and common myeloid progenitor cells (CMPs).

For the purpose of this disclosure, a "megakaryocyte precursor cell" is any cell with the potential to differentiate into a megakaryocyte. The term includes, without limitation, pluripotent stem cells, hemangioblasts, hematopoietic stem cells (HSCs), common myeloid progenitor cells (CMPs), and MEPs.

For the purpose of this disclosure, a "platelet precursor cell" is any cell with the potential to differentiate into a platelet. The term includes, without limitation, pluripotent stem cells, hemangioblasts, hematopoietic stem cells (HSCs), common myeloid progenitor cells (CMPs), MEPs, and megakaryocytes.

For the purpose of this disclosure, a "reticulocyte precursor cell" is any cell with the potential to differentiate into a reticulocyte. The term includes, without limitation, pluripotent stem cells, hemangioblasts, hematopoietic stem cells (HSCs), common myeloid progenitor cells (CMPs), and MEPs.

For the purpose of this disclosure, a "erythrocyte precursor cell" or "RBC precursor cell" is any cell with the potential to differentiate into a reticulocyte (also known as an RBC). The term includes, without limitation, pluripotent stem cells, hemangioblasts, hematopoietic stem cells (HSCs), common myeloid progenitor cells (CMPs), MEPs, and reticulocytes.

D. Methods of Making Megakaryocyte-Erythroid Progenitor Cells (MEPs)

This disclosure also provides methods of making MEPs from MEP precursor cells. In some embodiments the MEP precursor cell is a stem cell, such as pluripotent stem cells. As demonstrated in the examples, the inventors have established methods and protocols for differentiating a pluripotent stem cell into a MEP in culture. Without wishing to be bound by any theory it is believed that the methods demonstrated in the examples using pluripotent stem cells as the starting cells are broadly applicable to the use of hemangioblastic cells, hematopoietic stem cells, or common myeloid progenitor cells as well.

In some non-limiting embodiments the methods enable at least one of producing MEPs at a faster rate and producing MEPs over a longer period of time in the culture, compared to prior art methods. In some embodiments the MEP precursor cell (e.g., a pluripotent stem cell) is differentiated into a MEP in the presence of an aryl hydrocarbon receptor (AhR) modulatory. As demonstrated in the examples, the presence of an AhR agonist in the culture during the differentiation process enables, in some embodiments, exponential production of MEPs. Thus, in some embodiments the number of MEPs produced in the culture increases exponentially. In some embodiments the number of MEPs produced in the culture increases exponentially over a culture period of at least 3 hours, at least 6 hours, at least 12 hours, at least 24 hours, at least 36 hours, at least 48 hours, at least 1 week, at least 2 weeks, at least 3 weeks, or at least 30 days, for example.

Differentiation of a MEP precursor cell (e.g., a pluripotent stem cell) into a MEP may be a multi-step process, depending on the type(s) of MEP precursor used. For example, if the MEP precursor is a pluripotent stem cell the PSC will undergo a series of cell fate determinations as it differentiates from a starting pluripotent state, to a hemangioblastic (hematopoietic-endothelial) state, to a multipotent HSC state, to a MEP fate. Of course, if a hemangioblastic (hematopoietic-endothelial) cell or a multipotent HSC cell is used as the starting cell to differentiate a MEP the initial steps of the procedure may be eliminated or modified. By "differentiating a stem cell such as a pluripotent stem cell into a MEP in culture in the presence of an aryl hydrocarbon receptor (AhR) modulator," is meant that the AhR modulator is present in culture media for at least a sub-period of the total cell culture period. In some embodiments the sub-period is selected from 1 to 12 hours, from 3 to 12 hours, from 6 to 12 hours, from 6 to 24 hours, from 12 to 24 hours, from 1 to 2 days, from 2 to 4 days, from 3 to 6 days, 1 to 2 weeks, from 2-4 weeks, and from 4-8 weeks. In some embodiments the sub-period is selected from at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 24 hours, at least 36 hours, at least 2 days, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, and at least 8 weeks. In some embodiments the MEP precursor cell is a pluripotent stem cell. In some embodiments the AhR modulator is an AhR agonist.

In some embodiments the AhR modulator is present for the entire culture period. In some embodiments culture of the MEP precursor cell is initiated in the absence of the AhR modulator and the AhR modulator is added after a period of time selected from at least 1 day, at least 2 days, at least 3 days, at least 4 days, at least 5 days, at least 6 days, at least 1 week, and at least 2 weeks. In some embodiments culture of the MEP precursor cell is initiated in the absence of the AhR modulator and the AhR modulator is added after a period of time selected from: from 12 to 24 hours, from 1 to 2 days, from 1 to 3 days, from 2 to 4 days, from 3 to 6 days, from 4 to 7 days, from 5 to 10 days, from 6 to 10 days, and from 7 to 10 days. In some embodiments the MEP precursor cell is a pluripotent stem cell. In some embodiments the AhR modulator is an AhR agonist.

In some embodiments the MEP precursor cell is cultured for a first period of time in the presence of an AHR antagonist and then cultured for a second period of time in the presence of an AHR agonist. In some embodiments the first period of time is selected from 1 to 12 hours, from 3 to 12 hours, from 6 to 12 hours, from 6 to 24 hours, from 12 to 24 hours, from 1 to 2 days, from 2 to 4 days, from 3 to 6 days, 1 to 2 weeks, from 2-4 weeks, and from 4-8 weeks. In some embodiments the first period of time is selected from at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 24 hours, at least 36 hours, at least 2 days, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, and at least 8 weeks. In some embodiments the second period of time is selected from 1 to 12 hours, from 3 to 12 hours, from 6 to 12 hours, from 6 to 24 hours, from 12 to 24 hours, from 1 to 2 days, from 2 to 4 days, from 3 to 6 days, 1 to 2 weeks, from 2-4 weeks, and from 4-8 weeks. In some embodiments the second period of time is selected from at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 24 hours, at least 36 hours, at least 2 days, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, and at least 8 weeks.

In some embodiments the methods comprise culturing in the absence of an AhR modulator for a third period of time. In some embodiments the third period of time is after the first period of time and before the second period of time. In some embodiments a pluripotent stem cell is differentiated into a MEP in culture in the presence of at least one protein selected from BMP-4 (e.g., Uniprot #P12644 in humans), vVEGF (e.g., Uniprot #P15692 in humans), WNT3a (e.g., Uniprot #P56704 in humans), bFGF (e.g., Uniprot #P09038 in humans), hSCF (e.g., Uniprot #P21583 in humans), FLT3 (e.g., Uniprot #P36888 in humans), TPO (e.g., Uniprot #P40225 in humans), and EPOgen (e.g., Uniprot #P01588 in humans). In some embodiments one or more of those proteins is replaced with another protein having a similar activity. In some embodiments one of those listed proteins is replaced with a protein that has at least one characteristic selected from being a fragment of the listed protein, a fusion protein comprising a fragment of the listed protein or the whole listed protein, a homologue of the listed protein, a modified derivative of the listed protein, or a mutein of the listed protein. In some embodiments an AhR agonist is present in the culture together with the at least one factor. In some embodiments a pluripotent stem cell is differentiated into a MEP in culture by a method that does not comprise culturing in the presence of a AhR agonist.

In some embodiments a pluripotent stem cell is differentiated into a MEP in culture by a method comprising culturing in at least one culture media comprising a combination of factors, the culture media and factor combination comprising a composition selected from:

a) RPMI media supplemented with BMP-4 (e.g., Uniprot #P12644 in humans), VEGF (e.g., Uniprot #P15692 in humans), Wnt3a (e.g., Uniprot #P56704 in humans), and knockout serum replacement (KOSR) (in some embodiments the ratio of BMP-4:VEGF:Wnt3a is about 1:10:5);

b) RPMI media supplemented with BMP-4 (e.g., Uniprot #P12644 in humans), VEGF (e.g., Uniprot #P15692 in humans), bFGF (e.g., Uniprot #P09038 in humans) and KOSR; (in some embodiments the ratio of BMP-4:VEGF:bFGF is about 1:10:4);

c) StemPro 34 media supplemented with BMP-4 (e.g., Uniprot #P12644 in humans), VEGF (e.g., Uniprot #P15692 in humans), and bFGF (e.g., Uniprot #P09038 in humans) (in some embodiments the ratio of BMP-4:VEGF:bFGF is about 1:10:4);

d) StemPro 34 media supplemented with VEGF (e.g., Uniprot #P15692 in humans), and bFGF (e.g., Uniprot #P09038 in humans) (in some embodiments the ratio of VEGF:bFGF is about 3:1);

e) a mixture of IMDM and Hams F12 media supplemented with B27, N2-supplement, BSA, VEGF (e.g., Uniprot #P15692 in humans), bFGF (e.g., Uniprot #P09038 in humans), hSCF (e.g., Uniprot #P21583 in humans), and Flt3 ligand (e.g., Uniprot #P36888 in humans) (in some embodiments the ratio of VEGF:bFGF:hSCF:Flt3 ligand is about 2:4:4:1);

f) a mixture of IMDM and Hams F12 media supplemented with B27, N2-supplement, BSA, VEGF (e.g., Uniprot #P15692 in humans), bFGF (e.g., Uniprot #P09038 in humans), hSCF (e.g., Uniprot #P21583 in humans), Flt3 ligand (e.g., Uniprot #P36888 in humans), and (e.g., Uniprot #P40225 in humans), IL-6 (e.g., Uniprot #P05231 in humans), EPOgen (e.g., Uniprot #P01588 in humans) (in some embodiments the ratio of VEGF:bFGF:hSCF:Flt3 Ligand:hTPO:IL-6 is about 5:10:10:2.5:10:1); and g) a mixture of IMDM and Hams F12 media supplemented with B27, N2-supplement, BSA, VEGF (e.g., Uniprot #P15692 in humans), bFGF (e.g., Uniprot #P09038 in humans), hSCF (e.g., Uniprot #P21583 in humans), Flt3 ligand (e.g., Uniprot #P36888 in humans), and hTPO (e.g., Uniprot #P40225 in humans), IL-6 (e.g., Uniprot #P05231 in humans), EPOgen (e.g., Uniprot #P01588 in humans) and an AhR agonist (in some embodiments the ratio of VEGF:bFGF:hSCF:Flt3 Ligand:hTPOIL-6 is about 5:10:10:2.5:10:1).

In some embodiments a pluripotent stem cell is differentiated into a MEP in culture by a method comprising culturing in at least one culture media comprising a combination of factors, the culture media and factor combination comprising a composition selected from:

a) RPMI media supplemented with 4-6 ng/ml BMP-4 (e.g., Uniprot #P12644 in humans), 40-60 ng/ml VEGF (e.g., Uniprot #P15692 in humans), 20-30 ng/ml Wnt3a (e.g., Uniprot #P56704 in humans), and 10% knockout serum replacement (KOSR) (in some embodiments the ratio of BMP-4:VEGF:Wnt3a is about 1:10:5;

b) RPMI media supplemented with 4-6 ng/ml BMP-4 (e.g., Uniprot #P12644 in humans), 40-60 ng/ml VEGF (e.g., Uniprot #P15692 in humans), 16-24 ng/ml bFGF (e.g., Uniprot #P09038 in humans) and 10% KOSR (in some embodiments the ratio of BMP-4:VEGF:bFGF is about 1:10:4);

c) StemPro 34 media supplemented with 4-6 ng/ml BMP-4 (e.g., Uniprot #P12644 in humans), 40-60 ng/ml VEGF (e.g., Uniprot #P15692 in humans), and 16-24 ng/ml bFGF (e.g., Uniprot #P09038 in humans) (in some embodiments the ratio of BMP-4:VEGF:bFGF is about 1:10:4);

d) StemPro 34 media supplemented with 40-60 ng/ml VEGF (e.g., Uniprot #P15692 in humans), and 4-6 ng/ml bFGF (e.g., Uniprot #P09038 in humans)(in some embodiments the ratio of VEGF:bFGF is about 3:1);

e) a mixture of IMDM and Hams F12 media supplemented with 1% B27, 0.5% N2-supplement, 0.5% BSA, 12-18 ng/ml VEGF (e.g., Uniprot #P15692 in humans), 4-6 ng/ml bFGF (e.g., Uniprot #P09038 in humans), 80-120 ng/ml hSCF (e.g., Uniprot #P21583 in humans), and 20-30 ng/ml Flt3 ligand (e.g., Uniprot #P36888 in humans) (in some embodiments the ratio of VEGF:bFGF:hSCF:Flt3 ligand is about 2:4:4:1);

f) a mixture of IMDM and Hams F12 media supplemented with B27, N2-supplement, BSA, 40-60 ng/ml VEGF (e.g., Uniprot #P15692 in humans), 80-120 ng/ml bFGF (e.g., Uniprot #P09038 in humans), 80-120 ng/ml hSCF (e.g., Uniprot #P21583 in humans), 20-30 ng/ml Flt3 ligand (e.g., Uniprot #P36888 in humans), and 40-60 ng/ml hTPO (e.g., Uniprot #P40225 in humans), 8-12 ng/ml IL-6 (e.g., Uniprot #P05231 in humans), 0.5-2 U/ml EPOgen (e.g., Uniprot #P01588 in humans) (in some embodiments the ratio of VEGF:bFGF:hSCF:Flt3 Ligand:hTPO:IL-6 is about 5:10:10:2.5:10:1);

g) a mixture of IMDM and Hams F12 media supplemented with B27, N2-supplement, BSA, 40-60 ng/ml VEGF (e.g., Uniprot #P15692 in humans), 80-120 ng/ml bFGF (e.g., Uniprot #P09038 in humans), 80-120 ng/ml hSCF (e.g., Uniprot #P21583 in humans), 20-30 ng/ml Flt3 ligand (e.g., Uniprot #P36888 in humans), and 40-60 ng/ml hTPO (e.g., Uniprot #P40225 in humans), 8-12 ng/ml IL-6 (e.g., Uniprot #P05231 in humans), 0.5-2 U/ml EPOgen (e.g., Uniprot #P01588 in humans) (in some embodiments the ratio of VEGF:bFGF:hSCF:Flt3 Ligand:hTPO:IL-6 is about 5:10:10:2.5:10:1) and an AhR agonist.

In some embodiments a pluripotent stem cell is differentiated into a MEP in culture by a method comprising culturing in at least one culture media comprising a combination of factors, the culture media and factor combination comprising a composition selected from:

a) RPMI media supplemented with about 5 ng/ml BMP-4 (e.g., Uniprot #P12644 in humans), about 50 ng/ml VEGF (e.g., Uniprot #P15692 in humans), about 25 ng/ml Wnt3a (e.g., Uniprot #P56704 in humans), and about 10% knockout serum replacement (KOSR);

b) RPMI media supplemented with about 5 ng/ml BMP-4 (e.g., Uniprot #P12644 in humans), about 50 ng/ml VEGF (e.g., Uniprot #P15692 in humans), about 20 ng/ml bFGF (e.g., Uniprot #P09038 in humans) and about 10% KOSR;

c) StemPro 34 media supplemented with about 5 ng/ml BMP-4 (e.g., Uniprot #P12644 in humans), about 50 ng/ml VEGF (e.g., Uniprot #P15692 in humans), and about 20 ng/ml bFGF (e.g., Uniprot #P09038 in humans);

d) StemPro 34 media supplemented with about 50 ng/ml VEGF (e.g., Uniprot #P15692 in humans), and about 5 ng/ml bFGF (e.g., Uniprot #P09038 in humans);

e) a mixture of IMDM and Hams F12 media supplemented with about 1% B27, about 0.5% N2-supplement, about 0.5% BSA, about 15 ng/ml VEGF (e.g., Uniprot #P15692 in humans), about 5 ng/ml bFGF (e.g., Uniprot #P09038 in humans), about 100 ng/ml hSCF (e.g., Uniprot #P21583 in humans), and about 25 ng/ml Flt3 ligand (e.g., Uniprot #P36888 in humans);

f) a mixture of IMDM and Hams F12 media supplemented with about 1% B27, about 0.5% N2-supplement, about 0.5% BSA, about 50 ng/ml VEGF (e.g., Uniprot #P15692 in humans), about 100 ng/ml bFGF (e.g., Uniprot #P09038 in humans), about 100 ng/ml hSCF (e.g., Uniprot #P21583 in humans), about 25 ng/ml Flt3 ligand (e.g., Uniprot #P36888 in humans), about 50 ng/ml hTPO (e.g., Uniprot #P40225 in humans), about 10 ng/ml IL-6 (e.g., Uniprot #P05231 in humans), about 0.5 U/ml EPOgen (e.g., Uniprot #P01588 in humans); and g) a mixture of IMDM and Hams F12 media supplemented with about 1% B27, about 0.5% N2-supplement, about 0.5% BSA, about 50 ng/ml VEGF (e.g., Uniprot #P15692 in humans), about 100 ng/ml bFGF (e.g., Uniprot #P09038 in humans), about 100 ng/ml hSCF (e.g., Uniprot #P21583 in humans), about 25 ng/ml Flt3 ligand (e.g., Uniprot #P36888 in humans), and about 50 ng/ml hTPO (e.g., Uniprot #P40225 in humans), about 10 ng/ml IL-6 (e.g., Uniprot #P05231 in humans), about 0.5 U/ml EPOgen (e.g., Uniprot #P01588 in humans) and an AhR agonist.

In some embodiments a pluripotent stem cell is differentiated into a MEP in culture by a method comprising:

a) culturing the pluripotent stem cell in RPMI media supplemented with BMP-4, VEGF (e.g., Uniprot #P15692 in humans), Wnt3a (e.g., Uniprot #P56704 in humans), and knockout serum replacement (KOSR);

b) culturing the cell obtained from step a) in RPMI media supplemented with BMP-4 (e.g., Uniprot #P12644 in humans), VEGF (e.g., Uniprot #P15692 in humans), bFGF (e.g., Uniprot #P09038 in humans) and KOSR;

c) culturing the cell obtained from step b) in StemPro 34 media supplemented with BMP-4 (e.g., Uniprot #P12644 in humans), VEGF (e.g., Uniprot #P15692 in humans), and bFGF (e.g., Uniprot #P09038 in humans);

d) culturing the cell obtained from step c) in StemPro 34 media supplemented with VEGF (e.g., Uniprot #P15692 in humans), and bFGF (e.g., Uniprot #P09038 in humans);

e) culturing the cell obtained from step d) in a mixture of IMDM and Hams F12 supplemented with B27, N2-supplement, BSA, VEGF (e.g., Uniprot #P15692 in humans), bFGF (e.g., Uniprot #P09038 in humans), hSCF (e.g., Uniprot #P21583 in humans), and Flt3 ligand (e.g., Uniprot #P36888 in humans); and f) culturing the cell obtained from step e) in a mixture of IMDM and Hams F12 supplemented with B27, N2-supplement, BSA, VEGF (e.g., Uniprot #P15692 in humans), bFGF (e.g., Uniprot #P09038 in humans), hSCF (e.g., Uniprot #P21583 in humans), Flt3 ligand (e.g., Uniprot #P36888 in humans), and hTPO (e.g., Uniprot #P40225 in humans), IL-6 (e.g., Uniprot #P05231 in humans), EPOgen (e.g., Uniprot #P01588 in humans).

In some embodiments the culture media used in at least one of culture steps a) to e) further comprises an AhR antagonist.

In some embodiments the culture media used in step f) further comprises an AhR agonist.

In some embodiments a pluripotent stem cell is differentiated into a MEP in culture by a method comprising:

a) culturing the pluripotent stem cell in RPMI media supplemented with 4-6 ng/ml BMP-4, 40-60 ng/ml VEGF (e.g., Uniprot #P15692 in humans), 20-30 ng/ml Wnt3a (e.g., Uniprot #P56704 in humans), and 10% knockout serum replacement (KOSR)) (in some embodiments the ratio of BMP-4:VEGF:Wnt3a is about 1:10:5);

b) culturing the cell obtained from step a) in RPMI media supplemented with 4-6 ng/ml BMP-4 (e.g., Uniprot #P12644 in humans), 40-60 ng/ml VEGF (e.g., Uniprot #P15692 in humans), 16-24 ng/ml bFGF (e.g., Uniprot #P09038 in humans) and 10% KOSR (in some embodiments the ratio of BMP-4:VEGF:bFGF is about 1:10:4);

c) culturing the cell obtained from step b) in StemPro 34 media supplemented with 4-6 ng/ml BMP-4 (e.g., Uniprot #P12644 in humans), 40-60 ng/ml VEGF (e.g., Uniprot #P15692 in humans), and 16-24 ng/ml bFGF (e.g., Uniprot #P09038 in humans) (in some embodiments the ratio of BMP-4:VEGF:bFGF is about 1:10:4);

d) culturing the cell obtained from step c) in StemPro 34 media supplemented with 12-18 ng/ml VEGF (e.g., Uniprot #P15692 in humans), and 4-6 ng/ml bFGF (e.g., Uniprot #P09038 in humans) (in some embodiments the ratio of VEGF:bFGF is about 3:1);

e) culturing the cell obtained from step d) in a mixture of IMDM and Hams F12 supplemented with 1% B27, 0.5% N2-supplement, 0.5% BSA, 40-60 ng/ml VEGF (e.g., Uniprot #P15692 in humans), 80-120 ng/ml bFGF (e.g., Uniprot #P09038 in humans), 80-120 ng/ml hSCF (e.g., Uniprot #P21583 in humans), and 20-30 ng/ml Flt3 ligand (e.g., Uniprot #P36888 in humans) (in some embodiments the ratio of VEGF:bFGF:hSCF:Flt3 ligand is about 2:4:4:1); and f) culturing the cell obtained from step e) in a mixture of IMDM and Hams F12 supplemented with 1% B27, 0.5% N2-supplement, 0.5% BSA, 40-60 ng/ml VEGF (e.g., Uniprot #P15692 in humans), 80-120 ng/ml bFGF (e.g., Uniprot #P09038 in humans), 80-120 ng/ml hSCF (e.g., Uniprot #P21583 in humans), 20-30 ng/ml Flt3 ligand (e.g., Uniprot

P36888 in humans), and 40-60 ng/ml hTPO (e.g., Uniprot #P40225 in humans), 8-12 ng/ml IL-6 (e.g., Uniprot #P05231 in humans), 0.5-2 U/ml EPOgen (e.g., Uniprot #P01588 in humans) (in some embodiments the ratio of VEGF:bFGF:hSCF:Flt3 Ligand:hTPO:IL-6 is about 5:10:10:2.5:10:1).

In some embodiments the culture media used in at least one of culture steps a) to e) further comprises an AhR antagonist.

In some embodiments the culture media used in step f) further comprises an AhR agonist.

In some embodiments a pluripotent stem cell is differentiated into a MEP in culture by a method comprising:

a) culturing the pluripotent stem cell in RPMI media supplemented with 5 ng/ml BMP-4, 50 ng/ml VEGF (e.g., Uniprot #P15692 in humans), 25 ng/ml Wnt3a (e.g., Uniprot #P56704 in humans), and 10% knockout serum replacement (KOSR);

b) culturing the cell obtained from step a) in RPMI media supplemented with 5 ng/ml BMP-4 (e.g., Uniprot #P12644 in humans), 50 ng/ml VEGF (e.g., Uniprot #P15692 in humans), 20 ng/ml bFGF (e.g., Uniprot #P09038 in humans) and 10% KOSR;

c) culturing the cell obtained from step b) in StemPro 34 media supplemented with 5 ng/ml BMP-4 (e.g., Uniprot #P12644 in humans), 50 ng/ml VEGF (e.g., Uniprot #P15692 in humans), and 20 ng/ml bFGF (e.g., Uniprot #P09038 in humans);

d) culturing the cell obtained from step c) in StemPro 34 media supplemented with 15 ng/ml VEGF (e.g., Uniprot #P15692 in humans), and 5 ng/ml bFGF (e.g., Uniprot #P09038 in humans);

e) culturing the cell obtained from step d) in a mixture of IMDM and Hams F12 supplemented with 1% B27, 0.5% N2-supplement, 0.5% BSA, 50 ng/ml VEGF (e.g., Uniprot #P15692 in humans), 100 ng/ml bFGF (e.g., Uniprot #P09038 in humans), 100 ng/ml hSCF (e.g., Uniprot #P21583 in humans), and 25 ng/ml Flt3 ligand (e.g., Uniprot #P36888 in humans); and f) culturing the cell obtained from step e) in a mixture of IMDM and Hams F12 supplemented with 1% B27, 0.5% N2-supplement, 0.5% BSA, 50 ng/ml VEGF (e.g., Uniprot #P15692 in humans), 100 ng/ml bFGF (e.g., Uniprot #P09038 in humans), 100 ng/ml hSCF (e.g., Uniprot #P21583 in humans), 25 ng/ml Flt3 ligand (e.g., Uniprot #P36888 in humans), and 50 ng/ml hTPO (e.g., Uniprot #P40225 in humans), 10 ng/ml IL-6 (e.g., Uniprot #P05231 in humans), and 0.5 U/ml EPOgen (e.g., Uniprot #P01588 in humans).

In some embodiments the culture media used in at least one of culture steps a) to e) further comprises an AhR antagonist.

In some embodiments the culture media used in step f) further comprises an AhR agonist.

In some embodiments, prior to step a), pluripotent stem cells are cultured in iPSC media conditioned on MEFs for 24 hours and supplemented with Rho Kinase Inhibitor and bFGF.

In some embodiments MEPs made by these or other methods disclosed herein are isolated.

In some embodiments step a) is for a period of about 2 days, step b) is for a period of about 1 day, step c) is for a period of about 1 day, step d) is for a period of about 2 days, step e) is for a period of about 1 day, and step f) is for a period of about 1 day. In some embodiments the cells are further cultured in the media of step f) for a period of: from 1 to 2 days, from 2 to 4 days, from 3 to 6 days, 1 to 2 weeks, from 2-4 weeks, and from 4-8 weeks. In some embodiments the cells are further cultured in the media of step f) for a period of: at least 24 hours, at least 36 hours, at least 2 days, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, and at least 8 weeks. In some embodiments the cells are further cultured in the media of step f) for at least 3 months, at least 6 months, at least 1 year, or indefinitely. In some embodiments the cell culture of step f) is split and frozen stocks are created. Such stocks may be thawed periodically to provide an indefinite supply of a cell culture that forms differentiated MEP cells.

In some embodiments of the methods of this disclosure a culture of pluripotent stem cells begins to differentiate MEPs within 7 to 10 days. In some embodiments the culture will continue to produce MEPs for at least 30 days. If during that process the cultured cells are grown in media comprising an AhR agonist.

In some embodiments the culture does not comprise serum. In some embodiments the culture does not comprise feeder cells. This feeder-free aspect of such embodiments provides certain advantages in certain situations. For example, in some such embodiments it reduces the risk of contamination of the resultant MEPs, which reduces the risk of contamination of red blood cells or platelets made from such MEPs. This reduced risk can be desirable in certain applications of the cells.

In some embodiments the proteins used in the protocols in this section D are modified derivatives and/or muteins of naturally occurring proteins. In some embodiments the protein used are at least 70%, at least 80%, at least 85%, at least 90%, at least 91%, at least 92%, at least 93%, at least 94%, at least 95%, at least 96%, at least 97%, at least 98%, at least 99%, or at least 99.5%, identical to the protein sequence identified by the Uniprot or other database ID number identified herein.

In some embodiments the methods comprise providing an iPSC and differentiating the iPSC into a MEP. In some embodiments the methods comprise providing a hemangioblast and differentiating the hemangioblast into a MEP. In some embodiments the methods comprise providing a HSC and differentiating the HSC into a MEP. In some embodiments the methods comprise providing a CMP and differentiating the CMP into a MEP. In some embodiments differentiating into a MEP comprises culturing in an AhR antagonist. In some embodiments differentiating into a MEP comprises culturing in an AhR agonist. In some embodiments differentiating into a MEP comprises culturing in an AhR antagonist and culturing in an AhR agonist. In some embodiments differentiating into a MEP comprises culturing in an AhR antagonist for a first period of time and then culturing in an AhR agonist for a second period of time.

E. Methods of Making Red Blood Cells

MEPs, including those produced by the methods of this disclosure, have the potential to differentiate into red blood cells. Accordingly, this disclosure also provides methods of making red blood cells, comprising providing a MEP and culturing the MEP under conditions sufficient to make a red blood cell. In some embodiments the methods comprise making a MEP according to a method of this disclosure and culturing the MEP under conditions sufficient to make a red blood cell. In some embodiments, the methods sufficient to make a RBC comprise culturing the MEP in the presence of an AhR agonist. In some embodiments the conditions sufficient to make a RBC comprise culturing in erythroid specification media. In still further embodiments, the conditions sufficient to make a RBC comprise culturing in erythroid specification media and in the presence of an AhR agonist. In some embodiments erythroid specification media comprises EPO. (EPO can be from any suitable source known in the art, such as R&D (Catalog #286-EP) or Amgen (EPOgen) commercially, for example. Erythropoietin has its primary effect on red blood cell progenitors and precursors (which are found in the bone marrow in humans) by promoting their survival through protecting these cells from apoptosis to promote definitive erythropoiesis. Erythropoietin is the primary erythropoietic factor that cooperates with various other growth factors (IL-3, IL-6, Glucocorticoids, SCF) involved in the development of erythroid lineage from multipotent progenitors. In some embodiments of this disclosure erythroid specification media comprises EPO. In some embodiments of this disclosure erythroid specification media comprises at least one additional factor selected from IL-3, IL-6, Glucocorticoids, and SCF. Because the MEPs produced by the methods disclosed herein can be transported and can even be frozen, stored and/or transported, this disclosure also enables the distribution of MEPs made by a method of the disclosure to a different location and/or to a different user, who can then in turn make red blood cells from the MEPs. Accordingly, this disclosure also provides methods of making red blood cells, comprising providing a MEP differentiated in vitro using a method of this disclosure, and culturing the MEP under conditions sufficient to make a RBC. In some embodiments, the methods sufficient to make a RBC comprise culturing the MEP in the presence of an AhR agonist. In some embodiments the conditions sufficient to make a RBC comprise culturing in erythroid specification media. In still further embodiments, the conditions sufficient to make a RBC comprise culturing in erythroid specification media and in the presence of an AhR agonist. In some embodiments erythroid specification media comprises EPO.

In some embodiments alternative methods of making red blood cells known in the art are modified to comprise culturing cells in the presence of a AhR agonist to make red blood cells. One exemplary method is that disclosed in Feng Ma et. al, PNAS, Sep. 2, 2008, vol. 105, no. 35, p 13087-13092. Ma et. al utilize a murine fetal liver stromal cell (mFLSC) layer to differentiate human embryonic stem cells (hESC) into terminally mature red blood cells. The mFLSC layer was prepared from embryonic D15 Black 6 mice, expanded and irradiated. hESC were passaged onto wells containing the mFLSC on gelatin and grown in 3 mL of media (α-MEM, 15% FBS, 1 mM glutamine, 1% nonessential amino acids) which was changed every 3 days. From this culture non-adherent cells were produced and collected on various days. These cells where analyzed by RT-PCR for erythroid gene expression, by immunofluorescence for hemoglobin expression, and by colony culture for differentiation potential. They found that their cells began expressing erythroid markers as early as day 4 in co-culture and increased expression over time, final time point D18. β-globin protein expression was detected in individual cells by immunofluorescence starting and increasing in number from Day 12-18. Further maturation was seen using colony and suspension culture. Cells from the co-culture were plated in 1.2% methylcellulose containing 30% FBS, 1% deionized fraction V BSA, 0.1 mM 2-mercaptoethanol, α-MEM, and a human cytokine mixture (100 ng/mL SCF, 10 ng/mL IL-3, 100 ng/mL IL-6, 10 ng/mL TPO, 10 ng/mL G-CSF, and 4 U/mL EPO). After 12-14 days erythroid bursts were harvested and grown in a suspension culture of 15% FBS, 0.1 mM 2-mercaptoethanol, α-MEM, and the human cytokine mixture listed above. These cells were analyzed as above for hemoglobins (immunostaining), enucleation (May-Grunwald-Giemsa staining), oxygen dissociation (hemox anaylzer), and glucose-6-phosphate dehydrogenase activity. They found that these cells were capable of enucleation and had increased expression of β-globin protein compared to just the co-culture generated cells. These cells bound to oxygen and had similar glucose-6-phosphate dehydrogenase activity as cord blood red blood cells. Overall, Ma et. al is able to show that by utilizing a mFLSC co-culture followed by erythroid maturation in colony and suspension culture enucleated red blood cells expression β-globin can be generated from hESC. In some embodiments the method of Ma et al. is modified to comprise culturing in the presence of an AhR agonist to produce red blood cells from embryonic stem cells.

Another exemplary method is that disclosed in Giarratana et. al, Blood, Nov. 10, 2011, vol. 118, no. 19, p 5071-5079. In this paper Giarratana et. al uses CD34+ cells obtained from human donors to show the feasibility of cell expansion and use for transfusions. In order to expand and cause cellular maturation the authors utilize a 3-step approach. CD34+ cells are obtained from leukopheresis following bone marrow stimulation with GM-CSF and CSF. These cells are cultured in EDM (IMDM, 330 ug/ml holo-transferrin, 10 ug/mL rh insulin, 2 U/mL heparin, 5% inactivated human plasma) with various cytokines are different stages. In stage 1 (days 0-7) EDM is supplemented with hydrocortisone, 100 ng/mL SCF, 5 ng/mL IL-3, and 3 U/mL EPO. The cells were then harvested and resuspened in stage 2 (days 7-11) media EDM plus 100 ng/mL SCF and 3 U/mL EPO. On day 11 the cells were once again harvested and resuspended for stage 3 (days 11-18) with EDM media supplemented with 3 U/mL of EPO. This methodology allows for cell expansion and maturation of CD34+ cells into reticulocytes. The authors compare their cultured red blood cells (cRBCs) with cord blood and adult blood red blood cells for oxygen binding, glucose-6-phosphate dehydrogenase and pyruvate kinase activity, and ability of cells to deform. Their cRBCs behaved very similarly to cord blood RBCs. Upon putting the cRBC in vivo (mouse or human) the cells are capable of complete maturation as determined by loss of CD71 expression, organelles, and surface area. They also saw the cells demonstrate a biconcave shape. cRBCs can be stored for normal time frame (4 weeks) without loss of RBC characteristics. In some embodiments the method of Giarratana et al. is modified to comprise culturing in the presence of an AhR agonist to produce red blood cells from CD34+ cells.

The methods disclosed herein also enable making a red blood cell from any MEP from any source. For example, the MEP can be obtained from bone marrow of a donor. In some embodiments the MEP is first isolated from other cells present in the bone marrow by, for example, FACS. Alternatively, the whole bone marrow or a fraction thereof can be cultured and MEP cell formation stimulated by culturing in the presence of an AhR agonist. Accordingly, also provided herein are methods of making a red blood cell comprising culturing a MEP in the presence of an AhR agonist. In some embodiments the methods further comprise culturing the MEP in erythroid specification media.

In some embodiments RBCs made by these or other methods disclosed herein are isolated. In some embodiments the RBCs are formulated for administration to a mammal.

F. Methods of Making Megakaryocytes

MEPs, including those produced by the methods of this disclosure, have the potential to differentiate into megakaryocytes (Mks). Accordingly, this disclosure also provides methods of making megakaryocytes, comprising making a MEP according to a method of this disclosure, and culturing the MEP under conditions sufficient to make a Mk. In some embodiments the conditions sufficient to make a Mk comprise culturing the MEP in the presence of an AhR modulator. In some embodiments the AhR modulator is an AhR antagonist. In some embodiments the conditions sufficient to make a Mk comprise culturing the MEP in megakaryocyte specification media. In still further embodiments, the conditions sufficient to make a Mk comprise culturing in megakaryocyte specification media and in the presence of an AhR modulator. In still further embodiments, the conditions sufficient to make a Mk further comprise culturing the MEP in the presence of an AhR agonist and then culturing in the presence of an AhR antagonist. In some embodiments this process causes an increase in the total numbers of Mks produced compared to methods that comprise only culturing in an AhR agonist or only culturing in an AhR antagonist. In some embodiments the AhR modulator is an AhR antagonist. In some embodiments megakaryocyte specification media comprises TPO (for example, Uniprot #P40225 in humans). Human TPO can be acquired commercially from R&D (Catalog #288-TP) or Genentech (Catalog #G140BT), for example. In some embodiments megakaryocyte specification media further comprises stromal derived factor 1 (SDF1).

In some embodiments alternative methods of making Mks known in the art are modified to comprise culturing cells in the presence of a AhR modulator to make Mks and/or platelets. In some embodiments the AhR modulator is an AhR antagonist Previously reported differentiation protocols for human megakaryopoeisis have isolated pluripotent stem cells or human bone marrow for in vitro expansion. Bone marrow protocols start with the collection of mononuclear cells from the femur of human subjects in defined culture conditions (Schattner, M. et al. Thrombopoietin-stimulated ex vivo expansion of human bone marrow megakaryocytes. *Stem Cells.* 14, 207-214. (1996). Following in vitro culture and expansion, these cells are sorted using magnetic cell sorting such that the progenitor pool (CD34+) fraction is isolated and used as source material for megakaryocyte differentiation. These cells are plated on human or murine irradiated bone marrow stroma that serve as a substrate for adhesion and an aid in megakaryocyte maturation for the CD34+ population. These cultures are grown in media containing human serum and various permutations of cytokine cocktails containing thrombopoietin (TPO), stem cell factor (SCF), and Interleukin-3 (IL-3). In the seminal report of this protocol, megakaryocyte populations, as defined by the protein-level expression of CD41a, were observed as early as 12 days post-plating. In some embodiments the method of Schattner et al. is modified to comprise culturing in the presence of an AhR antagonist to produce red blood cells from CD34+ cells.

Protocols for differentiating Mks from human pluripotent stem cells (ESC or iPSC) may also be modified to comprise culturing in the presence of an AhR modulator. In some embodiments the AhR modulator is an AhR antagonist. For example, recent work has proved efficient in optimizing differentiation protocols that use human ES or iPS cells as source material. (Gaur, M. et al. Megakaryocytes derived from human embryonic stem cells: a genetically tractable system to study megakaryocytopoiesis and integrin function. *J Thromb Haemost.* 4, 436-442. (2006).) The key differences with this approach are the added technical complications associated with proper maintenance and passage of pluripotent cells as well as the challenge of concocting cytokine cocktails that are amenable to inducing hematopoiesis. Gaur et al. solved these issues by using similar strategies as bone marrow protocols. Namely, ESCs were plated on bone marrow stroma and subjected to a high dose of TPO. After 7 days, large colonies thought to contain hematopoietic progenitors were physically disrupted in order to isolate the progenitor pool in a single-cell suspension. The cells were plated on a fresh stromal monolayer and kept in high TPO media until splitting at day 11, which involved a prolonged exposure to trypsin and collagenase, again, to isolate these cells in suspension as best as possible. The cells were again replated and found to express megakaryocyte markers and exhibit high ploidy as early as day 15. In some embodiments the method of Gaur et al. is modified to comprise culturing in the presence of an AhR modulator to produce red blood cells from human pluripotent stem cells. In some embodiments the AhR modulator is an AhR antagonist.

Because the MEPs produced by the methods disclosed herein can be transported and can even be frozen, stored and/or transported, this disclosure also enables the distribution of MEPs made by a method of the disclosure to a different location and/or to a different user, who can then in turn make megakaryocytes from the MEPs. Accordingly, this disclosure also provides methods of making megakaryocytes, comprising providing a MEP differentiated in vitro using a method of this disclosure, and culturing the MEP under conditions sufficient to make a megakaryocyte. In some embodiments, the methods sufficient to make a megakaryocyte comprise culturing the MEP in the presence of an AhR modulator. In some embodiments the AhR modulator is an AhR antagonist. In some embodiments the conditions sufficient to make a megakaryocytes comprise culturing in megakaryocyte specification media. In still further embodiments, the conditions sufficient to make a megakaryocyte comprise culturing in megakaryocyte specification media and in the presence of an AhR modulator. In some embodiments the AhR modulator is an AhR antagonist. In some embodiments megakaryocyte specification media comprises TPO.

The methods disclosed herein also enable making a megakaryocyte from any MEP from any source. For example, the MEP can be obtained from bone marrow of a donor. In some embodiments the MEP is first isolated from other cells present in the bone marrow by, for example FACS. Alternatively, the whole bone marrow or a fraction thereof can be cultured and MEP cell formation stimulated by culturing in the presence of an AhR agonist. Accordingly, also provided herein are methods of making a megakaryocyte comprising culturing a MEP from any source in the presence of an AhR modulator. In some embodiments the AhR modulator is an AhR antagonist. In some embodiments the methods further comprise culturing the MEP in megakaryocyte specification media.

In some embodiments Mks made by these or other methods disclosed herein are isolated. In some embodiments the Mks are formulated for administration to a mammal.

G. Methods of Making Platelets

MEPs, including those produced by the methods of this disclosure, have the potential to differentiate into megakaryocytes, which in turn will naturally differentiate in culture to form platelets. Accordingly, this disclosure also provides methods of making platelets, comprising making a MEP according to a method of this disclosure, culturing the MEP under conditions sufficient to make a Mk, and culturing the Mk under conditions sufficient for differentiation of a platelet from the Mk. In some embodiments the conditions sufficient to make a Mk comprise culturing the MEP in the presence of an AhR modulator. In some embodiments the AhR modulator is an AhR antagonist. In some embodiments the conditions sufficient to make a Mk further comprise culturing the MEP in the presence of an AhR agonist and then culturing in the presence of an AhR antagonist. In some embodiments the conditions sufficient to make a Mk comprise culturing the MEP in megakaryocyte specification media. In still further embodiments, the conditions sufficient to make a Mk comprise culturing in megakaryocyte specification media and in the presence of an AhR modulator. In some embodiments the AhR modulator is an AhR antagonist. In some embodiments megakaryocyte specification media comprises TPO.

Because the MEPs produced by the methods disclosed herein can be transported and can even be frozen, stored and/or transported, this disclosure also enables the distribution of MEPs made by a method of the disclosure to a different location and/or to a different user, who can then in turn make platelets from the MEPs. Accordingly, this disclosure also provides methods of making platelets, comprising providing a MEP differentiated in vitro using a method of this disclosure, culturing the MEP under conditions sufficient to make a megakaryocyte, and culturing the Mk under conditions sufficient for differentiation of a platelet from the Mk. In some embodiments, the methods sufficient to make a megakaryocyte comprise culturing the MEP in the presence of an AhR modulator. In some embodiments the AhR modulator is an AhR antagonist. In some embodiments the conditions sufficient to make a Mk further comprise culturing the MEP in the presence of an AhR agonist and then culturing in the presence of an AhR antagonist. In some embodiments the conditions sufficient to make a megakaryocytes comprise culturing in megakaryocyte specification media. In still further embodiments, the conditions sufficient to make a megakaryocyte comprise culturing in megakaryocyte specification media and in the presence of an AhR modulator. In some embodiments the AhR modulator is an AhR antagonist. In some embodiments megakaryocyte specification media comprises TPO.

The methods disclosed herein also enable making a megakaryocyte from any MEP from any source and thus also allow making a platelet from any MEP source. For example, the MEP can be obtained from bone marrow of a donor. In some embodiments the MEP is first isolated from other cells present in the bone marrow by, for example FACS. Alternatively, the whole bone marrow or a fraction thereof can be cultured and MEP cell formation stimulated by culturing in the presence of an AhR agonist. Accordingly, also provided herein are methods of making a platelet comprising culturing a MEP in the presence of an AhR modulator to make a Mk and culturing the Mk under conditions sufficient for differentiation of a platelet. In some embodiments the AhR modulator is an AhR antagonist. In some embodiments the conditions sufficient to make a Mk further comprise culturing the MEP in the presence of an AhR agonist and then culturing in the presence of an AhR antagonist. In some embodiments the methods further comprise culturing the MEP in megakaryocyte specification media.

In some embodiments platelets made by these or other methods disclosed herein are isolated. In some embodiments the Mks are formulated for administration to a mammal.

H. Aryl Hydrocarbon Receptor (AhR) Modulators

The Aryl Hydrocarbon Receptor ("AhR") is a ligand-activated member of the family of basic-helix-loop-helix transcription factors that has been found to be activated by numerous structurally diverse synthetic and naturally occurring compounds, such as poly cyclic aromatic hydrocarbons, indoles, and flavonoids. In the absence of bound ligand, the AhR is present in a latent conformation in the cytoplasmic compartment of the cell associated with two molecules of the molecular chaperone heat shock protein 90, an immunophilin-like protein, XAP2, and the hsp90 interacting protein p23. Ligand binding initiates a cascade of events that includes translocation to the nucleus, release of hsp90, and heterodimerization with ARNT and other transcription factor monomers. The ligand bound AhR-ARNT complex is capable of recognizing consensus sequences termed dioxin-response elements ("DRE" s) located in the promoter region of CYP1A1 and other responsive genes, thereby activating transcription. Known examples of AhR-associated proteins include, but are not limited to, hsp90 p23, XAP2, p60, hsp70, p48, RelB, and estrogen receptor.

The AhR protein contains several domains critical for function and is classified as a member of the basic helix-loop-helix/Per-Arnt-Sim (bHLH/PAS) family of transcription factors. The bHLH motif is located in the N-terminal of the protein. Members of the bHLH superfamily have two functionally distinctive and highly conserved domains. The first is the basic-region (b) which is involved in the binding of the transcription factor to DNA. The second is the helix-loop-helix (HLH) region which facilitates protein-protein interactions. Also contained with the AhR are two PAS domains, PAS-A and PAS-B, which are stretches of 200-350 amino acids that exhibit a high sequence homology to the protein domains that were originally found in the *Drosophila* genes period (Per) and single minded (Sim) and in AhR's dimerization partner, the aryl hydrocarbon receptor nuclear translocator (ARNT). The PAS domains support specific secondary interactions with other PAS domain containing proteins, as is the case with AhR and ARNT, so that heterozygous and homozygous protein complexes can form. The ligand binding site of AhR is contained within the PAS-B domain and contains several conserved residues critical for ligand binding. Finally, a Q-rich domain is located in the C-terminal region of the protein and is involved in co-activator recruitment and transactivation.

As used herein, "AhR" or "Aryl Hydrocarbon Receptor" refers to any protein commonly understood to be a AhR or Aryl Hydrocarbon Receptor from any mammal, as well as variants and modified derivatives thereof. In some embodiments the AhR is the human protein identified by Genbank identifier NP_001612, which is hereby incorporated herein by reference.

During canonical signaling, cytosolic AhR binds to a ligand, such as a suitable small molecule, which facilitates AhR translocation to the nucleus and eventually results in de novo transcription of target genes. The promoters of AhR target genes have the responsive element 5'-TNGCGTG-3', termed "AhR response element" or "AHRE" or "Drug response element" or "DRE", or "Xenobiotic response element" or "XRE". The genes for xenobiotic-metabolizing enzymes (e.g., cytochrome P450) are well-known targets of AhR. Hundreds of other genes also have AHREs. Elucidation of the biochemistry of canonical AhR signaling has revealed several parameters that can fine-tune AhR activity. These include ligand characteristics, adapter molecules and transcriptional co-activators or co-repressors that regulate the extraordinary cell-specific activity of AhR.

The AhR modulator may be any substance, including without limitation a peptide, a polypeptide, a protein (such as for example an antibody or antibody fragment), a nucleotide, an oligonucleotide, a polynucleotide, a lipid, a sugar, or a naturally occurring or non-naturally occurring derivative thereof. The AhR modulator, whether it also fits within one or more of the previously listed classes, may be a small organic molecule or a complex organic molecule.

Molecules with AhR agonist and antagonist activity are well known in the art and may be used in the methods of this disclosure. (See for example Denison, M. S., and S. R. Nagy. 2003, "Activation of the aryl hydrocarbon receptor by structurally diverse exogenous and endogenous chemicals," *Annu Rev Pharmacol Toxicol* 43:309-334; and Nguyen, L. P., and C. A. Bradfield, 2008, "The search for endogenous activators of the aryl hydrocarbon receptor," *Chemical research in toxicology* 21:102-116).

One type of assay that may be used to characterize the activity of such molecules or to identify new molecules is an in vitro cell based assay. In one example, the H1G1 mouse hepatoma line is stably transfected with an AhR-driven, green fluorescent protein reporter. Suspected AhR ligands are added to H1G1 cultures at tittered concentrations for 18-48 hours. GFP fluorescence is then quantified in a Luminometer. AhR antagonist activity is determined by assaying GFP fluorescence in H1G1 cells following addition of both the compound of interest and a known AhR ligand, e.g., β-napthoflavone (BNF). Examples of such assays are described, for example, in Nagy, S. R., et al., 2002, "Identification of novel Ah receptor agonists using a high-throughput green fluorescent protein-based recombinant cell bioassay," *Biochemistry* 41:861-868; and Nagy, S. R., et al., 2002, "Development of a green fluorescent protein-based cell bioassay for the rapid and inexpensive detection and characterization of ah receptor agonists," *Toxicol Sci* 65:200-210, each of which is hereby incorporated herein by reference for all purposes. See also Garrison et al., 1996, "Species-specific recombinant cell lines as bioassay systems for the detection of 2,3,7,8-tetrachlorodibenzo-p-dioxin-like chemicals," Fundamental and Applied Toxicology, 30:194-203, which is hereby incorporated herein by reference for all purposes.

An exemplary assay that may be used to characterize AhR agonist activity of a test agent is to provide a cell culture comprising MEPs and then culture the cell culture in the presence of EPO and the test agent and measure production of RBCs in the culture. At least one control culture may optionally be conducted and/or the results of at least one control cell culture may be referenced. The optional control culture will typically be a culture in which a similar cell culture comprising MEPs is cultured in the presence of EPO but not the test agent. Alternatively, or in addition, a control cell culture may be conducted or referenced, in which a similar cell culture comprising MEPs is cultured in the presence of EPO and a known AhR agonist, such as FICZ. By assaying for production of RBCs in the cell culture comprising EPO and the test agent, and optionally comparing production of RBCs in that culture to production of RBCs in at least one of the control cell cultures it is determined whether the test agent has AhR agonist activity. The test agent is determined by this assay to have AhR agonist activity if, for example, production of RBCs by the culture comprising the test agent and EPO produces more RBCs than a control culture comprising EPO but not the test agent.

An exemplary assay that may be used to characterize AhR antagonist activity of a test agent is to provide a cell culture comprising MEPs and then culture the cell culture in at least one of 1) the cell culture comprising EPO and the test agent; and 2) the cell culture comprising EPO, a known AhR agonist, and the test agent. At least one control culture may optionally be conducted and/or the results of at least one control cell culture may be referenced. The optional control culture will typically be a culture in which a similar cell culture comprising MEPs is cultured in the presence of EPO but not the test agent, or the presence of EPO and the known AhR agonist. By assaying for production of RBCs in the at least one of 1) the cell culture comprising EPO and the test agent; and 2) the cell culture comprising EPO, the known AhR agonist, and the test agent; and optionally comparing production of RBCs in the at least one culture to production of RBCs in the at least one control cell culture, it is determined whether the test agent has AhR antagonist activity. The test agent is determined by this assay to have AhR antagonist activity if, for example, production of RBCs by at least one of 1) the cell culture comprising EPO and the test agent; and 2) the cell culture comprising EPO, a known AhR agonist, and the test agent, produces fewer RBCs than a control culture comprising EPO but not the test agent, and/or fewer RBCs than a control culture comprising EPO and the known AhR agonist but not the test agent.

Another exemplary assay that may be used to characterize AhR antagonist activity of a test agent is to provide a cell culture comprising MEPs and then culture the cell culture in the presence of TPO and the test agent and measure production of Mks and/or platelets in the culture. At least one control culture may optionally be conducted and/or the results of at least one control cell culture may be referenced. The optional control culture will typically be a culture in which a similar cell culture comprising MEPs is cultured in the presence of TPO but not the test agent. Alternatively, or in addition, the control cell culture will be a culture in which a similar cell culture comprising MEPs is cultured in the presence of TPO and a known AhR agonist, such as FICZ. By assaying for production of Mks and/or platelets in the cell culture comprising TPO and the test agent, and optionally comparing production of Mks and/or platelets in that culture to production of Mks and/or platelets in at least one of the control cell cultures it is determined whether the test agent has AhR antagonist activity. The test agent is determined by this assay to have AhR antagonist activity if, for example, production of Mks and/or platelets by the culture comprising the test agent and TPO produces more Mks and/or platelets than a control culture comprising TPO but not the test agent, and/or more Mks and/or platelets than a control culture comprising TPO and the known AhR agonist but not the test agent.

In addition, standard physiological, pharmacological and biochemical procedures are available for testing agents to identify those that possess biological activities that modulate the activity of the AhR. Such assays include, for example, biochemical assays such as binding assays, fluorescence polarization assays, FRET based coactivator recruitment assays (see generally Glickman et al., J. Biomolecular Screening, 7 No. 1 3-10 (2002)), as well as cell based assays including the co-transfection assay, the use of LBD-Gal 4 chimeras, protein-protein interaction assays (see, Lehmann. et al., J. Biol Chem., 272(6) 3137-3140 (1997), and gene expression assays.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps can be used for high throughput screening systems and include biochemical assays such as fluorescence polarization assays (see for example, Owicki, J., Biomol Screen 2000 October; 5(5):297) scintillation proximity assays (SPA) (see for example, Carpenter et al., Methods Mol Biol 2002; 190:31-49) and fluorescence resonance energy transfer energy transfer (FRET) or time resolved FRET based coactivator recruitment assays (Mukherjee et al., J Steroid Biochem Mol Biol 2002 July; 81(3):217-25; (Zhou et al., Mol Endocrinol. 1998 October; 12(10):1594-604). Generally such assays can be performed using either the full length receptor, or isolated ligand binding domain (LBD).

If a fluorescently labeled ligand is available, fluorescence polarization assays provide a way of detecting binding of agents to the AhR by measuring changes in fluorescence polarization that occur as a result of the displacement of a trace amount of the label ligand by the agent.

The ability of an agent to bind to AhR can also be measured in a homogeneous assay format by assessing the degree to which the agent can compete off a radiolabelled ligand with known affinity for the receptor using a scintillation proximity assay (SPA). In this approach, the radioactivity emitted by a radiolabelled agent generates an optical signal when it is brought into close proximity to a scintillant such as a Ysi-copper containing bead, to which the AhR is bound. If the radiolabelled agent is displaced from the AhR the amount of light emitted from the AhR bound scintillant decreases, and this can be readily detected using standard microplate liquid scintillation plate readers such as, for example, a Wallac MicroBeta reader.

DNA binding assays can be used to evaluate the ability of an agent to modulate AhR activity. These assays measure the ability of nuclear receptor proteins, including AhR, to bind to regulatory elements of genes known to be modulated by AhR. In general, the assay involves combining a DNA sequence which can interact with the AhR, and the AhR protein under conditions, such that the amount of binding of the AhR protein in the presence or absence of the agent can be measured. In the presence of an agonist, AhR binds to the regulatory element. Methods including, but not limited to DNAse footprinting, gel shift assays, and chromatin immunoprecipitation can be used to measure the amount of AhR proteins bound to regulatory elements.

In general, a molecule identified as binding to the AhR using one of these binding assays may be identified directly in the assay as an agonist or antagonist of AhR, or may be further evaluated, in a cell-based assay for example, to determine whether the binding agent is an agonist or antagonist.

In addition a variety of cell based assay methodologies may be successfully used in screening assays to identify and profile the specificity of agents described herein. These approaches include the co-transfection assay, translocation assays, and gene expression assays.

Three basic variants of the co-transfection assay strategy exist, co-transfection assays using full-length AhR, co-transfection assays using chimeric AhRs comprising the ligand binding domain of the AhR fused to a heterologous DNA binding domain, and assays based around the use of the mammalian two hybrid assay system.

The basic co-transfection assay is based on the co-transfection into the cell of an expression plasmid to express the AhR in the cell with a reporter plasmid comprising a reporter gene whose expression is under the control of DNA sequence that is capable of interacting with that nuclear receptor. Treatment of the transfected cells with an agonist for the increases the transcriptional activity of that receptor which is reflected by an increase in expression of the reporter gene, which may be measured by a variety of standard procedures.

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase immediately downstream from the herpes virus thymidine kinase promoter (located at nucleotides residues-105 to +51 of the thymidine kinase nucleotide sequence) which is linked in turn to the various response elements.

Numerous methods of co-transfecting the expression and reporter plasmids are known to those of skill in the art and may be used for the co-transfection assay to introduce the plasmids into a suitable cell type. Typically such a cell will not endogenously express AhR that interact with the response elements used in the reporter plasmid.

Numerous reporter gene systems are known in the art and include, for example, alkaline phosphatase Berger, J., et al (1988) Gene 66 1-10; Kain, S. R. (1997) Methods. Mol. Biol. 63 49-60), 13-galactosidase (See, U.S. Pat. No. 5,070,012, issued Dec. 3, 1991 to Nolan et al., and Bronstein, I., et al., (1989) J. Chemilum. Biolum. 4 99-111), chloramphenicol acetyltransferase (See Gorman et al., Mol Cell Biol. (1982) 2 1044-51), 13-glucuronidase, peroxidase, 13-lactamase (U.S. Pat. Nos. 5,741,657 and 5,955,604), catalytic antibodies, luciferases (U.S. Pat. Nos. 5,221,623; 5,683,888; 5,674,713; 5,650,289; 5,843,746) and naturally fluorescent proteins (Tsien, R. Y. (1998) Annu. Rev. Biochem. 67 509-44).

The use of chimeras comprising the ligand binding domain (LBD) of the AhR to a heterologous DNA binding domain (DBD) expands the versatility of cell based assays by directing activation of the AhR in question to defined DNA binding elements recognized by defined DNA binding domain (see WO95/18380). This assay expands the utility of cell based co-transfection assays in cases where the biological response or screening window using the native DNA binding domain is not satisfactory.

In general, the methodology is similar to that used with the basic co-transfection assay, except that a chimeric construct is used in place of the full-length AhR. As with the full-length AhR, treatment of the transfected cells with an agonist for the AhR LBD increases the transcriptional activity of the heterologous DNA binding domain which is reflected by an increase in expression of the reporter gene as described above. Typically for such chimeric constructs, the DNA binding domains from defined AhRs, or from yeast or bacterially derived transcriptional regulators such as members of the GAL 4 and Lex A/UmuD super families are used.

A third cell based assay of utility for screening agents is a mammalian two-hybrid assay that measures the ability of the nuclear receptor to interact with a cofactor in the presence of a ligand. (See for example, U.S. Pat. Nos. 5,667,973, 5,283,173 and 5,468,614). The basic approach is to create three plasmid constructs that enable the interaction of the AhR with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the AhR fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the AhR-VP16 fusion protein can bind to the GAL4-interacting protein fusion protein bringing the strong transcriptional activator VP16 in close proximity to the GAL4-binding sites and minimal promoter region of the reporter gene. This interaction significantly enhances the transcription of the reporter gene, which can be measured for various reporter genes as described above. Transcription of the reporter gene is thus driven by the interaction of the interacting protein and AhR in a ligand dependent fashion.

An agent can be tested for the ability to induce nuclear localization of a nuclear protein receptor, such as AhR. Upon binding of an agonist, AhR translocates from the cytoplasm to the nucleus. Microscopic techniques can be used to visualize and quantitate the amount of AhR located in the nucleus. In some embodiments, this assay utilizes a chimeric AhR fused to a fluorescent protein. Nuclear AhR can also be quantified by western blotting using AhR-specific antibody and nuclear protein extracts.

An agent can also be evaluated for its ability to increase or decrease the expression of genes known to be modulated by the AhR in vivo, using Northern-blot, RT PCR, oligonucleotide microarray analysis, or high density cDNA sequencing to analyze RNA levels. Western-blot analysis can be used to measure expression of proteins encoded by AhR target genes. Expression of the CYP1B1 gene is modulated by AhR. Additional genes known to be regulated by the AhR include CYP1A1, CYP1A2, TIPARP, ALDH1 or ALDH3, TGF-b, VAV3, IL-18, PROM1, EREG, c-myc, EGR1, GSTA1, SFXN1, and NQO1.

Any agent which is a candidate for modulation of the AhR may be tested by the methods described above. Generally, though not necessarily, agents are tested at several different concentrations and administered one or more times to optimize the chances that activation of the receptor will be detected and recognized if present. Typically assays are performed in triplicate, for example, and vary within experimental error by less than about 15%. Each experiment is typically repeated about three or more times with similar results.

In some embodiments, the effects of agents and compositions on AhR gene expression can be evaluated in animals. After the administration of agents, various tissues can be harvested to determine the effect of agents on activities directly or indirectly regulated by AhR.

In some embodiments the AhR modulator is an AhR antagonist. Non-limiting examples of molecules with AhR antagonist activity that may be used in the methods of this disclosure include:
α-napthoflavone;
1,4-dihydroxyanthraquinone (quinizarin);
1,5-dihydroxyanthraquinone (anthrarufin);
1,8-dihydroxyanthraquinone (danthron);
galangin;
resveratrol;
2-methyl-2H-pyrazole-3-carboxylic acid (2-methyl-4-o-tolylazo-phenyl)-amide (also known as "CH-223191");
4-(2-(2-(benzo[b]thiophen-3-yl)-9-isopropyl-9H-purin-6-ylamino)ethyl)phenol (also known as "SR1");
N-[2-(3H-indol-3-yl)ethyl]-9-isopropyl-2-(5-methyl-3-pyridyl)purin-6-amine (also known as "GNF351");
2-(29-amino-39-methoxyphenyl)-oxanaphthalen-4-one (also known as "PD98059");
(Z)-3-[(2,4-dimethylpyrrol-5-yl)methylidenyl]-2-indolinone (also known as "TSU-16");
2-(29-amino-39-methoxyphenyl)-oxanaphthalen-4-one (also known as "PD98059"); and
N-[2-(3H-indol-3-yl)ethyl]-9-isopropyl-2-(5-methyl-3-pyridyl)purin-6-amine; (also known as "GNF351").

Additional non-limiting examples of molecules with AhR antagonist activity that may be used in the methods of this disclosure are described in WO 2012/015914, and include 2-{[2-(5-bromo-2-furyl)-4-oxo-4H-chromen-3-yl]oxy}acetamide (also known as "CB7993113") and CMLD-2166:

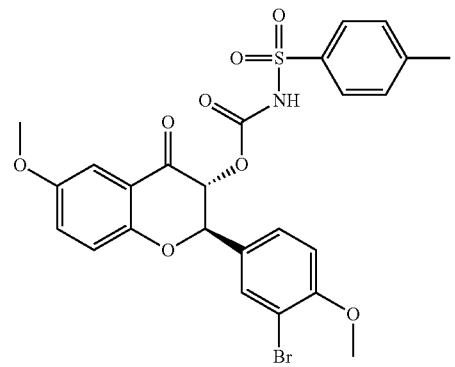

CMLD-2166

In some embodiments the AhR modulator is an AhR agonist. Non-limiting examples of molecules with AhR agonist activity that may be used in the methods of this disclosure include:
6-formylindolo[3,2-b]carbzole (FICZ);
polycyclic aromatic compounds;
halogenated aromatic hydrocarbons;
planar polychlorinated biphenyls;
purine derivatives;
tryptophan and its metabolites;
lipoxin A4-related eicosanoids;
indirubin;
bilirubin;
amino flavones;
β-naphtoflavone;
1H-benzimidazole;
5-methoxy-2-[[(4-methoxy-3,5-dimethyl-2-pyridinyl)methyl]sulfinyl]benzimidazole (also known as "omeprazole");
2-methyl-N-[4-nitro-3-(trifluoromethyl)phenyl]-propanamide (also known as "flutamide");
3,3-dindole methane;
1-allyl-7-trifluoromethyl-H-indazol-3-yl]-4-methoxyphenol
4-(3-chloro-phenyl)-pyrimidin-2-yl;
2-[[3-(3,4-dimethoxyphenyl)-1-oxo-2-propenyl]amino] benzoic acid (also known as "Tranilast");

trans-441-(4-[2-(Dimethylamino)ethoxy]phenyl)-2-phenyl-1-butenylphenol 2-(4-chlorophenyl)-4-oxo-4H-chromen-3-yl ethyl carbonate (also known as "CB7950998"); and 90282-01-B9 (T5838025).

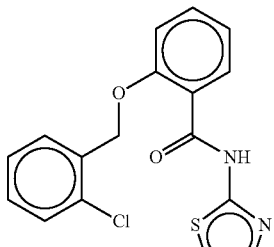

90282-01-B9 (T5838025)

The concentration of the AhR agonists and antagonists used will vary depending on how efficiently the agonist or antagonist agonizes or antagonizes the AhR. It is well within the level of skill in the art to determine an appropriate concentration of AhR agonist or antagonist to use by applying the teachings of this disclosure.

6-formylindolo[3,2-b]carbazole (FICZ) is typically used on cells in culture at a concentration of from 0.02 to 2.0 µM. In some embodiments FICZ is used at a concentration of from 0.04 to 1.0 uM. In some embodiments FICZ is used at a concentration of from 0.1 to 0.4 uM. In some embodiments FICZ is used at a concentration of about 0.02 uM, about 0.04 uM, about 0.06 uM, about 0.8 uM, about 0.1 uM, about 0.11 uM, about 0.12 uM, about 0.13 uM, about 0.14 uM, about 0.15 uM, about 0.16 uM, about 0.17 uM, about 0.18 uM, about 0.19 uM, about 0.2 uM, about 0.21 uM, about 0.22 uM, about 0.23 uM, about 0.24 uM, about 0.25 uM, about 0.26 uM, about 0.27 uM, about 0.28 uM, about 0.29 uM, about 0.30 uM, about 0.4 uM, about 0.5 uM, about 0.6 uM, about 0.7 uM, about 0.8 uM, about 0.9 uM, about 1.0 uM.

CH223191 is typically used on cells in culture at a concentration of from 0.5 to 50 uM. In some embodiments CH223191 is used at a concentration of from 1.0 to 25 uM. In some embodiments CH223191 is used at a concentration of from 2.5 to 10 uM. In some embodiments CH223191 is used at a concentration of about 1 uM. In some embodiments CH223191 is used at a concentration of about 2 uM. In some embodiments CH223191 is used at a concentration of about 3 uM. In some embodiments CH223191 is used at a concentration of about 4 uM. In some embodiments CH223191 is used at a concentration of about 5 uM. In some embodiments CH223191 is used at a concentration of about 6 uM. In some embodiments CH223191 is used at a concentration of about 7 uM. In some embodiments CH223191 is used at a concentration of about 8 uM. In some embodiments CH223191 is used at a concentration of about 9 uM. In some embodiments CH223191 is used at a concentration of about 10 uM.

In some embodiments more than one agonist and/or antagonist is used in combination.

With respect to this disclosure it is contemplated that AhR agonism and/or antagonism may be achieved by any method, including without limitation by using a molecule that binds to or interacts with the AhR protein itself, or a molecule that increases and/or decreases expression of AhR protein, as well as a molecule that increases and/or decreases cellular events mediated by AhR signaling. Accordingly, also included as AhR modulators are plasmids, DNA, or RNA fragments which themselves, or by virtue of a gene product they encode, alter AhR expression or function on transfection, transduction or otherwise entry into mammalian cells.

I. In Vitro Differentiated Hematopoietic Cells

The methods disclosed herein enable, in certain embodiments, the production of cell cultures comprising higher numbers of MEPs and higher proportions of MEPs than prior methods. For example, the inventors have shown that culturing pluripotent stem cells using the methods of this disclosure results in cell cultures comprising at least 500,000 MEPs per ml. In some embodiments the cultures comprise at least 750,000 MEPs per ml. In some embodiments the cultures comprise at least $1.0 \times 10^6$ MEPs per ml. In some embodiments the cultures comprise at least $1.1 \times 10^6$ MEPs per ml. In some embodiments the cultures comprise at least $1.2 \times 10^6$ MEPs per ml. In some embodiments the cultures comprise at least $1.3 \times 10^6$ MEPs per ml. In some embodiments the cultures comprise at least $1.4 \times 10^6$ MEPs per ml. In some embodiments the cultures comprise at least $1.5 \times 10^6$ MEPs per ml. In some embodiments the cultures comprise at least $1.6 \times 10^6$ MEPs per ml. In some embodiments the cultures comprise at least $1.7 \times 10^6$ MEPs per ml. In some embodiments the cultures comprise at least $1.8 \times 10^6$ MEPs per ml. In some embodiments the cultures comprise at least $1.9 \times 10^6$ MEPs per ml. In some embodiments the cultures comprise at least $2.0 \times 10^6$ MEPs per ml. In some embodiments such methods do not comprise culturing in the presence of an AhR agonist.

The methods disclosed herein enable, in certain embodiments that comprise culturing in the presence of an AhR agonist, the production of cell cultures comprising even higher numbers of MEPs and higher proportions of MEPs than prior methods. For example, the inventors have shown that culturing pluripotent stem cells using the methods of this disclosure that comprise culturing in the presence of an AhR agonist results in cell cultures comprising at least $5 \times 10^6$ MEPs per ml. In some embodiments the cultures comprise at least $7.5 \times 10^6$ MEPs per ml. In some embodiments the cultures comprise at least $1.0 \times 10^7$ MEPs per ml. In some embodiments the cultures comprise at least $1.1 \times 10^7$ MEPs per ml. In some embodiments the cultures comprise at least $1.2 \times 10^7$ MEPs per ml. In some embodiments the cultures comprise at least $1.3 \times 10^7$ MEPs per ml. In some embodiments the cultures comprise at least $1.4 \times 10^7$ MEPs per ml. In some embodiments the cultures comprise at least $1.5 \times 10^7$ MEPs per ml. In some embodiments the cultures comprise at least $1.6 \times 10^7$ MEPs per ml. In some embodiments the cultures comprise at least $1.7 \times 10^7$ MEPs per ml. In some embodiments the cultures comprise at least $1.8 \times 10^7$ MEPs per ml. In some embodiments the cultures comprise at least $1.9 \times 10^7$ MEPs per ml. In some embodiments the cultures comprise at least $2.0 \times 10^7$ MEPs per ml.

The methods in certain embodiments also provide for production in a single cell culture of at least $1 \times 10^6$ MEPs, at least $5 \times 10^6$ MEPs, at least $1 \times 10^7$ MEPs, at least $5 \times 10^7$ MEPs, at least $1 \times 10^8$ MEPs, or at least $5 \times 10^8$ MEPs.

The methods of this disclosure, in certain embodiments, produce cell cultures comprising MEPs in which a high proportion of the total cells in the culture are MEPs. MEPs represent less than 0.1% of the entire bone marrow population under normal, steady state conditions. In contrast, the methods of this disclosure produce cell cultures in which at least 1%, at least 2%, at least 3%, at least 4%, at least 5%, at least 10%, at least 15%, at least 20%, at least 25%, at least 30%, at least 35%, at least 40%, at least 45%, or at least 50% of the cells in the culture are MEPs.

In some embodiments the compositions of this disclosure comprise at least 1 of, at least 2 of, or all 3 of:

A) a concentration of MEPs of at least 500,000 MEPs per ml, at least 750,000 MEPs per ml, at least $1.0 \times 10^6$ MEPs per ml, at least $1.1 \times 10^6$ MEPs per ml, at least $1.2 \times 10^6$ MEPs per ml, at least $1.3 \times 10^6$ MEPs per ml, at least $1.4 \times 10^6$ MEPs per ml, at least $1.5 \times 10^6$ MEPs per ml, at least $1.6 \times 10^6$ MEPs per ml, at least $1.7 \times 10^6$ MEPs per ml, at least $1.8 \times 10^6$ MEPs per ml, at least $1.9 \times 10^6$ MEPs per ml, at least $2.0 \times 10^6$ MEPs per ml, at least $5 \times 10^6$ MEPs per ml, at least $7.5 \times 10^6$ MEPs per ml, at least $1.0 \times 10^7$ MEPs per ml, at least $1.1 \times 10^7$ MEPs per ml, at least $1.2 \times 10^7$ MEPs per ml, at least $1.3 \times 10^7$ MEPs per ml, at least $1.4 \times 10^7$ MEPs per ml, at least $1.5 \times 10^7$ MEPs per ml, at least $1.6 \times 10^7$ MEPs per ml, at least $1.7 \times 10^7$ MEPs per ml, at least $1.8 \times 10^7$ MEPs per ml, at least $1.9 \times 10^7$ MEPs per ml, or at least $2.0 \times 10^7$ MEPs per ml;

B) a total number of MEPs of at least $1 \times 10^6$ MEPs, at least $5 \times 10^6$ MEPs, at least $1 \times 10^7$ MEPs, at least $5 \times 10^7$ MEPs, at least $1 \times 10^8$ MEPs, or at least $5 \times 10^8$ MEPs; and C) a proportion of MEPs to total cells in the culture of at least 1%, at least 2%, at least 3%, at least 4%, at least 5%, at least 10%, at least 15%, at least 20%, at least 25%, at least 30%, at least 35%, at least 40%, at least 45%, or at least 50% of the cells in the culture are MEPs.

In some embodiments the culture further comprises at least one of red blood cells, megakaryocytes, and platelets.

In some embodiments the culture is made by a method that does not comprise sorting cells based on expression of at least one protein marker.

J. Therapeutic Uses of In Vitro Differentiated Hematopoietic Cells

The red blood cells and platelets made by the methods of this disclosure and provided by this disclosure may be used therapeutically to provide red blood cells or platelets to a patient in need thereof.

1. Red Blood Cells

A common use of red blood cells is to restore oxygen carrying capacity to the blood of a patient that is suffering from anemia due to trauma or other medical problems. Historically they were transfused as part of whole blood, but in modern practice the red blood cells and plasma components are transfused separately. The process of identifying a compatible blood product for transfusion is complicated and giving incompatible RBCs to a patient can be fatal.

Red blood cells for transfusion are often mixed with an anticoagulant and usually a storage solution which provides nutrients and preserves the functionality of the living cells, which are stored at refrigerated temperatures. For traditional red blood cell transfusion the cells are separated from the fluid portion of the blood either after it is collected from a donor or during the collection process by apheresis. The product is sometimes modified after collection to meet specific patient requirements.

The main reason a red blood cell transfusion is carried out is to treat anemia. Anemia is a condition that occurs when the body doesn't have enough red, oxygen-carrying blood cells. This means that the body's tissues and cells aren't getting enough oxygen.

Broadly speaking, anemia can be caused by impaired red blood cell production, increased RBC destruction (hemolytic anemias), blood loss and fluid overload (hypervolemia). Several of these may interplay to cause anemia eventually. Indeed, the most common cause of anemia is blood loss, but this usually does not cause any lasting symptoms unless a relatively impaired RBC production develops.

Anemia from impaired production of red blood cells can be caused by a disturbance of proliferation and differentiation of stem cells (which can be caused by pure red cell aplasia, aplastic anemia, anemia of renal failure in conjunction with insufficient erythropoietin production, and anemia caused by an endocrine disorder), as disturbance of proliferation and maturation of erythroblasts (which can be caused by pernicious anemia, a form of megaloblastic anemia due to vitamin B12 deficiency, anemia of folic acid deficiency, anemia of prematurity, iron deficiency anemia, thalassemias, congenital dyserythropoietic anemias, and anemia of renal failure), and other mechanisms (myelophthisic anemia or myelophthisis, myelodysplastic syndrome, and anemia of chronic inflammation).

Anemia from increased destruction of red blood cells are generally classified as hemolytic anemias. These are generally featuring jaundice and elevated lactate dehydrogenase levels. Anemia from increased destruction of red blood cells can be caused by intrinsic (intracorpuscular) abnormalities (which can be caused by hereditary spherocytosis, hereditary elliptocytosis, abetalipoproteinemia, pyruvate kinase and hexokinase deficiencies, glucose-6-phosphate dehydrogenase deficiency and glutathione synthetase deficiency, hemoglobinopathies, sickle cell anemia, hemoglobinopathies causing unstable hemoglobins, paroxysmal nocturnal hemoglobinuria, autoimmune disease, and mechanical trauma to red cells, such as following open heart surgery.

Anemia from blood loss can occur following trauma or surgery that causes acute blood loss, gastrointestinal track lesions that cause chronic blood loss, gynecological disturbances that cause chronic blood loss, and menstruation.

Red blood cells of this disclosure, such as for example the red blood cells made using a method disclosed herein, may be used to provide red blood cells to a patient in need thereof, such as a patient suffering from anemia, such as an anemia type described herein. Generally, the red blood cells will be provided to the patient by transfusion in the form of a transfusion composition (sometimes referred to as "packed red cells"). A "transfusion composition" as used herein is a composition comprising red blood cells and another factor or factors which provides nutrients and preserves the functionality of the living cells. In some embodiments the transfusion comprises at least one component selected from an anticoagulant, a buffer, and a nutrient. In some embodiments it is a buffered solution comprising at least one nutrient and at least one anticoagulant.

In some embodiments the patient is in need of treatment for sickle cell anemia.

In some embodiments the patient is in need of treatment for thalassemia.

In some embodiments the red blood cells are blood type matched to the blood type of the patient.

In some embodiments the red blood cells are red blood cells that are differentiated in vitro from MEP cells that are differentiated in vitro. In some embodiments the MEP cells are differentiated in vitro from MEP precursor cells obtained from the patient. In some embodiments the MEP cells are differentiated in vitro from iPSCs derived from somatic cells of the patient. For example, the iPSCs may be iPSCs derived from a somatic cell of the patient, which are then used to make MEP cells, which are then optionally used to make red blood cells having a high degree of genetic identity to the genome of the patient. In some embodiments the RBCs are differentiated in vitro from RBC precursor cells isolated from the patient. In some embodiments the RBC precursor cells are, for example, at least one of HSC cells and MEP cells. In some embodiments the genome of the MEPs and/or RBCs is at least 99% genetically identical to the genome of the patient, is at least 99.1% genetically identical to the genome of the patient, is at least 99.2% genetically identical to the genome of the patient, is at least 99.3% genetically identical to the genome of the patient, is at least 99.4% genetically identical to the genome of the patient, is at least 99.5% genetically identical to the genome of the patient, is at least 99.6% genetically identical to the genome of the patient, is at least 99.7% genetically identical to the genome of the patient, is at least 99.8% genetically identical to the genome of the patient, is at least 99.9% genetically identical to the genome of the patient, is at least 99% genetically identical to the genome of the patient, is at least 99.95% genetically identical to the genome of the patient, or is identical to the genome of the patient.

2. Platelets

If the number of platelets in the bloodstream is too low, excessive bleeding can occur. However, if the number of platelets is too high, blood clots can form (thrombosis), which may obstruct blood vessels and result in such events as a stroke, myocardial infarction, pulmonary embolism or the blockage of blood vessels to other parts of the body, such as the extremities of the arms or legs. An abnormality or disease of the platelets is called a thrombocytopathy, which could be either a low number of platelets (thrombocytopenia), a decrease in function of platelets (thrombasthenia), or an increase in the number of platelets (thrombocytosis). There are disorders that reduce the number of platelets, such as heparin-induced thrombocytopenia (HIT) or thrombotic thrombocytopenic purpura (TTP) that typically cause thromboses, or clots, instead of bleeding.

Platelet transfusions are traditionally given to those undergoing chemotherapy for leukemia, multiple myeloma, those with aplastic anemia, AIDS, hypersplenism, ITP, sepsis, bone marrow transplant, radiation treatment, organ transplant or surgeries such as cardiopulmonary bypass.

Decreased platelet counts caused by decreased production of platelets can be caused by at least one of: Vitamin B12, deficiency, folic acid deficiency, leukemia, myelodysplastic syndrome, decreased production of thrombopoietin by the liver in liver failure, sepsis, Dengue fever, and hereditary syndromes such as congenital amegakaryocytic thrombocytopenia (CAMT), thrombocytopenia absent radius syndrome, Fanconi anemia, Bernard-Soulier syndrome, May-Hegglin anomaly, Grey platelet syndrome, Alport syndrome, and Wiskott-Aldrich syndrome.

Decreased platelet counts caused by increased destruction of platelets can be caused by at least one of: idiopathic thrombocytopenic purpura, thrombotic thrombocytopenic purpura, hemolytic-uremic syndrome, disseminated intravascular coagulation, paroxysmal nocturnal hemoglobinuria, antiphospholipid syndrome, systemic lupus erythematosus, post-transfusion purpura, neonatal alloimmune thrombocytopenia, splenic sequestration of platelets due to hypersplenism, Dengue fever, and HIV-associated thrombocytopenia.

Thrombocytopenia can also be induced by medications, including valproic acid, methotrexate, carboplatin, interferon, isotretinoin, panobinostat, montelukast sodium, H2 blockers and proton-pump inhibitors.

Platelets of this disclosure, such as for example the platelets made using a method disclosed herein, may be used to provide platelets to a patient in need thereof, such as a patient suffering from thrombocytopenia. Generally, the platelets will be provided to the patient by transfusion in the form of a transfusion composition. A "transfusion composition" as used herein is a composition comprising platelets and at least one second component selected from an anti-coagulant, a buffer, and a nutrient.

In some embodiments the platelets are blood type matched to the blood type of the patient.

In some embodiments the platelets are platelets that are differentiated in vitro from MEP cells that are differentiated in vitro. In some embodiments the MEP cells are differentiated in vitro from MEP precursor cells derived from the patient. In some embodiments the MEP cells are differentiated in vitro from iPSCs derived from somatic cells of the patient and the platelets are also differentiated in vitro from the iPSCs derived from the patient. For example, the iPSCs may be iPSCs derived from a somatic cell of the patient, which are then used to make MEP cells, which are then optionally used to make megakaryocytes that in turn differentiate into platelets. In some embodiments the platelets are differentiated in vitro from platelet precursor cells isolated from the patient. In some embodiments the platelet precursor cells are at least one of HSC cells and MEP cells, for example. The megakaryocytes in many such embodiments have a high degree of genetic identity to the genome of the patient. In some embodiments the genome of the MEPs and/or platelets is at least 99% genetically identical to the genome of the patient, is at least 99.1% genetically identical to the genome of the patient, is at least 99.2% genetically identical to the genome of the patient, is at least 99.3% genetically identical to the genome of the patient, is at least 99.4% genetically identical to the genome of the patient, is at least 99.5% genetically identical to the genome of the patient, is at least 99.6% genetically identical to the genome of the patient, is at least 99.7% genetically identical to the genome of the patient, is at least 99.8% genetically identical to the genome of the patient, is at least 99.9% genetically identical to the genome of the patient, is at least 99% genetically identical to the genome of the patient, is at least 99.95% genetically identical to the genome of the patient, or is identical to the genome of the patient.

K. Analysis of Agents Using In Vitro Differentiated Hematopoietic Cells

The methods of this disclosure allow for production of vast quantities of MEPs, red blood cells, megakaryocytes, and platelets. As such, these methods and cells made by them have many features that in certain embodiments will make them advantageous for use in screening procedures that utilize at least one cell type selected from MEP, red blood cell, megakaryocyte, and platelet. For example, in some embodiments the use of at least one cell type selected from MEP, red blood cell, megakaryocyte, and platelet differentiated from a source of pluripotent stem cells provides a high degree of uniformity to an assay involving a plurality of test agents. In some embodiments the at least one cell type selected from MEP, red blood cell, megakaryocyte, and platelet are differentiated from a source of pluripotent stem cells that share at least one common genetic factor selected from a blood type genotype, a minor histocompatibility antigen genotype, and a major histocompatibility genotype. In some embodiments the at least one cell type selected from MEP, red blood cell, megakaryocyte, and platelet are differentiated from pluripotent stem cells comprising genomes that are at least 99% genetically identical to each other, at least 99.1% genetically identical to each other, at least 99.2% genetically identical to each other, at least 99.3% genetically identical to each other, at least 99.4% genetically identical to each other, at least 99.5% genetically identical to each other, at least 99.6% genetically identical to each other, at least 99.7% genetically identical to each other, at least 99.8% genetically identical to each other, at least 99.9% genetically identical to each other, at least 99.95% genetically identical to each other, or are genetically identical to each other.

Accordingly, provided herein are methods of screening a test agent for an effect on at least one cell type selected from MEP, red blood cell, megakaryocyte, and platelet, the at least one cell type made by a method of this disclosure or provided by this disclosure. In some embodiments the method comprises: a) making the at least one cell type selected from MEP, red blood cell, megakaryocyte, and platelet by a method of this disclosure; b) contacting the at least one cell type selected from MEP, red blood cell, megakaryocyte, and platelet with the test agent; and c) observing a change in the at least one cell type selected from MEP, red blood cell, megakaryocyte, and platelet.

In some embodiments the method further comprises comparing the change in the at least one cell type selected from MEP, red blood cell, megakaryocyte, and platelet in the presence of the test agent to a similar cell grown in control conditions that do not comprise the test agent.

In some embodiments the method further comprises d) contacting the at least one cell type selected from MEP, red blood cell, megakaryocyte, and platelet with a control agent; f) observing a change in the at least one cell type selected from MEP, red blood cell, megakaryocyte, and platelet in the presence of the control agent, and g) comparing the change in the at least one cell type selected from MEP, red blood cell, megakaryocyte, and platelet in the presence of the control agent to the change in the at least one cell type selected from MEP, red blood cell, megakaryocyte, and platelet in the presence of the test agent.

The change in the at least one cell type selected from MEP, red blood cell, megakaryocyte, and platelet in the presence of the test agent is in some embodiments selected from a change in rate of cell proliferation, a change in rate of cell death, a change in the expression level of at least one gene, and a change in the level of at least one protein in the cell. In some embodiments the change is a change in the level of a marker of toxicity. The change is in some embodiments selected from an increase and a decrease in rate or level.

In some embodiments it is useful to screen a compound for an effect on at least one cell type selected from MEP, red blood cell, megakaryocyte, and platelet that is derived from a subject. For example, if the at least one cell type selected from MEP, red blood cell, megakaryocyte, and platelet is make from a starting cell that is at least one of a MEP precursor cell, a red blood cell precursor cell, a megakaryocyte precursor cell, and a platelet precursor cell. If the precursor cell is obtained form the subject, then in many embodiments the results of the screening will be particularly relevant to the subject. For example, because the at least one cell type selected from MEP, red blood cell, megakaryocyte, and platelet will comprise a genome that is very similar to substantially identical to the genome of the subject, the at least one cell type selected from MEP, red blood cell, megakaryocyte, and platelet are expected to respond to the compound in a manner that is very similar to the response of similar cells in vivo in the subject after administration of the compound to the subject.

Accordingly, in some embodiments, making the at least one cell type selected from MEP, red blood cell, megakaryocyte, and platelet by a method of this disclosure comprises: obtaining at least one of a MEP precursor cell, a red blood cell precursor cell, a megakaryocyte precursor cell, and a platelet precursor cell from the subject.

L. Therapeutic Uses of AhR Modulators

As shown in the Examples, AhR antagonism results in Mk specification and production in cultures of MEPs. The Examples also show that administration of an effective amount of an AhR agonist to a mammal increases the platelet count of the mammal. Taken together these data demonstrate that both AhR agonism and antagonism play a role in the process: AhR agonism increases the number of MEPs, which can then go on to produce more Mks and more platelets (as well as more RBCs). Moreover, AhR antagonists appear to act on aspecified Mks to increase endoreplication and platelet production.

Accordingly, this disclosure provides methods of increasing the platelet count of a mammal. In some embodiments the methods comprise administering an effective amount of an AhR modulator to the mammal. In some embodiments the methods comprise administering an effective amount of an AhR agonist to the mammal. In some embodiments the methods comprise administering an effective amount of an AhR antagonist to the mammal. In some embodiments the methods comprise administering an effective amount of an AhR agonist and an effective amount of an AhR antagonist to the mammal. In some embodiments in which both an AhR agonist and an AhR antagonist are administered, the AhR agonist and AhR antagonist are co-administered. In some embodiments in which both an AhR agonist and an AhR antagonist are administered, the AhR agonist and AhR antagonist are administered separately. Increasing platelet counts in mammals is useful in many ways, including, by way of example, to treat a mammal suffering from and/or at risk of thrombocytopenia. Accordingly, this disclosure also provides methods of treating thrombocytopenia in a mammal. In some embodiments the methods comprise administering an effective amount of an AhR agonist to the mammal.

Pharmaceutical compositions for use in the methods of treatment and methods of increasing the platelet count in a mammal herein are formulated to contain therapeutically effective amounts of at least one AhR receptor modulator. The pharmaceutical compositions are useful, for example, in the treatment of at least one disease state characterized by a low platelet count.

In some embodiments, the at least one AhR receptor modulator is formulated into a suitable pharmaceutical preparation such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the AhR modulator described above is formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more AhR modulators or pharmaceutically acceptable derivatives is (are) mixed with a suitable pharmaceutical carrier or vehicle.

Pharmaceutically acceptable derivatives include acids, bases, enol ethers and esters, salts, esters, hydrates, solvates and prodrug foul's. The derivative is selected such that its pharmacokinetic properties are superior with respect to at least one characteristic to the corresponding neutral agent. The AhR modulator may be derivatized prior to formulation.

The concentrations of the AhR modulator in the compositions are effective for delivery of an amount, upon administration, that treats one or more of the symptoms of at least one disease state characterized by a reduced platelet count and/or a reduction in normal platelet function, for example.

Typically, by way of example and without limitation, the compositions are formulated for single dosage administration. To formulate a composition, the weight fraction of AhR modulator is dissolved, suspended, dispersed or otherwise mixed in a selected vehicle at an effective concentration such that the treated condition is relieved or ameliorated. Pharmaceutical carriers or vehicles suitable for administration of the AhR modulator include any such carriers known to those skilled in the art to be suitable for the particular mode of administration.

In addition, the AhR modulator may be formulated as the sole active agent in the composition or may be combined with other active agents. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a AhR modulator provided herein in phosphate buffered saline lacking divalent cations (PBS) is added and the flask shaken until the lipid film is dispersed. The resulting vesicles are washed to remove unencapsulated AhR modulator, pelleted by centrifugation, and then resuspended in PBS.

The active AhR modulator is included in the pharmaceutically acceptable carrier in an amount sufficient to exert a therapeutically useful effect in the absence of undesirable side effects on the patient treated. The therapeutically effective concentration may be determined empirically by testing the agents in in vitro and in vivo systems described herein and in International Patent Application Publication Nos. 99/27365 and 00/25134 and then extrapolated there from for dosages for humans.

The concentration of active AhR modulator in the pharmaceutical composition will depend on absorption, inactivation and excretion rates of the active agent, the physicochemical characteristics of the agent, the dosage schedule, and amount administered as well as other factors known to those of skill in the art. For example, the amount that is delivered is sufficient to treat at least one disease state characterized by at least one of reduced platelet count and reduced platelet function, as described herein.

Typically a therapeutically effective dosage should produce a serum concentration of active agent of from about 0.1 ng/ml to about 50-100 μg/ml, for example. The pharmaceutical compositions typically should provide a dosage of from about 0.001 mg to about 2000 mg of AhR modulator per kilogram of body weight per day, such as from about 0.01 mg to about 200 mg of AhR modulator per kilogram of body weight per day, or from about 0.1 mg to about 20 mg of AhR modulator per kilogram of body weight per day, or from about 1 mg to about 10 mg of AhR modulator per kilogram of body weight per day, or from about 1 mg to about 5 mg of AhR modulator per kilogram of body weight per day. Pharmaceutical dosage unit forms are prepared to provide from about 1 mg to about 1000 mg, such as from about 10 to about 500 mg of the active agent or a combination of agents per dosage unit form.

The active agent may be administered at once, or may be divided into a number of smaller doses to be administered at intervals of time. It is understood that the precise dosage and duration of treatment is a function of the disease state being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed methods.

Thus, effective concentrations or amounts of one or more AhR X modulators or pharmaceutically acceptable derivatives thereof are mixed with a suitable pharmaceutical carrier or vehicle for systemic, topical or local administration to form pharmaceutical compositions. AhR modulators are included in an amount effective for treating at least one disease state characterized by reduced platelet count and/or platelet function. The concentration of active agent in the composition will depend on absorption, inactivation, excretion rates of the active agent, the dosage schedule, amount administered, particular formulation as well as other factors known to those of skill in the art.

The compositions are intended to be administered by a suitable route, including by way of example and without limitation orally, parenterally, rectally, topically and locally. For oral administration, capsules and tablets can be used. The compositions are in liquid, semi-liquid or solid foul and are formulated in a manner suitable for each route of administration.

Solutions or suspensions used for parenteral, intradermal, subcutaneous, or topical application can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or single or multiple dose vials made of glass, plastic or other suitable material.

In instances in which the agents exhibit insufficient solubility, methods for solubilizing agents may be used. Such methods are known to those of skill in this art, and include, but are not limited to, using co-solvents, such as dimethylsulfoxide (DMSO), using surfactants, such as TWEEN®, or dissolution in aqueous sodium bicarbonate. Pharmaceutically acceptable derivatives of the agents may also be used in formulating effective pharmaceutical compositions.

Upon mixing or addition of the agent(s), the resulting mixture may be a solution, suspension, emulsion or the like. The form of the resulting mixture depends upon a number of factors, including the intended mode of administration and the solubility of the agent in the selected carrier or vehicle. The effective concentration is sufficient for treating one or more symptoms of at least one disease state characterized by reduced platelet count and/or function and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the agents or pharmaceutically acceptable derivatives thereof. The pharmaceutically therapeutically active agents and derivatives thereof are typically formulated and administered in unit-dosage forms or multiple-dosage forms. Unit-dose foams as used herein refers to physically discrete units suitable for human and animal subjects and packaged individually as is known in the art. Each unit-dose contains a predetermined quantity of the therapeutically active agent sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active agent in an amount sufficient to alleviate the symptoms of the treated subject.

Dosage forms or compositions containing active agent in the range of 0.005% to 100% with the balance made up from non-toxic carrier may be prepared. For oral administration, a pharmaceutically acceptable non-toxic composition is formed by the incorporation of any of the normally employed excipients, such as, for example and without limitation, pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active agent, such as 0.1-85%, or such as 75-95%. [0186] The active agents or pharmaceutically acceptable derivatives may be prepared with carriers that protect the agent against rapid elimination from the body, such as time release formulations or coatings. The compositions may include other active agents to obtain desired combinations of properties. AhR modulators or pharmaceutically acceptable derivatives thereof, may also be advantageously administered for therapeutic or prophylactic purposes together with another pharmacological agent known in the general art to be of value in treating at least one disease state characterized by reduced platelet counts and/or function.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent forms with the combination of other ingredients known to those skilled in the art.

In some embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, crosscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble F1) and C dyes, mixtures thereof; and water insoluble ID and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents, include by way of example and without limitation, glycerin, sorbitol, ethyl alcohol and syrup. Examples of preservatives include without limitation glycerin, methyl and propylparaben, benzoic add, sodium benzoate and alcohol. Non-aqueous liquids utilized in emulsions, include by way of example and without limitation, mineral oil and cottonseed oil. Emulsifying agents, include by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents, include by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants such fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, for example in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients, include by way of example and without limitation, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a AhR modulator is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Parenteral administration of the AhR modulators includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Aqueous vehicles include, by way of example and without limitation, Sodium Chloride Injection, Ringers Injection, Isotonic Dextrose Injection, Sterile Water Injection, Dextrose and Lactated Ringers Injection. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include, by way of example and without limitation, ethyl alcohol, polyethylene glycol and propylene glycol for water miscible vehicles and sodium hydroxide, hydrochloric acid, citric acid or lactic acid for pH adjustment.

The concentration of the pharmaceutically active agent is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. Preparations for parenteral administration should be sterile, as is known and practiced in the art.

Illustratively, intravenous or intraarterial infusion of a sterile aqueous solution containing an active agent is an effective mode of administration. Another embodiment is a sterile aqueous or oily solution or suspension containing an active agent injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active agent to the treated tissue(s). The active agent may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The agent may be suspended in micronized or other suitable form or may be derivatized, e.g., to produce a more soluble active product or to produce a prodrug or other pharmaceutically acceptable derivative. The form of the resulting mixture depends upon a number of factors, including the intended mode of administration and the solubility of the agent in the selected carrier or vehicle. The effective concentration is sufficient for ameliorating the symptoms of the condition and may be empirically determined.

Lyophilized powders can be reconstituted for administration as solutions, emulsions, and other mixtures or formulated as solids or gels.

The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The agents or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, by way of example and without limitation, have diameters of less than about 50 microns, such as less than about 10 microns.

The agents may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active agent alone or in combination with other pharmaceutically acceptable excipients can also be administered.

These solutions, particularly those intended for ophthalmic use, may be formulated, by way of example and without limitation, as about 0.01% to about 10% isotonic solutions, pH about 5-7, with appropriate salts.

Other routes of administration, such as transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

Pharmaceutical dosage thin's for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is, by way of example and without limitation, about 2 to 3 gm.

Tablets and capsules for rectal administration are manufactured using the same pharmaceutically acceptable substance and by the same methods as for formulations for oral administration.

The AhR modulators, or pharmaceutically acceptable derivatives thereof, may also be formulated to be targeted to a particular tissue, receptor, or other area of the body of the subject to be treated. Many such targeting methods are well known to those of skill in the art. Such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of an agent provided herein in phosphate buffered saline lacking divalent cations (PBS) is added and the flask shaken until the lipid film is dispersed. The resulting vesicles are washed to remove unencapsulated agent, pelleted by centrifugation, and then resuspended in PBS.

The AhR modulators or pharmaceutically acceptable derivatives for use in the methods may be packaged as articles of manufacture containing packaging material, a AhR modulator or pharmaceutically acceptable derivative thereof, which is effective for modulating the activity of a AhR or for treatment, of one or more symptoms of at least one disease state characterized by reduced platelet count and/or platelet function within the packaging material, and a label that indicates that the AhR modulator or composition, or pharmaceutically acceptable derivative thereof, is used for modulating the activity of AhR for treatment of one or more symptoms of at least one disease state characterized by reduced platelet count and/or function.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

EXAMPLES

The following examples serve to more fully describe the manner of using the invention. These examples are presented for illustrative purposes and should not serve to limit the true scope of the invention.

A. Experimental Procedures 1. iPSC Derivation and Culture Conditions iPSC derivation was achieved by transduction of the hSTEMCCA lentivirus. The hSTEMCCA lentiviral vector was constructed by ligating cDNA encoding human OCT4, KLF4, SOX2, and cMYC into the pHAGE lentiviral plasmid as previously described (Somers, A. et al. Generation of transgene-free lung disease-specific human induced pluripotent stem cells using a single excisable lentiviral stem cell cassette. *Stem Cells* 28, 1728-1740 (2010)). Lentivirus was packaged in 293T cells by co-transfection of five plasmids and were concentrated via a previously published ultracentrifugation protocol (Sommer, C. A. et al. Excision of reprogramming transgenes improves the differentiation potential of iPS cells generated with a single excisable vector. *Stem Cells* 28, 64-74 (2010); Sommer, C. A. et al. Induced pluripotent stem cell generation using a single lentiviral stem cell cassette. *Stem Cells* 27, 543-549 (2009)). Peripheral Blood Mononuclear Cells (PBMCs) were used as source material for iPSC production. Peripheral blood (4 ml) was drawn from human participants into a BD Vacutainer vial (362760). Samples were centrifuged at 37° C. for 25 minutes at 1800 rcf and the resulting buffy coat was collected in a 15 ml falcon tube. Cells were washed with PBS and counted to ensure that $1\times10^6$ cells were isolated for culture. Cells were resuspended in 2 ml of expansion medium, consisting of QBSF-60 (Quality Biological 160-204-101), 50 ng/ml hSCF (R&D 255-SC-010), 10 ng/ml hIL-3 (R&D 203-IL-010), 2 U/ml hEPOgen (Amgen), 40 ng/ml hIGF-1 (R&D 291-GI-050), 50 ug/ml Ascorbic Acid (Sigma A4403), 100 ug/ml Primocin (Invivogen ant-pm-2) and 1 μM Dexamethasone (Sigma D4902). After 8-9 days, polybrene was added to the media (5 ug/ml) and the hSTEMCCA lentivirus was added to the culture at an MOI ranging from 1 to 10. After 24 hours, the inoculated culture was spun at 2250 g for 90 minutes and the polybrene media was discarded. The cells were then plated onto irradiated Mouse Embryonic Fibroblasts (iMEFs) and cultured for roughly 15 days in "iPSC media" that includes DMEM F12 (Invitrogen 11330057) 10 ng/ml bFGF (R&D 233-FB-025) 1 ng/ml Rho Kinase Inhibitor (Cayman Chemical 10005583) 20% Knock-out Replacement Serum (KOSR) (Invitrogen 10828028) and 100 ug/ml Primocin. Clones were then picked and expanded into long-term culture.

2. Directed Differentiation of iPSCs into Mesoderm Cell Fate

High passage iPSCs were plated onto matrigel coated 6-well plates in iPSC media conditioned on iMEFs for 24 hours and supplemented with 2 ng/ml Rho Kinase Inhibitor and 20 ng/ml bFGF. After two days, iPSC media was replaced with Mesoderm D0-1 media: RPMI (Invitrogen A1049101) supplemented with 5 ng/ml hBMP-4 (R&D 314-BP-010), 50 ng/ml hVEGF (R&D 293-VE-010), 25 ng/ml hWnt3a (R&D 287-TC-500) and 10% KOSR. At Day 2, Mesoderm D0-1 media was replaced with Mesoderm D2 media: RPMI supplemented with 5 ng/ml hBMP-4, 50 ng/ml hVEGF, 20 ng/ml bFGF and 10% KOSR. Mesoderm D3 media consisted of the following: StemPro 34 (Invitrogen 10639011), 5 ng/ml hBMP-4, 50 ng/ml hVEGF, and 20 ng/ml bFGF. Mesoderm media for days 4 and 5 consisted of: StemPro 34, 15 ng/ml hVEGF, and 5 ng/ml bFGF. Day 6 mesoderm media: 74% IMDM (Invitrogen 12330061), 24% Hams F12 (Mediatech 10-080-CV), 1% B27 supplement (Invitrogen 12587-010), 0.5% N2-supplement (Invitrogen 17502-048), 0.5% BSA (Sigma A3059), 50 ng/ml hVEGF, 100 ng/ml bFGF, 100 ng/ml hSCF (R&D 255-SC-010), 25 ng/ml hFlt3 Ligand (R&D 308-FKN-005). Day 7 media: 74% IMDM, 24% Hams F12, 1% B27 supplement, 0.5% N2-supplement, 0.5% BSA, 50 ng/ml hVEGF, 100 ng/mlbFGF, 100 ng/ml hSCF, 25 ng/ml hFlt3 Ligand, 50 ng/ml hTPO (Genentech G140BT), 10 ng/ml IL-6 (R&D 206-IL-010), 0.5 U/ml hEPOgen and 0.2 uM 6-formylindolo [3,2-b]carbazole (FICZ) (Santa Cruz SC300019). After Day 7, 0.5 ml of Day 7 media was added to the culture daily without aspirating the media from the previous day. All base media mixes included 2 mM L-Glutamine (Invitrogen 25030081), $4\times10^{-4}$M Monothioglycerol (Sigma M1753), 100 ug/ml Primocin, and 50 ug/ml Ascorbic Acid. Cells in suspension were collected and assayed at Days 10-13 or split for long-term culture.

3. Lentiviral Vector Generation and Application

PCR primers were designed to amplify the MMTV-DRE (mouse mammary tumour virus/dioxin response element region from murine CY1A1 gene) promoter region from AHR activity reporter construct pGudLuc1.1, with integrated SpeI and NotI cut sites at the 5' and 3' ends respectively. The restriction enzyme digested PCR product was then inserted into the pHAGE2 lentiviral Ef1α-dsRed (NLS)-IRES-ZsGreen plasmid and the pHAGE2 lentiviral Ef1α-destabilized ZsGreen by excision of the Ef1α promoter and ligation of the SpeI and NotI digested MMTV-DRE. Additionally, the AHR repressor was cloned into the pHAGE2 lentiviral Ef1α-dsRed(NLS)-IRES-ZsGreen. Primers were designed to amplify the f. heteroclitus AHRR coding region from an HPV422-based construct, with NotI/BamHI cut sites incorporated at the 5' and 3' sites respectively. The dsRed (NLS) insert was excised and digested AHRR was ligated into the aforementioned vector.

VSV-G pseudotyped lentiviral particles were packaged and concentrated as previously published. (Murphy, G. J., Mostoslaysky, G., Kotton, D. N. & Mulligan, R. C. Exogenous control of mammalian gene expression via modulation of translational termination. *Nat Med.* 12, 1093-1099. Epub 26 Aug. 1096. (2006)) Cells were infected overnight and subsequent dsRed and ZsGreen gene expression was monitored by fluorescence microscopy and flow cytometry as indicated in the text.

4. AHR Small Molecule Competition Assays 6-formylindolo[3,2-b]carbazole (FICZ), an AHR small molecule agonist, and CH223191, an AHR competitive inhibitor were used for these assays. CH223191 was added to mesoderm cultures at Day 6 at 5 uM (lx) and 2.5 uM (0.5×). 0.2 uM FICZ was added to cultures at Day 7 and media was added daily. DMSO was used as a vehicle control.

5. Quantitative RT-PCR

RNA was extracted using the RNeasy kit (Qiagen) according to the manufacturer's instructions and DNase treated using the DNA-free kit (Ambion AM1906). Reverse transcription into cDNA was performed using the High Capacity cDNA Reverse Transcription Kit (Applied Biosystems 4368814). Quantitative (real time) PCR amplification of cDNA was performed using Taqman probes for AHR (Hs00169233_m1), CYP1B1 (Hs002382916_s1), HBA (Hs00361191_g1), HBB (Hs00758889_s1), HBG (Hs01629437_s1), vWF (Hs00169795_m1), PF4 (Hs00427220_g1), NF-E2 (Hs00232351_1) and CD62P (Hs00927900_m1) and run on the Applied Biosystems StepOne machine. Relative gene expression was normalized to B-actin (Hs99999903_m1).

6. Flow Cytometry

Roughly 10^5 cells were collected, spun, and re-suspended in 0.5% BSA in PBS. Samples were incubated for 30 min at ambient temperature with human antibodies including CD41a-FITC (BD 555466), CD235-PE (BD 555570), CD71-FITC (BD 555536), washed and spun at 3300 rpm for 7 min, and re-suspended in 0.5% BSA in PBS with 1 ug/ml Propidium Iodide. Samples were run on a BD FACScalibur using Cellquest Pro software and analyzed via FloJo 8.7. For ploidy analysis, cells were treated with 1.5% NP-40 (Boston Bioproducts P-872) and 62.5 ug/ml Propidium Iodide in PBS immediately before FACScalibur interrogation. For murine bone marrow, samples were first incubated for 5 min at ambient temperature with murine conjugated antibody CD16/32 (BD 553142) before a 30 min incubation with c-Kit-PE (BD 553355), CD41a-FITC (BD 553848), Ter119-PE (BD 553673). For cell viability assays, 2-3×10^5 cells were collected, re-suspended in 8.8 ug/ml Hoecsht 33342 in PBS supplemented with 5% FBS. Samples were then incubated in the dark at 37° C. for 15 min, washed, and re-suspended in 1 ug/ml Propidium Iodide in 5% FBS. Samples were run on an LSR-II machine with FACSDiva software and analyzed via FloJo 8.7.

7. Gene Expression Analysis

Figure 1B:
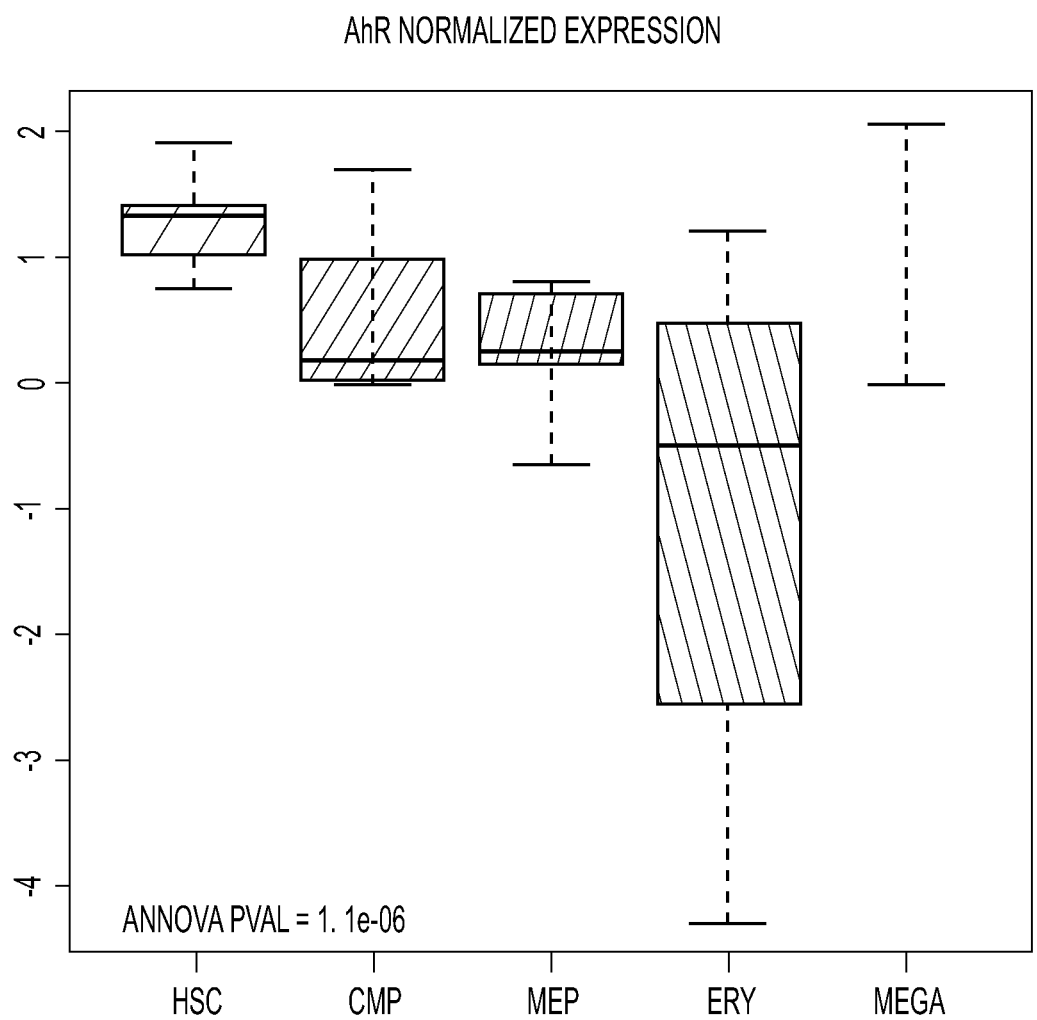

The data analyzed correspond to the RMA-processed, batch-normalized, Affymetrix® expression profiles downloaded from the dMap website (www.broadinstitute.org/dmap). This includes the expression levels of 8968 Entrez-annotated genes across 212 experiments representing 15 distinct populations (38 sub-populations) of hematopoietic cells. The data was projected onto the space of 37 manually curated AhR targets, plus AhR itself, and 72 experiments corresponding to 5 populations (11 sub-populations), defining the HSC-to-Mk/erythroid differentiation path. The genes were sorted based on hierarchical clustering with 1-Pearson correlation as the distance metric, and average linkage as the agglomeration rule (Eisen, M. B., Spellman, P. T., Brown, P. O. & Botstein, D. Cluster analysis and display of genome-wide expression patterns. *Proc Natl Acad Sci USA* 95, 14863-14868 (1998).) (FIG. 1a). The normalized expression level of AhR within each cell population (sub-population) was computed and visualized by means of box-and-whiskers plots (FIG. 1b). For each population, the plot reports the median (thick mid line), the middle half (the box), and the Interquartile Range (IQR, the distance between the "whiskers") of the distribution of AhR values. The difference in the expression level of AhR among cell populations was tested by standard analysis-of-variance (anova).

8. Statistical Analysis

Results are presented as the mean±the standard deviation of experiments performed in triplicate. Statistical significance was confirmed using the Student's t-test.

9. In Vivo Studies

C57Bl6 mice were injected daily intraperitoneally with FICZ suspended in vegetable oil using a weekly dose escalation scheme (Week 1: 1 mg/kg; Week 2: 2 mg/kg; Week 3: 4 mg/kg). Blood cell counts were assayed by Hemavet quantification of peripheral blood bleeds, at all 3 time points (Day 7, 14, and 21). Following the 3 week time point, mice were sacrificed and livers and spleens harvested for quantitative RT-PCR analyses.

Example 1: Analysis of Human Hematopoietic Cell Differentiation Genomic Mapping (dMap) Data As a roadmap for assessing the possible role of the AhR receptor in hematopoietic cells, we analyzed the "dMap" dataset (www.broadinstitute.org/dmap) (Novershtern, N. et al. Densely interconnected transcriptional circuits control cell states in human hematopoiesis. *Cell* 144, 296-309 (2011)) a publicly available compendium of expression profiles from 71 distinct purified populations of human hematopoietic cells. For our purposes, we focused on the HSC-to-Mk/erythroid differentiation path, and we analyzed the expression of a manually curated list of putative AhR targets. Hierarchical clustering was carried out to evaluate the co-expression patterns of AhR and its targets. This analysis revealed up-regulated Ahr mRNA expression in primitive stem cells, from the HSC to the MEP cell stage (FIG. 1). Erythroid cells clustered into 2 groups of cells with either up- or down-regulated Ahr. Ahr levels were consistently up-regulated in Mks. The levels of approximately 14 putative AhR target genes, including several of significant import to stem cells (e.g., c-myc, EGR1, and ALDHA1) were coordinately regulated with Ahr levels. Other important hematopoietic-specific genes such as NFE2, a critical regulator of both the erythroid and Mk lineages, also displayed coordinated differential expression with Ahr. These results indicated that Ahr expression is evident in hematopoietic progenitor cells and suggested that AhR may play a role in the development of human bipotential MEPs. These data, which clearly demonstrate AhR expression throughout the human hematopoietic system, allowed us to formulate a hypothesis that AhR activation could be used in an in vitro system to greatly enhance and direct the production and differentiation of hematopoietic progenitor cells.

Example 2: Production of Megakaryocyte-Erythroid Progenitors (MEPs) from Induced Pluripotent Stem Cells (iPSCs)

Figure 2A:
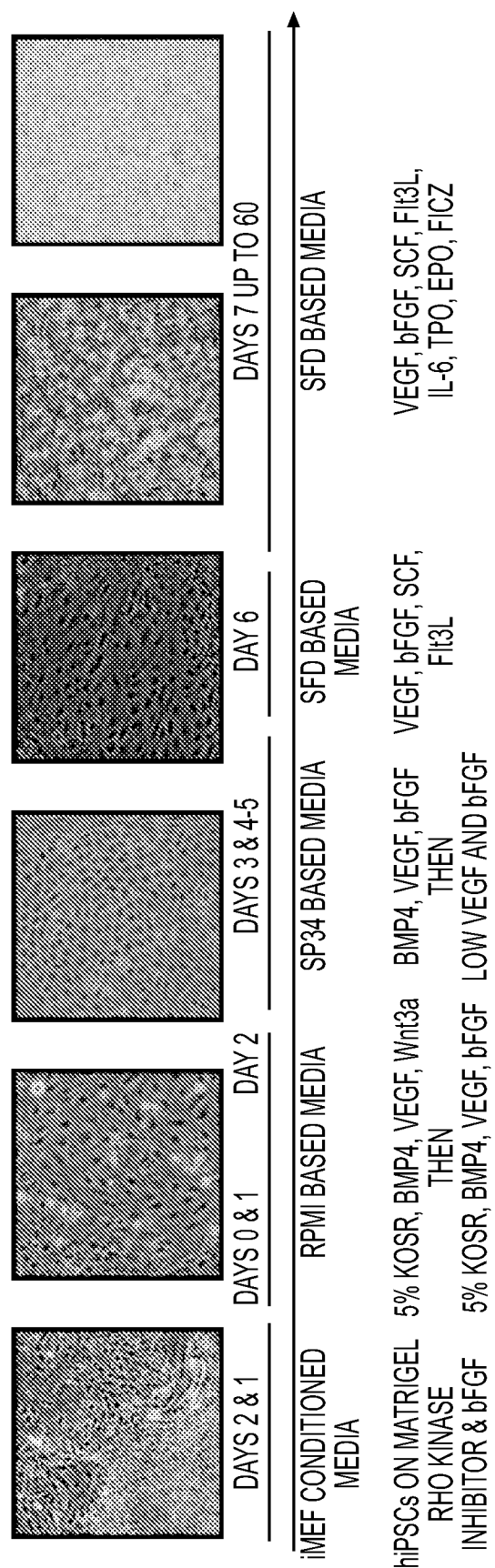
FIGS. 2A to 2D shows that the feeder-free, chemically defined production of megakaryocyte-erythroid progenitors (MEPs) from induced pluripotent stem cells (iPSCs) produces populations of cells that express definitive markers of both the megakaryocyte and erythroid lineages. (A) Differentiation strategy from iPSC to MEP stage. Phase contrast images of culture depicting morphological changes and the production of both an initial adherent layer followed by non-adherent MEPs. (B) Representative FACS analysis of Day 13 MEPs that co-express CD235-PE (red cells) and CD41-FITC (megakaryocytes). (C) FACS analysis of Day 13 MEPs that have been exposed to either erythroid or megakaryocyte-specific specification media for 5 days. (D) qPCR analysis of undifferentiated iPSCs vs. Day 13 MEPs. Relative gene expression was normalized to β-actin. Data is average of triplicate wells+SD. *p<0.05.
Figure 2B:
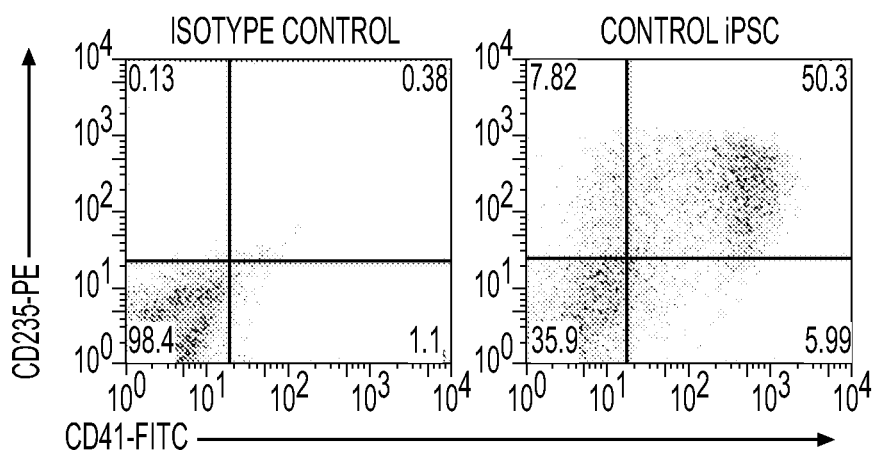
Figure 2C:
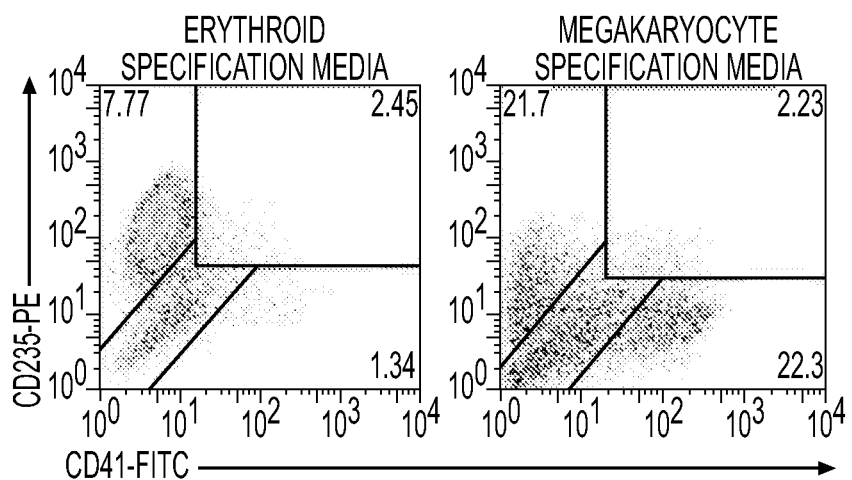
Figure 2D:
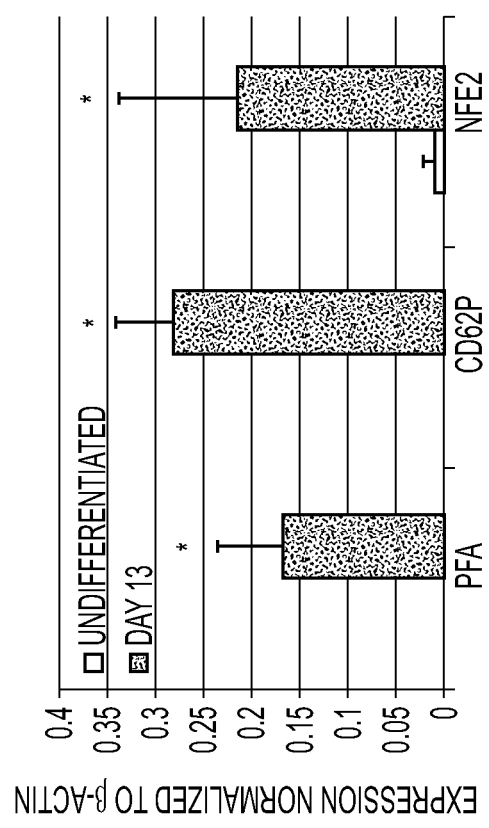
Figure 2D:
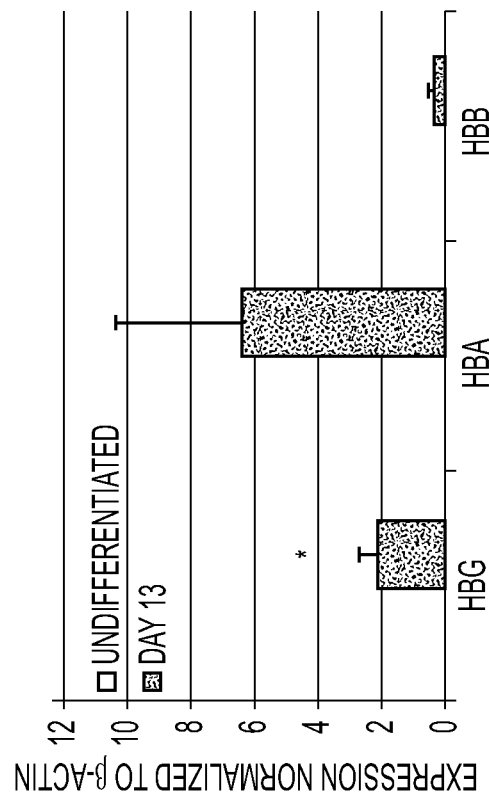

This example demonstrates the feeder-free, chemically defined production of megakaryocyte-erythroid progenitors (MEPs) from induced pluripotent stem cells (iPSCs), and shows that the cells express definitive markers of both the megakaryocyte and erythroid lineages. We sought to develop a novel, feeder-free, chemically-defined system for the production of hematopoietic progenitor cells from human iPSCs that would not be beholden to the use of stromal cell lines or xenogeneic agents, and would result in the ability to produce large numbers of clinically relevant, high purity hematopoietic cells. The approach employed in the development of this platform follows the roadmap provided by the developing embryo. Since ESC and iPSC resemble pluripotent, undifferentiated cells of the early blastocyst embryo, the signals active in the early embryo were harnessed to direct the differentiation of ESC and iPSC in vitro. Due to the known variability in the formation of human embryoid bodies (Bratt-Leal, A. M., Carpenedo, R. L. & McDevitt, T. C. Engineering the embryoid body microenvironment to direct embryonic stem cell differentiation. *Biotechnology progress* 25, 43-51 (2009)), our protocol utilized a 2D culture system optimized to produce bipotential hematopoietic progenitor cells within 10-13 days (FIG. 2A). A key element in this platform was the addition of a strong AhR ligand, FICZ, on day 7. The timeframe to generate MEPs is significantly shorter than that noted in previously described protocols (Takayama, N. et al. Generation of functional platelets from human embryonic stem cells in vitro via ES-sacs, VEGF-promoted structures that concentrate hematopoietic progenitors. *Blood* 111, 5298-5306 (2008); Gekas, C. & Graf, T. Induced pluripotent stem cell-derived human platelets: one step closer to the clinic. *The Journal of experimental medicine* 207, 2781-2784 (2010)) and requires no fractionation or further manipulation of the cells. In this system, differentiating iPSC produce an endothelial cell-based adherent layer from which non-adherent hematopoietic cells emerge beginning at Day 7 (FIG. 2A). As judged by immunophenotyping at Day 15, greater than 50% of these cells co-express CD235-Glycophorin A (erythroid lineage) and CD41 (Mk lineage) suggesting that bipotential MEPs had been generated (FIG. 2B). In comparison to undifferentiated iPSCs, these cells also upregulate globin gene expression and express a series of hallmark Mk markers (FIG. 2D). Furthermore, through the use of erythroid specification media containing EPO or Mk specification media containing TPO, iPSC-derived MEPs undergo a final fate choice in order to become either mature erythrocytes or Mks (FIG. 2C).

Figure 3A:
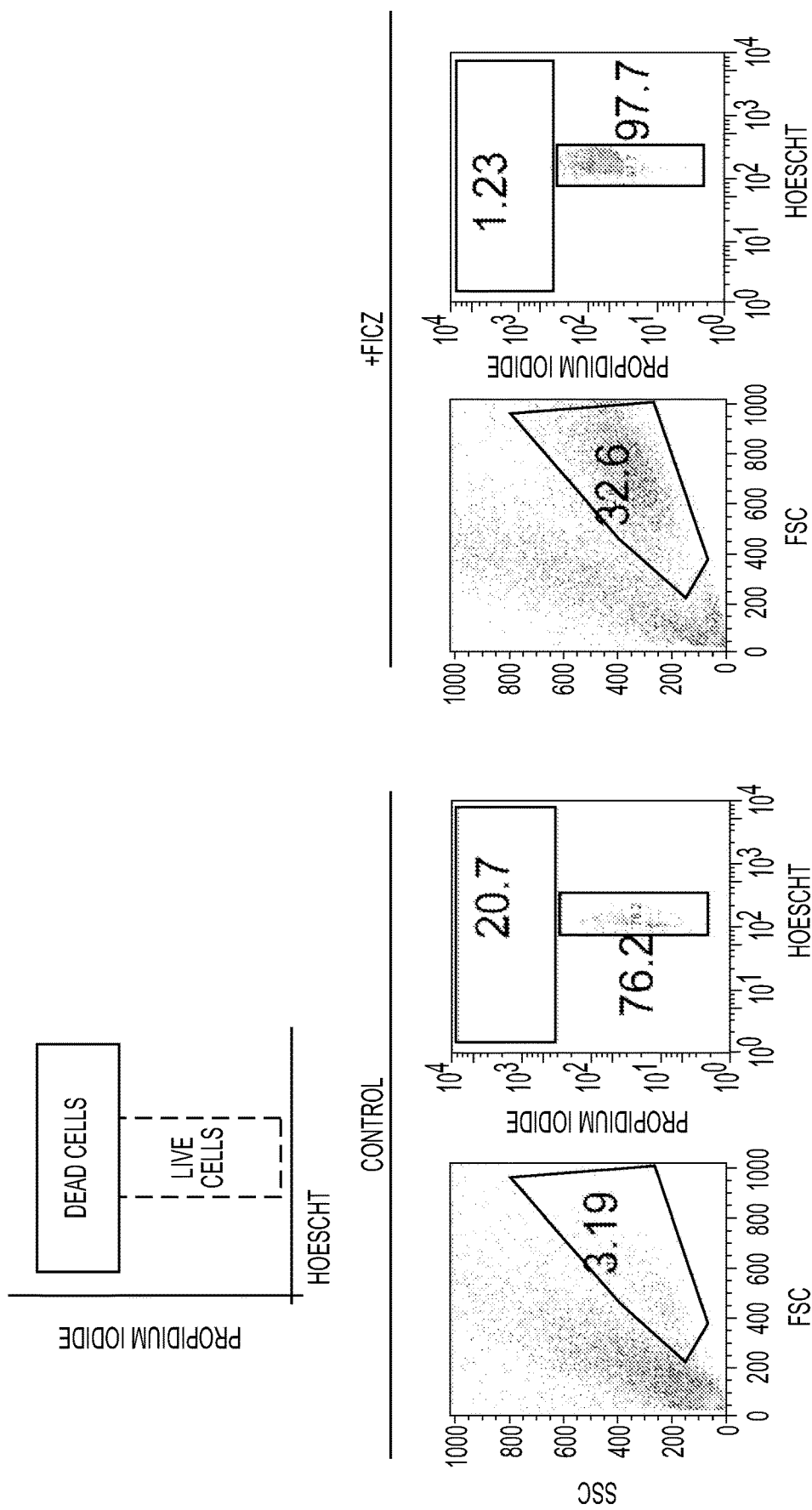
FIGS. 3A to 3D shows that the aryl hydrocarbon receptor (AhR) agonist FICZ inhibits apoptosis and allows for the exponential expansion of iPSC-derived MEPs: (A) Representative FACS dot plots of live versus dead cells (PI vs. Hoechst) from day 15 MEPs+FICZ. Plots were gated first in FSC vs. SSC and then from that population for PI$^+$ and PI$^-$ Hoechst$^+$. FICZ increases the population of live cells as delineated by FSC and SSC (32.6%) as well as PI$^-$ Hoechst$^+$ (97.7%). (B) Representative phase contrast images of MEP population+FICZ. (C) Growth curve of day 15 MEPs+/−0.2 μm FICZ. Cells were counted manually using trypan blue exclusion. Graphical data and the associated statistics are the result of three independent experiments per group. (D) Day 30 MEPs that have been treated with the AhR agonist FICZ are more proliferative than untreated cells as quantified by EDU incorporation.
Figure 3B:
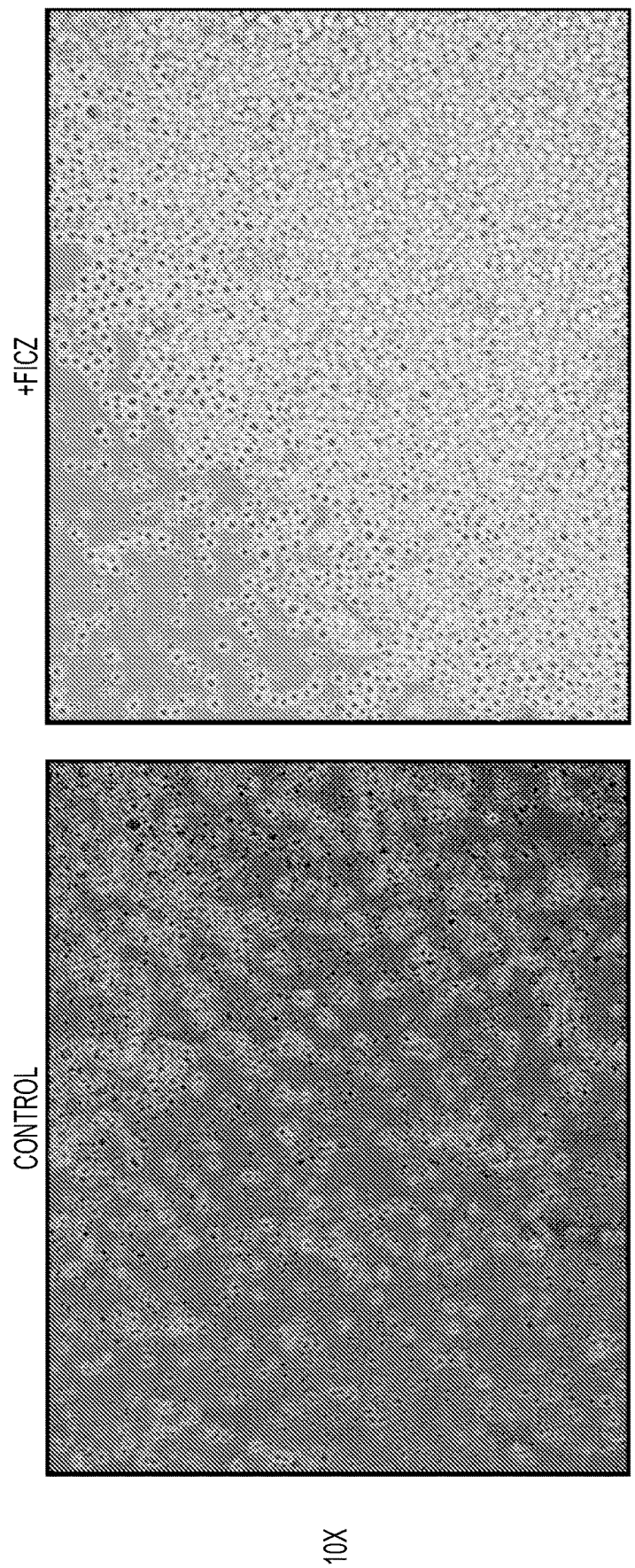
Figure 3C:
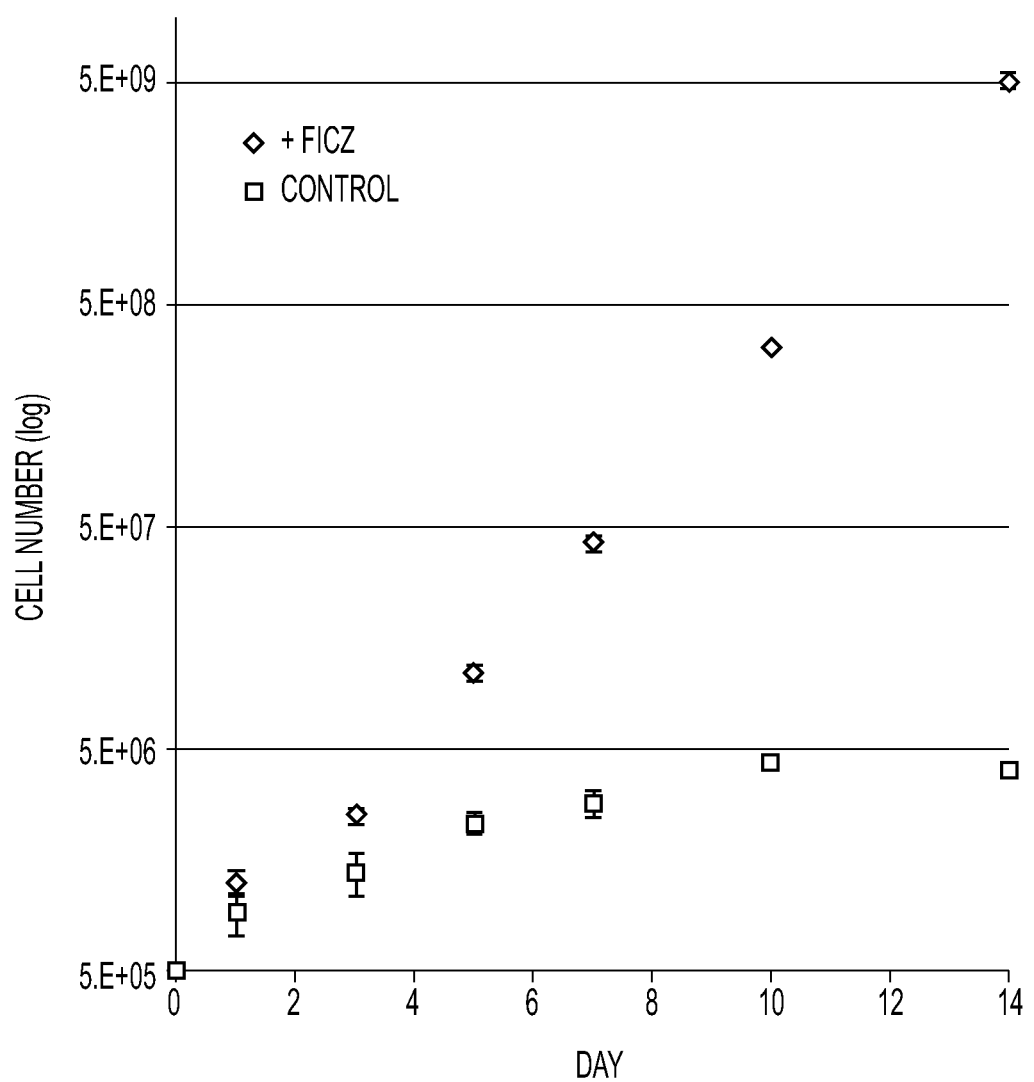

Example 3: The Aryl Hydrocarbon Receptor (AhR) Agonist FICZ Allows for the Exponential Expansion of iPSC-Derived MEPs Translation of iPSC technology to clinical applications has been hindered by the inability to produce sufficient, clinically relevant quantities of cells. Even for basic research studies, the numbers and quality of hematopoietic cells that can be produced through the directed differentiation of iPSC can be limiting (Chang, K. H., Bonig, H. & Papayannopoulou, T. Generation and characterization of erythroid cells from human embryonic stem cells and induced pluripotent stem cells: an overview. *Stem Cells Int.* 2011, 791604. Epub 79211 October 791626. (2011)). Here, we demonstrate that the AhR agonist FICZ has the ability to allow for the exponential expansion of iPSC-derived MEPs. In comparison to untreated control samples, FICZ-treated day 30 MEPs demonstrate significantly less cell death as judged by propidium iodide staining and Hoecsht dye exclusion allowing for the exponential expansion of the population (FIGS. 3A and B). As demonstrated in these plots, FICZ-treated cells have both increased viability with fewer cells undergoing apoptosis. Day 15 MEPs were also grown with or without the presence of FICZ and growth rates for each population were calculated. In contrast to untreated cells, FICZ treated MEPs demonstrated logarithmic expansion over a 2 week growth period (FIG. 3C).

Figure 3D:
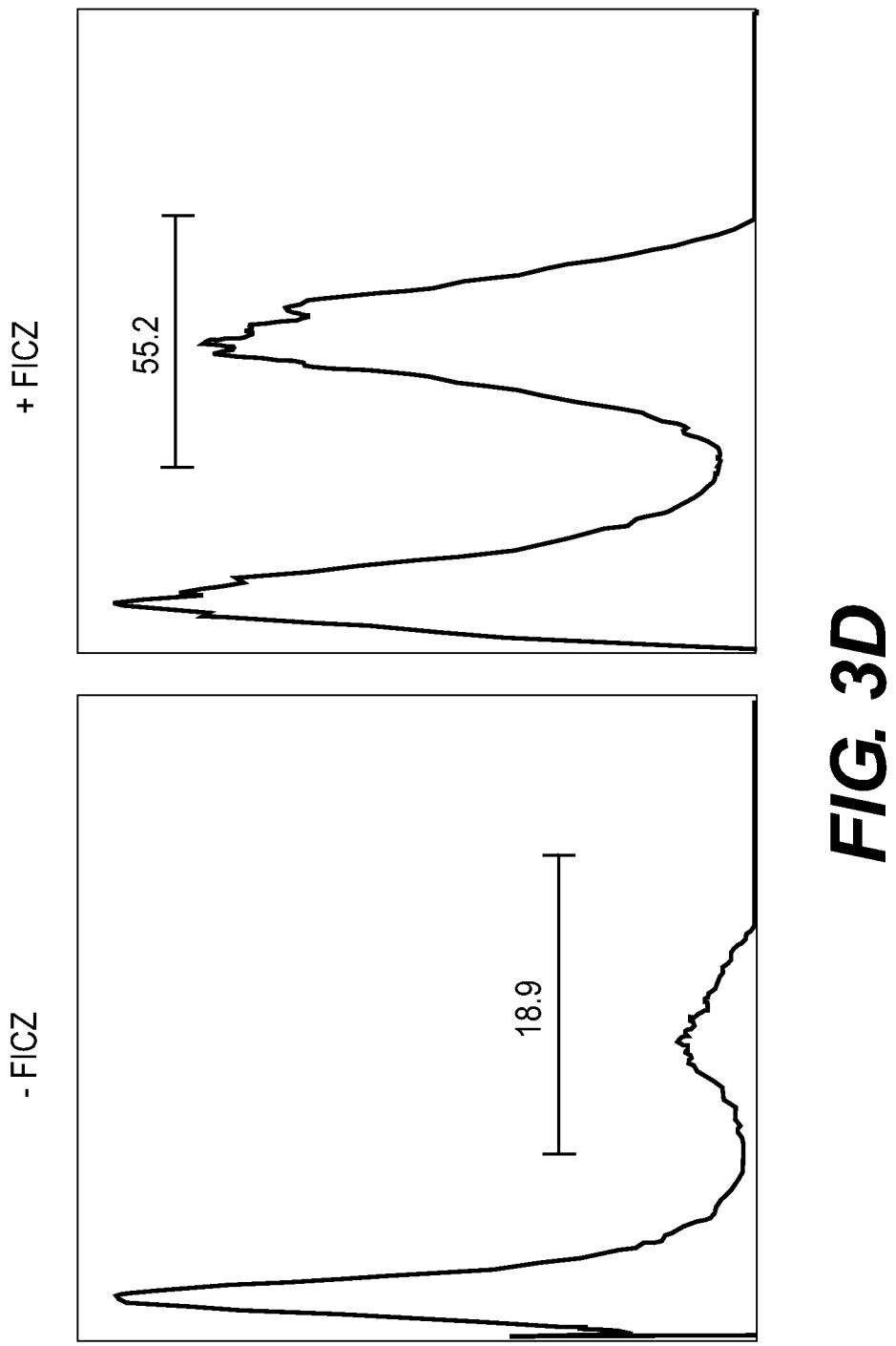

In a subsequent experiment, N-ethyl-N-nitrosourea (EDU) incorporation in day 30 MEPs was used to compare proliferation of FICZ-treated MEPS and control untreated MEPs. EDU is a labeling chemical that intercolates into the DNA of a cell and allows for the explicit tracking of proliferation. As shown in (FIG. 3D), day 30 MEPs that have been treated with the AhR agonist FICZ are far more proliferative than untreated cells.

Figure 4A:
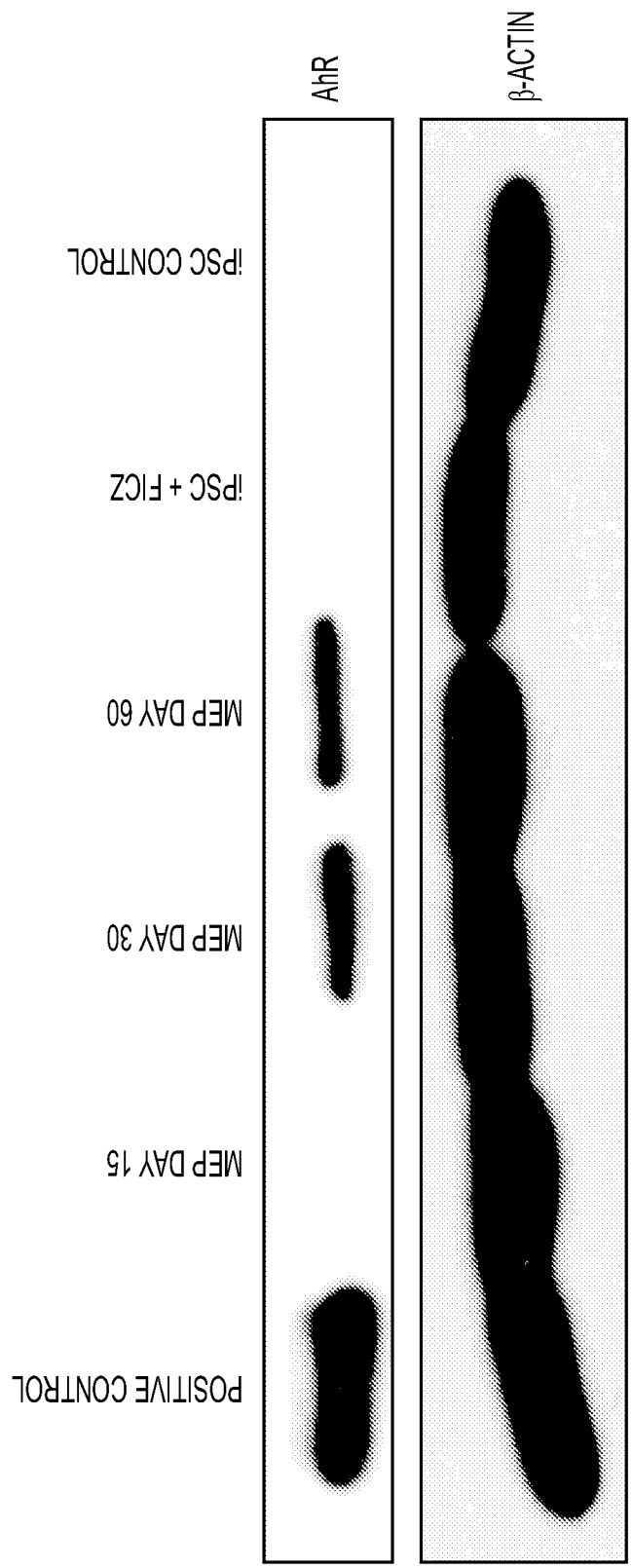
FIGS. 4A and 4B shows that AhR agonists induce CYP1B1 target gene expression in human iPSCs and MEPs. (A) Western blot analysis for AhR and β-actin protein expression in iPSC and MEPs. (B) qPCR data of iPSC and Day 15 MEPs with and without FICZ. Expression is normalized to β-actin levels. Data is average of triplicate wells+SD. *p<0.05, **p<0.005.
Figure 4B:
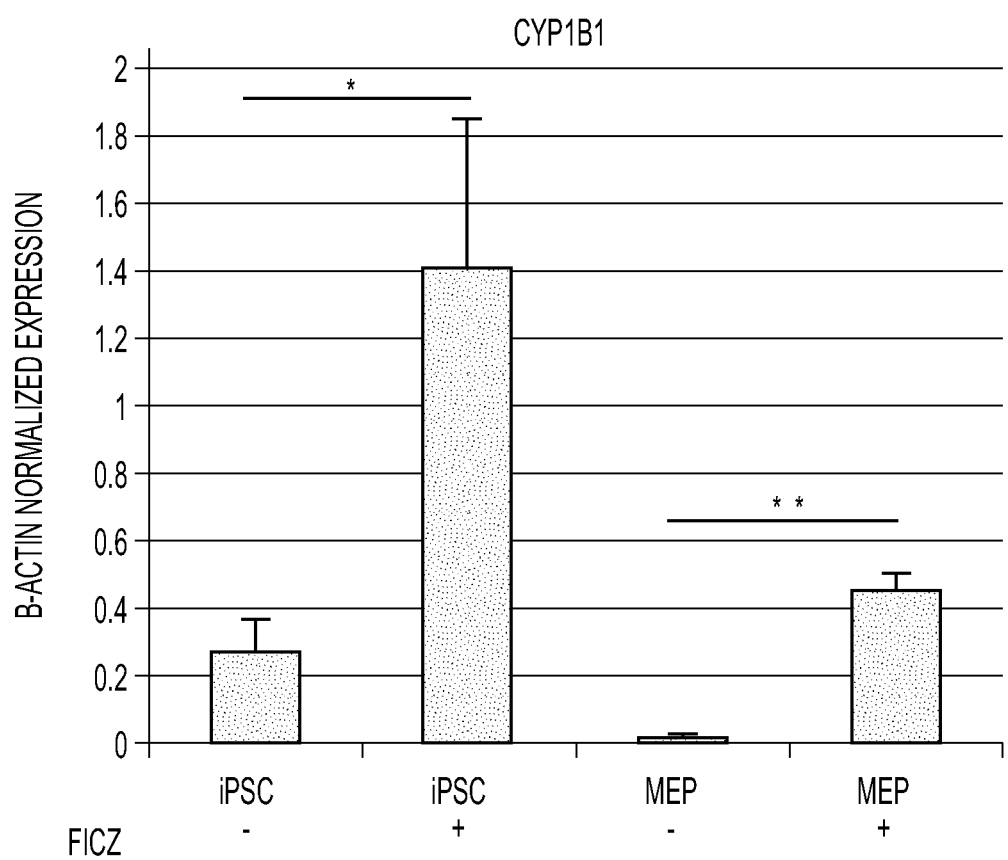
Figure 13B:
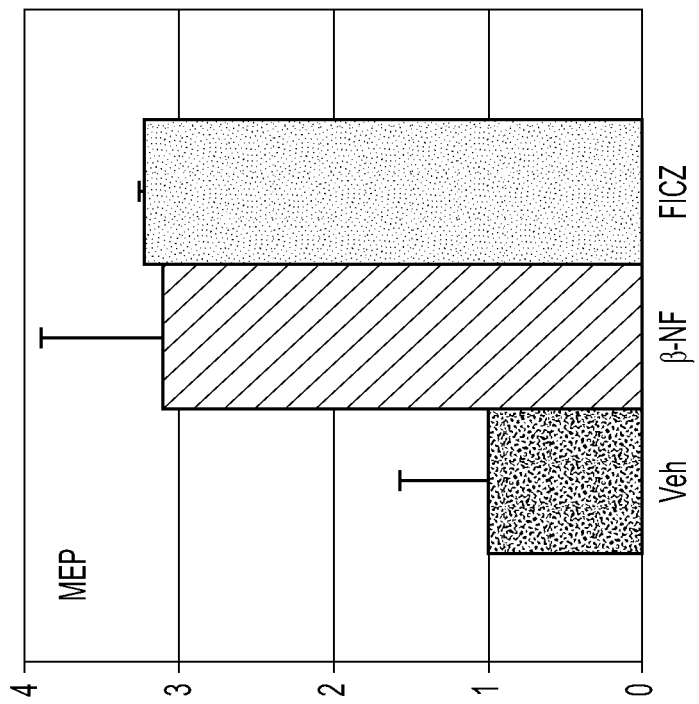
FIGS. 13A and 13B shows that iPSCs and MEPs are responsive to a spectrum of AhR agonists. (A) RT-PCR analysis of CYP1B1 in iPSC treated with TCDD or β-NF for 4 days. Data are averages of duplicate wells+SE and values are normalized to GAPDH. (B) RT-PCR analysis of CYP1B1 in MEP treated with β-NF or FICZ. Data are averages of duplicate wells+SE and values normalized to GAPDH.
Figure 13A:
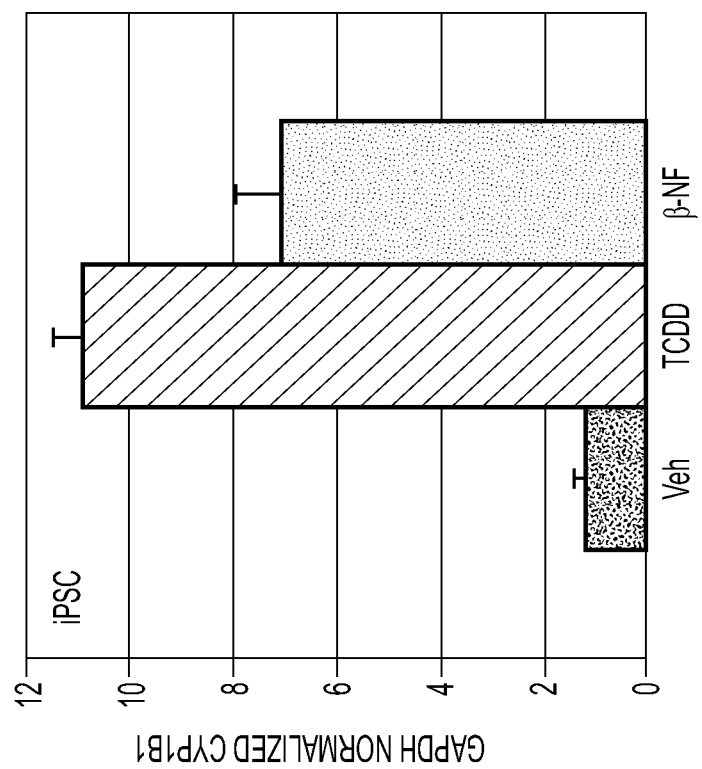

Example 4: AhR Agonists Induce CYP1B1 Target Gene Expression in Human iPSCs and MEPs To characterize AhR expression and functionality in both undifferentiated iPSCs and directly differentiated MEPs, AhR protein levels were determined via Western blot in these populations. AhR receptor was robustly expressed in day 30 and day 60 MEPs (FIG. 4A). However, AhR protein was not detected by western blotting in iPSC populations, and we postulated that AhR was expressed at extremely low levels in iPSCs, i.e., below the level of detectability with the antibodies used for Western blots. To test this hypothesis, the ability of FICZ to induce a prototypic AhR-target gene, CYP1B1, in iPSCs or, as a positive control, MEPs was assessed by quantitative RT-PCR. Both undifferentiated iPSCs and directly differentiated MEPs showed statistically significant increases in CYP1B1 expression following treatment with FICZ strongly suggesting that the AhR receptor is indeed expressed in these cells (FIG. 4B). Notably, these cell population also were responsive to other AhR agonists including the prototypic environmental AhR ligand, 2,3,7,8-tetrachlorodibenzo(p)dioxin (TCDD) (FIG. 13).

Figure 5A:
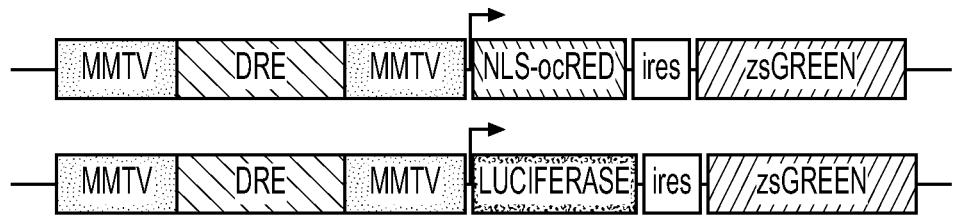
FIGS. 5A to 5F shows that AhR mediates the expansion and specification of bipotential hematopoietic progenitors. (A) Schematic representation of pHAGE2 lentiviral reporter constructs that contain the mouse mammary tumor virus flanking dioxin response element region from the murine CY1A1 gene (MMTV-DRE-MMTV) driving the expression of NLS-dsRed or luciferase IRES zsGreen (pHAGE2-MMTV-DRE-MMTV-NLS-dsRed-IRES-zsGreen and pHAGE2-MMTV-DRE-MMTV-luciferase-IRES-zsGreen). (B) FACS analysis for NLS-dsRED in MEPs infected with pHAGE2-MMTV-DRE-MMTV-NLS-dsRed-IRES-zs-Green. Infected cells were untreated or treated with 5 μM CH223191, or 0.4 μM FICZ. (C) Relative fluorescence units of cells infected with luciferase vector with or without FICZ or CH223191. (D) Phase contrast and fluorescent images of zs-Green expression in mock infected or infected cells. (E) Representative flow cytometry dot plots of live versus dead cells (PI vs. Hoechst) from D13 MEPs+FICZ and/or CH223191. For these experiments, MEPs were pretreated with the known AhR inhibitor CH223191 at D6 before the addition of FICZ at D7. (F) qPCR results of MEPs from "E", normalized to β-actin. Data is average of triplicate wells+ SD. *p<0.005.
Figure 5B:
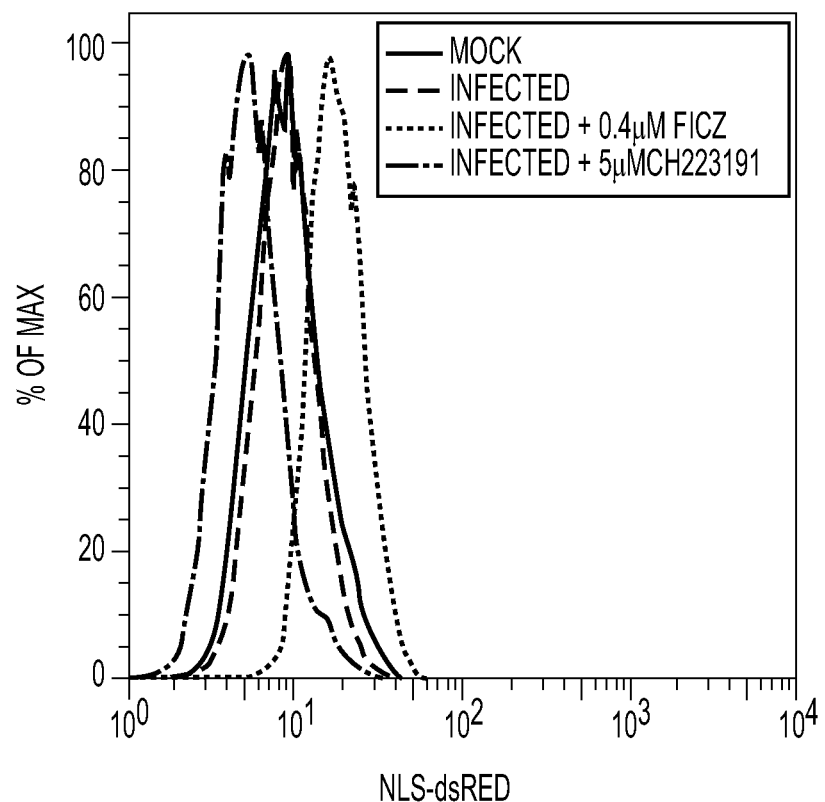
Figure 5C:
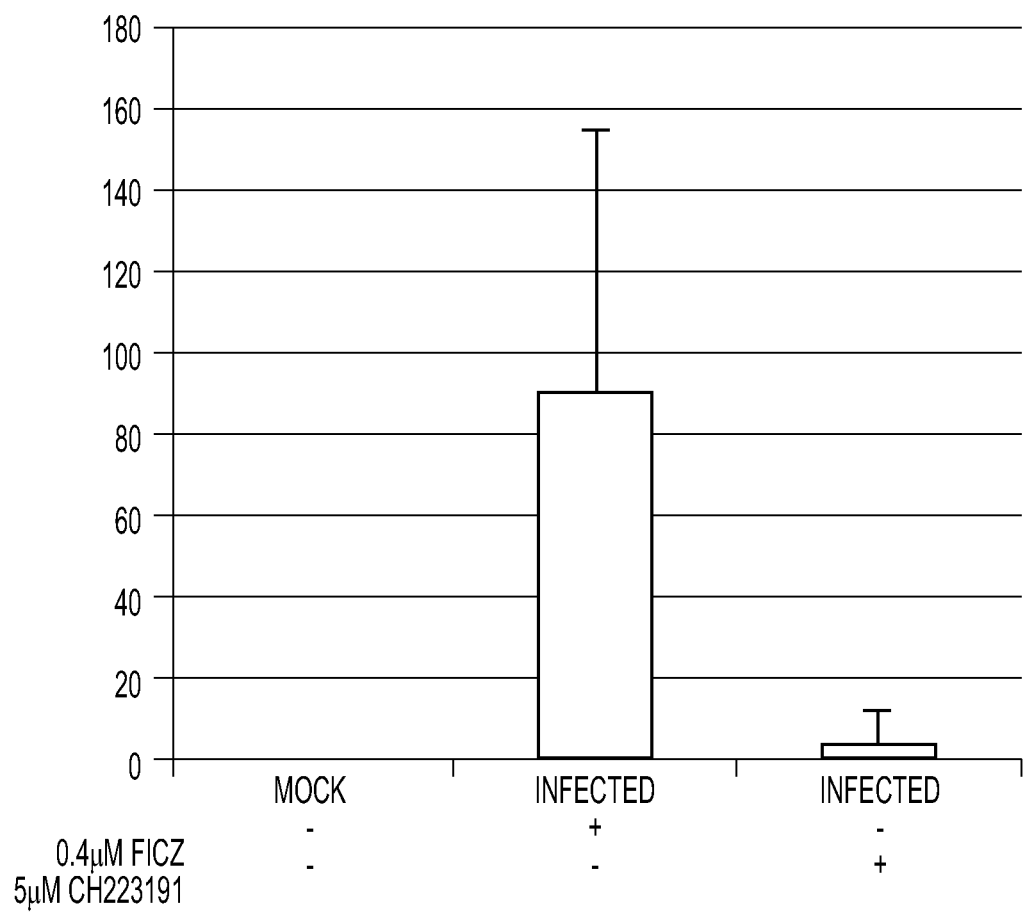
Figure 5D:
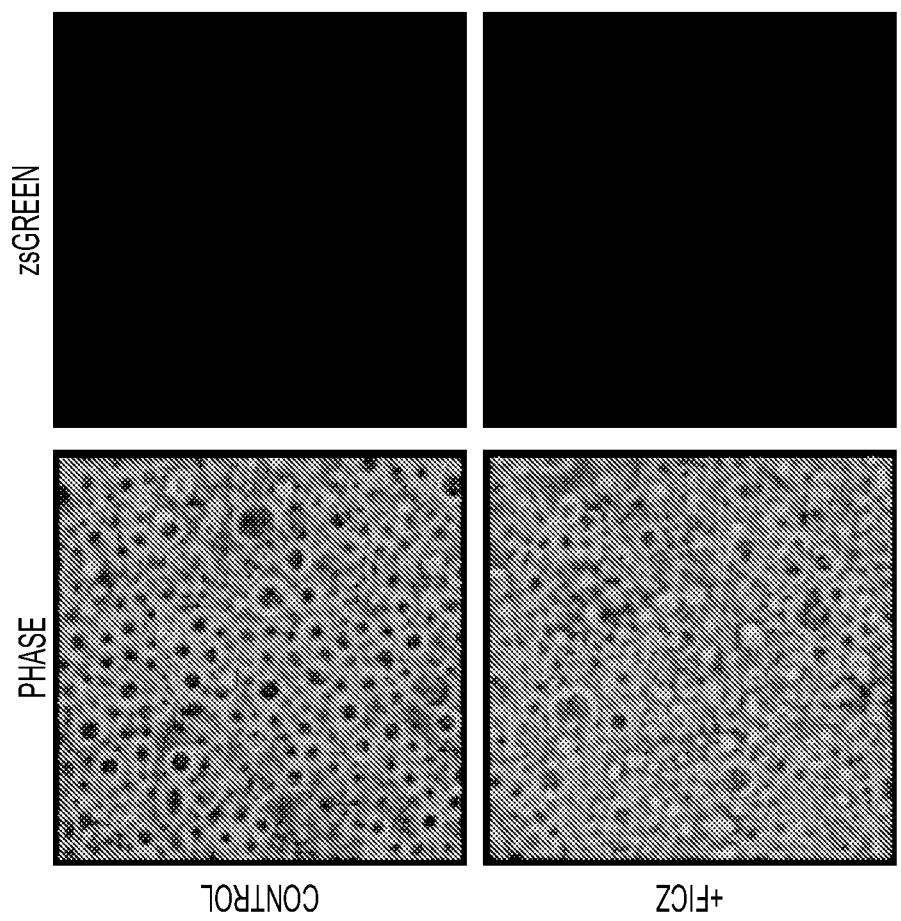

Example 5: AhR Mediates the Expansion and Specification of Bipotential Hematopoietic Progenitors To quantify AhR transcriptional activity, presumably mediated by an endogenous AhR ligand, we cloned a human AhR-responsive promoter (67, 68) into a lentivirus reporter vector that encodes for either nuclear localized dsRed and ZsGreen or luciferase and ZsGreen (FIG. 5A). These dual gene "AhR reporters" allow for normalization of transduction efficiency, negate any effect of auto-florescence, and allow for the quantification of AhR transcriptional activity. Day 30 MEPs were transduced with reporter lentivirus or mock infected at a multiplicity of infection (MOI) of 10 and grown in basal medium containing 0.2 $\mu$M FICZ for 72 hours. MEPs were then subjected to three different growth conditions in order to assess the activity of AhR in this population of cells: 1) The steady state condition consisting of 0.2 $\mu$M FICZ; 2) an increase in FICZ concentration to 0.4 $\mu$M; or 3) 0.2 $\mu$M FICZ plus 5 $\mu$M of the known AhR inhibitor CH223191 (Kim, S. H. et al. Novel compound 2-methyl-2H-pyrazole-3-carboxylic acid (2-methyl-4-o-tolylazo-phenyl)-amide (CH-223191) prevents 2,3,7,8-TCDD-induced toxicity by antagonizing the aryl hydrocarbon receptor. *Mol Pharmacol.* 69, 1871-1878. Epub 26 Mar. 1815. (2006)). In contrast to the mock infected MEPs, the AhR reporter-infected population displayed a modest increase in dsRed expression suggesting that the Dioxin Responsive Element in the reporter was being transactivated in the MEPs (FIG. 5B). When the reporter infected MEPs were subjected to an increased amount of the AhR agonist FICZ (0.4 $\mu$M), a significant increase in DsRed expression was noted, demonstrating that FICZ is capable of transactivating the AhR receptor in primary, iPSC-derived, directly differentiated MEPs (FIG. 5B, 5C). This result was also confirmed visually via immunoflourescence microscopy with ZsGreen+ cells only noted in the MEPs treated with 0.4 $\mu$M FICZ (FIG. 5D). Importantly, when the reporter-infected populations were subjected to growth medium containing 5 $\mu$M of the known AhR inhibitor CH223191, a significant decrease (below the level of expression in the mock infected populations) was noted in DsRed expression further demonstrating that FICZ-mediated transcriptional activity is mediated through the AhR receptor in iPSC-derived, directly differentiated MEPs (FIG. 5B). These results were confirmed quantitatively using a lentiviral backbone that encoded luciferase (FIG. 5C)

Figure 5E:
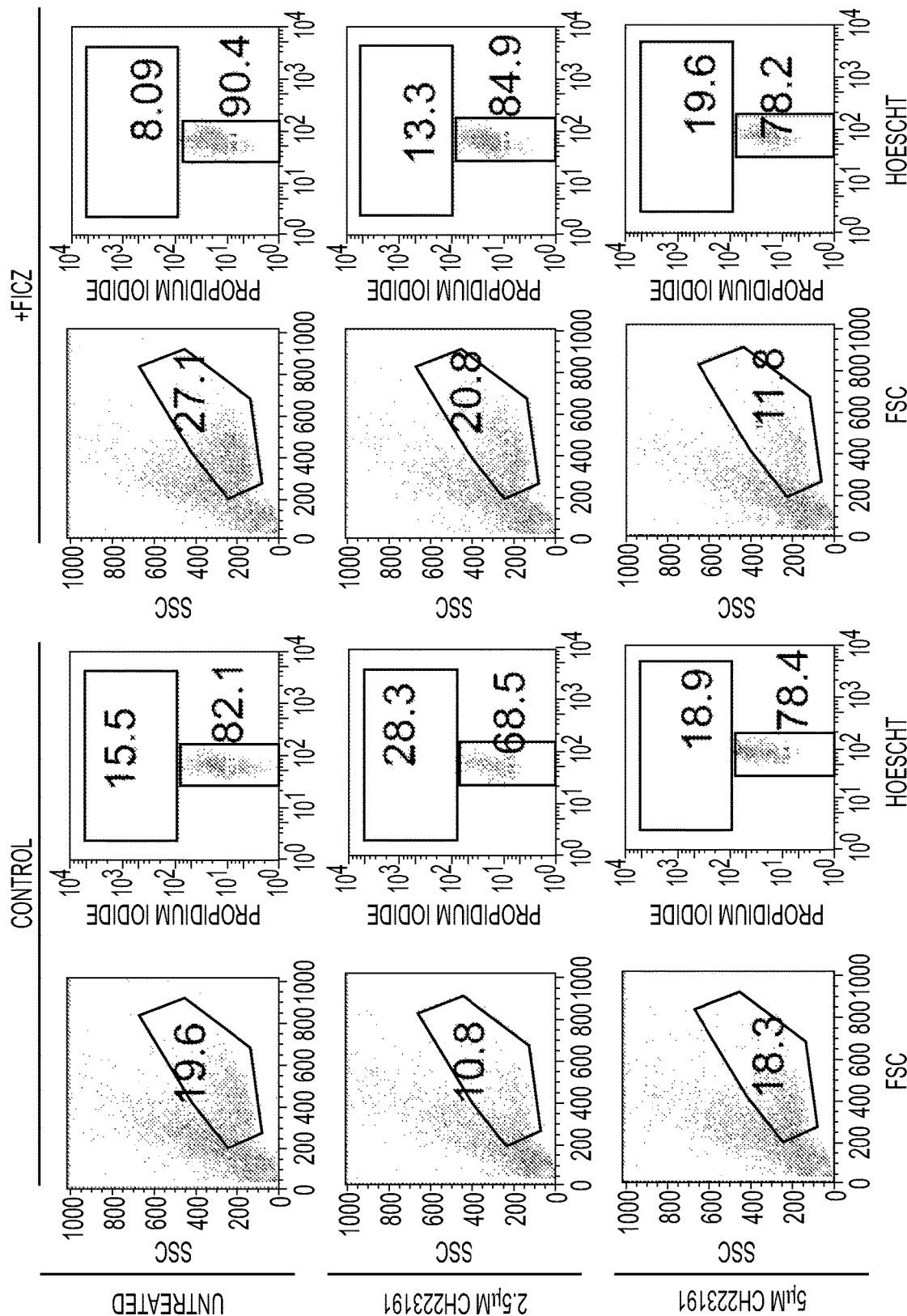
Figure 5F:
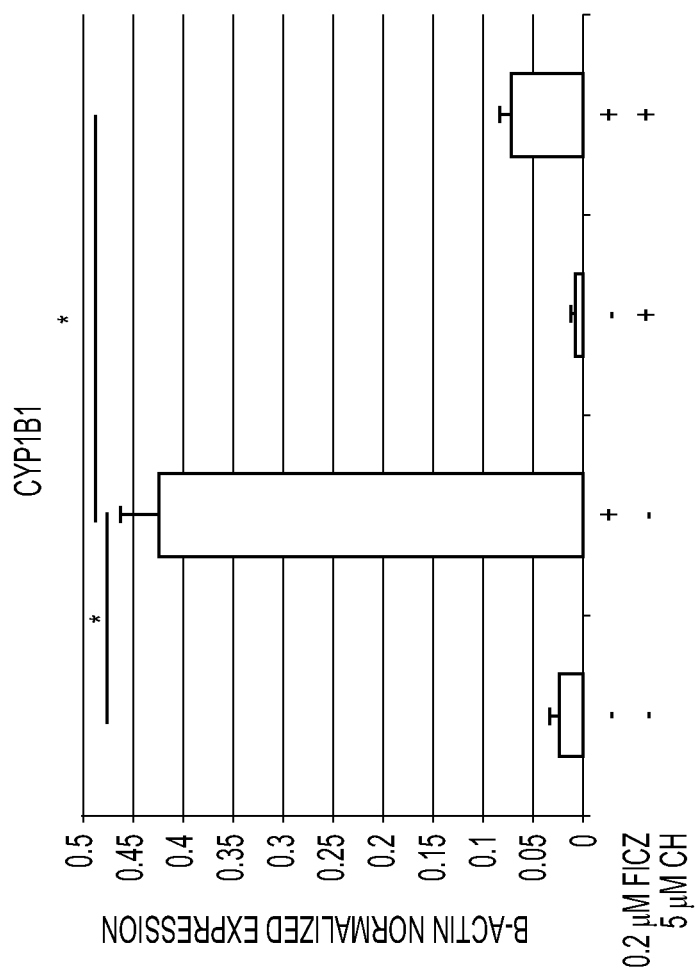

In order to determine whether FICZ-mediated transactivation of the AhR receptor was responsible for the exponential expansion of iPSC-derived MEPs, the previously described Hoecsht/Propidium Iodide apoptosis assay was performed using the known AhR inhibitor CH223191. As previously shown in FIG. 3, fewer cells stained with propidium iodide after FICZ treatment (e.g., 15.5% vs. 8.09%) (FIG. 5E). In contrast, when cells were pre-treated for 24 hours with 5 μM CH223191, the percentage of PI⁺ cells was approximately the same in vehicle or FICZ-treated cultures. No significant expansion of the CH223191+FICZ-treated cells was noted. Interestingly, when a lower dose of the inhibitor was used (2.5 μM) to pre-treat the cells before the addition of FICZ, the cells were still capable of expansion suggesting that agonist/antagonist interaction and binding of the AhR receptor in the iPSC-derived, directly differentiated MEPs is dose dependent (FIG. 5E). The efficacy of the CH223191 was confirmed by its ability to block CYP1B1 induction as assayed by qRT-PCR (FIG. 5F).

Example 6: Continuous AhR Activation Allows for Red Blood Cell Maturation while Inhibition/Antagonism Promotes Megakaryocyte Development Previous studies suggest that the AhR may play a critical role in hematopoietic cell development and function, possibly including growth and differentiation of hematopoietic stem cells. Having shown that AhR activation results in exponential expansion of MEP populations (FIG. 3), we then were in a position to determine if the AhR also contributes to MEP differentiation into RBC or megakaryocytes. Given a proposed, but not yet clearly defined role of the AhR during hematopoietic development, we conducted a series of experiments to elucidate the role of AhR in bipotential hematopoietic progenitor cells and their resultant progeny.

Figure 6A:
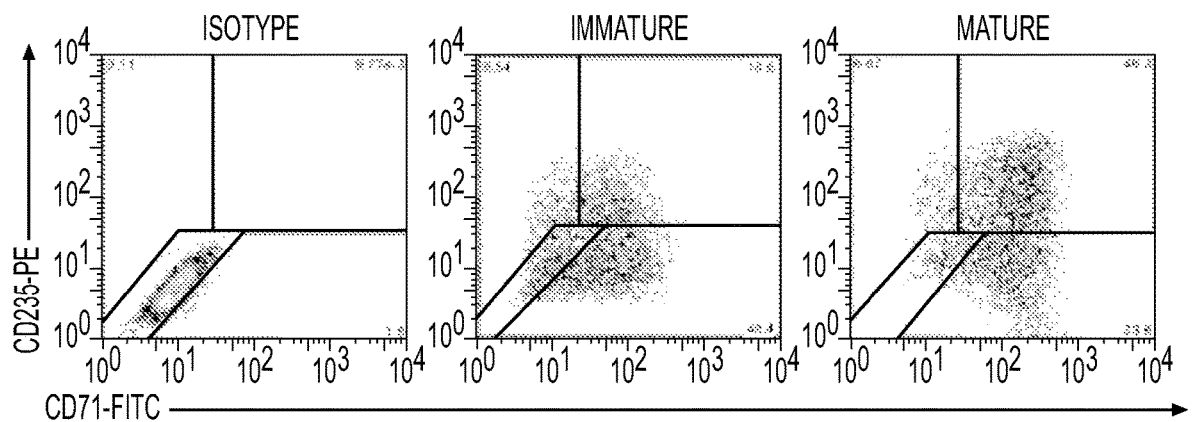
FIGS. 6A to 6J shows continuous AhR activation allows for red cell maturation while inhibition/antagonism promotes megakaryocyte development/specification. (A) Representative FACS analysis dot plots of cells co-expressing CD235-PE and CD71-FITC over time. (B) Representative FACS analysis dot plots of cells co-expressing CD235-PE and CD41-FITC. (C) Wright-Giemsa stain of immature and mature MEPs. (D) Hemoglobin expressing cell pellets of MEPs+EPO. (E) Representative FACS analysis dot plots of cells co-expressing CD235-PE and CD41-FITC+ CH223191. (F) Schematic representation of pHAGE2 lentiviral reporter construct containing the AhR repressor (AHRR) and zsGreen under control of the constitutive promoter Ef1α (pHAGE2-Ef1α-AHRR-IRES-zsGreen). (G) Representative FACS dot plots of cells infected with mock or pHAGE2-Ef1α-AHRR-IRES-zsGreen showing CD235-PE or CD41-PE expression. (H) Wright-Giemsa stain of megakaryocytes produced by AhR antagonism. (I) Ploidy analysis by FACS of the produced megakaryocytes. (J) Phase and fluorescent images of the large cells (megakaryocytes) expressing a zsGreen reporter that marks cells co-expressing the AhRR element.
Figure 6B:
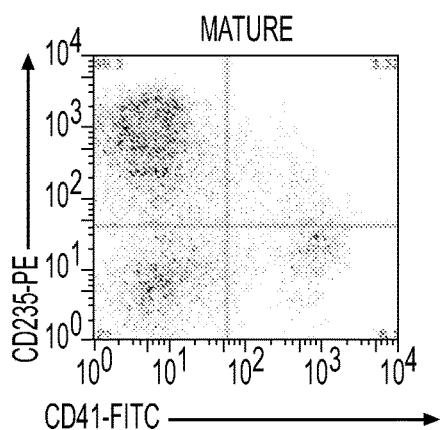
Figure 6C:
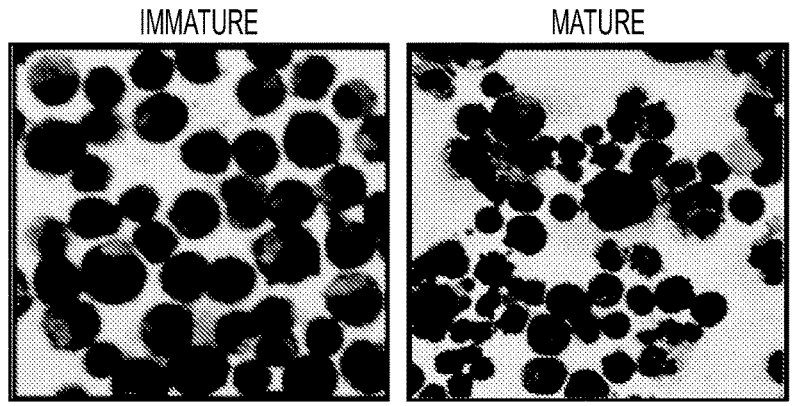
Figure 6D:
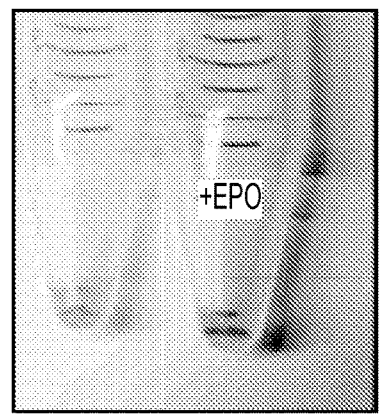

In our previous studies in which we noted exponential expansion of iPSC-derived MEPs (FIG. 3), the AhR-mediated effect that we noted allowed us to culture cells for extended periods of time (>120 days). Immunophenotyping of MEPs maintained in feeder-free conditions in the presence of FICZ revealed a progressive erythroid specification and maturation under continuous AhR agonism. As demonstrated in FIG. 6A, the majority of early passage (Day 15) iPSC-derived MEPs expressed CD71 (transferrin receptor) with a small portion of the cells also expressing CD235 (glycophorin A) suggesting an immature red cell phenotype. Under prolonged exposure to FICZ (30 days), these cells began to down regulate expression of CD71 and a larger percentage of cells expressed CD235 suggesting a more mature phenotype (FIG. 6A). As these cells continued to specify to the erythroid lineage under basal growth conditions with AhR agonism, maturation continued resulting in a more homogenous population that contained few megakaryocyte-lineage cells. This population was almost entirely CD235⁺ (FIG. 6B). These populations of iPSC-derived erythrocytes demonstrated functional maturity as assessed by their ability to respond to hypoxic conditions (FIG. 6C) and to produce hemoglobin (FIG. 6D). For example, when cultured under low oxygen (5% $O_2$) to simulate stress erythropoiesis, cells began to display hallmark characteristics of maturing erythroblasts including a reduction in cell size and the condensation of chromatin within the nuclei of the cells (FIG. 6C). More strikingly, when cells were centrifuged, bright red pellets were noted suggesting the production of hemoglobin. When additional EPO was added to the cultures, still more red cells were noted in the pellets (FIG. 6D).

Figure 6E:
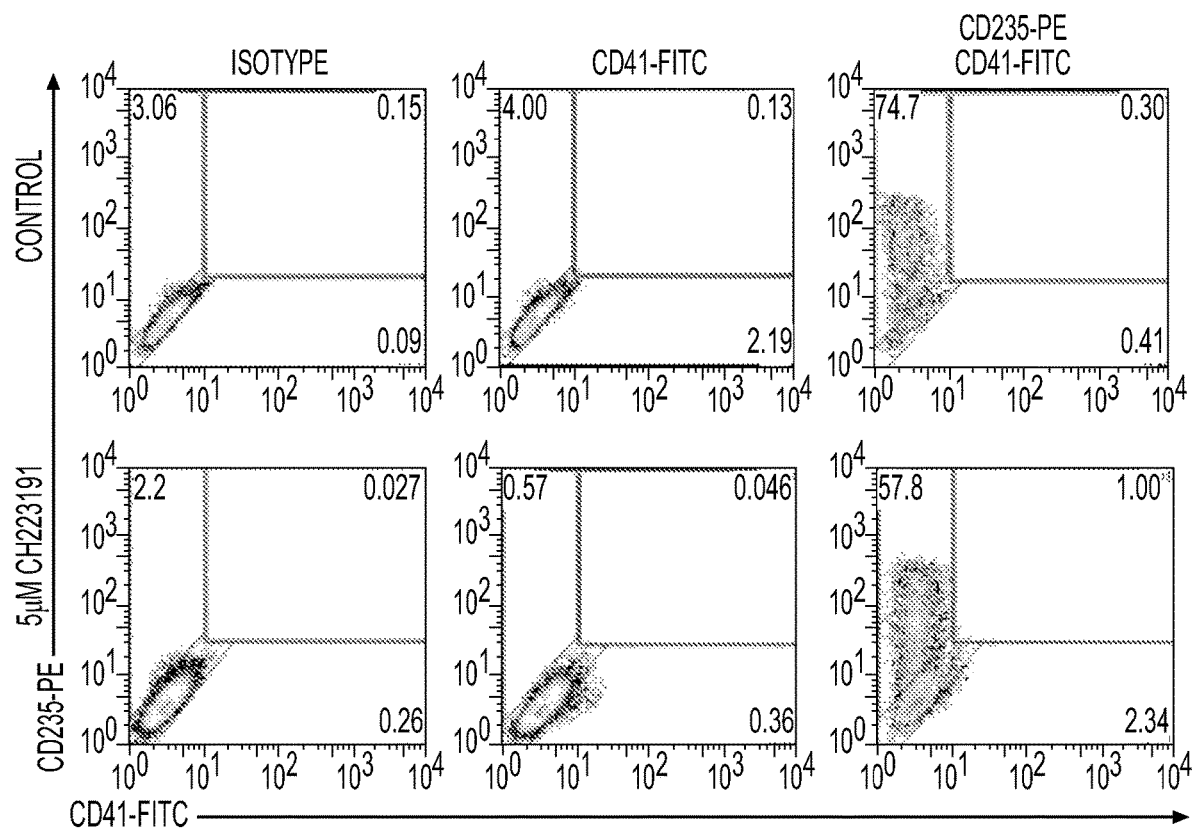
Figure 6F:
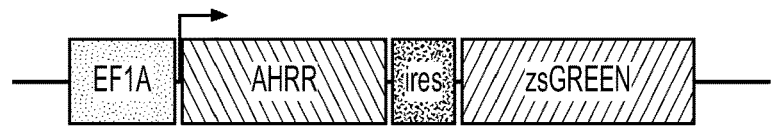
Figure 6G:
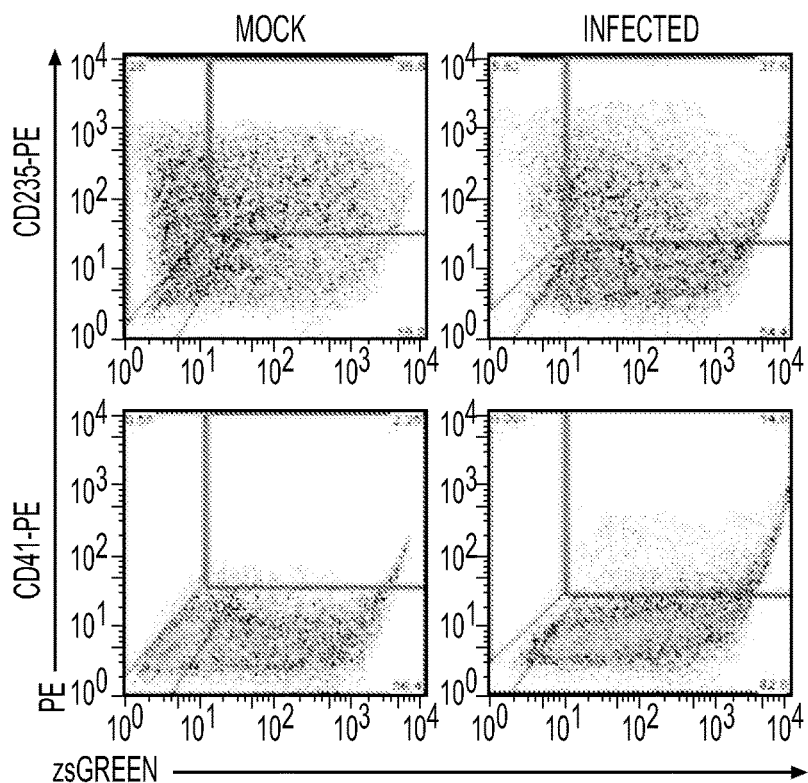
Figure 6H:
Figure 6I:
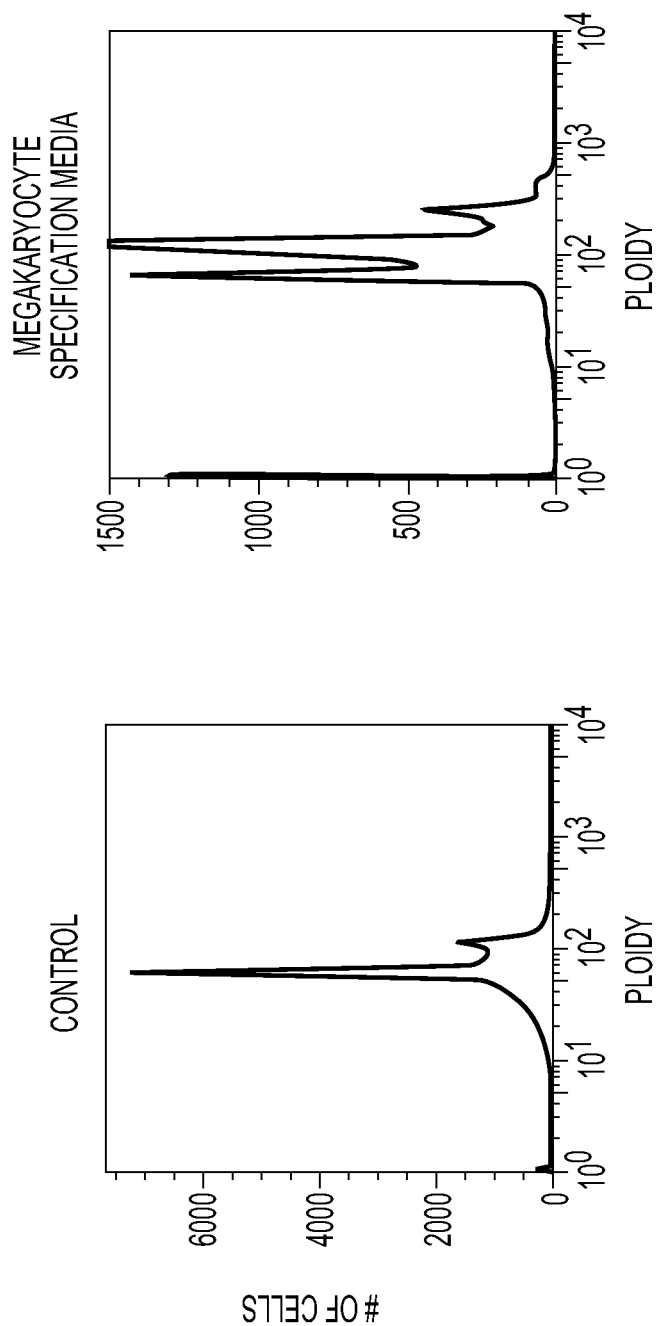
Figure 6J:
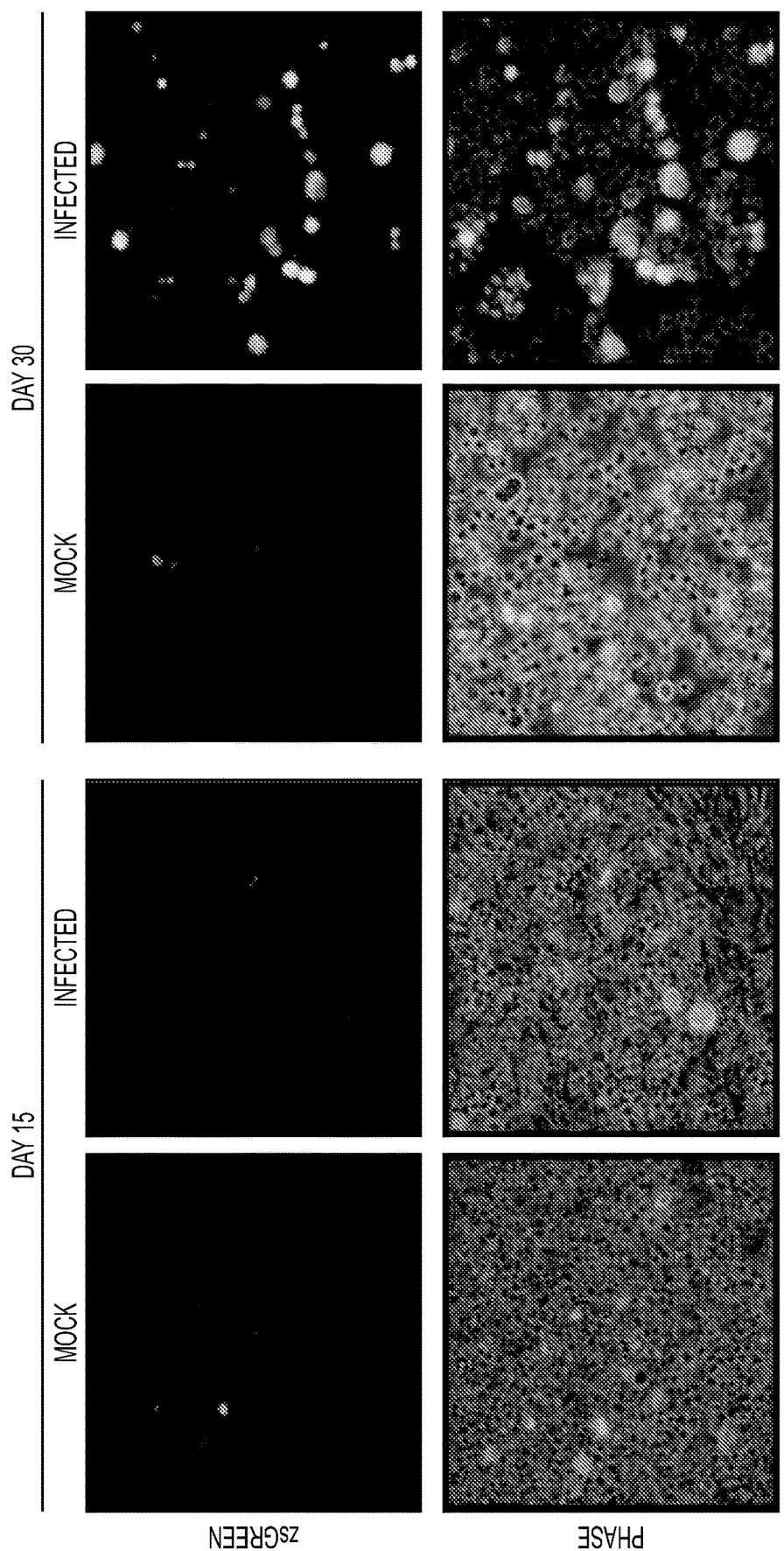

As the default pathway in our system seemed to allow for the specification and maturation of iPSC-derived MEPs into the red cell lineage under AhR agonism, we hypothesized that further AhR modulation would allow for the development of the alternative Mk lineage. To test this hypothesis, we conducted studies that allowed for AhR antagonism using both small molecule inhibition of the receptor and forced expression of an AhR repressor protein. In the first set of experiments, the known AhR antagonist CH2223191 was added to day 30 MEP populations grown in basal cytokine conditions. In contrast to vehicle-treated control populations in which virtually no CD41 positive megakaryocyte-lineage cells were noted, MEPs treated with the AhR inhibitor produced a small but defined population of CD41⁺ megakaryocyte-lineage cells (FIG. 6E). In a second set of experiments, we constructed and utilized a lentiviral vector that encoded an AhR repressor element (AhRR) along with a ZsGreen reporter (FIG. 6F). In several of our studies, this AhRR element potently and specifically inhibited either baseline or AhR agonist-induced AhR transcriptional activity (Hahn, M. E., Allan, L. L. & Sherr, D. H. Regulation of constitutive and inducible AHR signaling: complex interactions involving the AHR repressor. *Biochem Pharmacol* 77, 485-497 (2009); Evans, B. R. et al. Repression of aryl hydrocarbon receptor (AHR) signaling by AHR repressor: role of DNA binding and competition for AHR nuclear translocator. *Mol Pharmacol* 73, 387-398 (2008)). In contrast to mock-infected MEPs which were transduced with a constitutively active ZsGreen reporter only, cells infected with the AhRR lentivirus produced a significant number of CD41⁺ megakaryocyte-lineage cells (FIG. 6G). Interestingly, while the AhRR-transduced populations were capable of producing megakaryocyte-lineage cells, they also contained fewer CD235⁺ cells, suggesting that AhR antagonism in iPSC-derived MEPs initiated a transcriptional switch from erythroid to megakaryocyte-lineage specification (FIG. 6G). To further study the megakaryocyte-lineage cells produced via AhR antagonism in iPSC-derived MEPs, a discontinuous BSA gradient (0, 1.5, 3%) was used to isolate maturing Mks. Remarkably, large, CD41⁺, polyploid Mks were produced following the suppression of AhR activity via AhRR overexpression (FIG. 6H). These cells demonstrated hallmark characteristics of mature Mks including the ability to endoreplicate to 8N and 16N (FIG. 6I) and the presence of proplatelet extrusions at the surface of the cells (FIG. 6H). Furthermore, in contrast to mock-infected controls, large, AhRR-expressing Mks were noted in both early and later stage MEP cultures (FIG. 6J).

Figure 7:
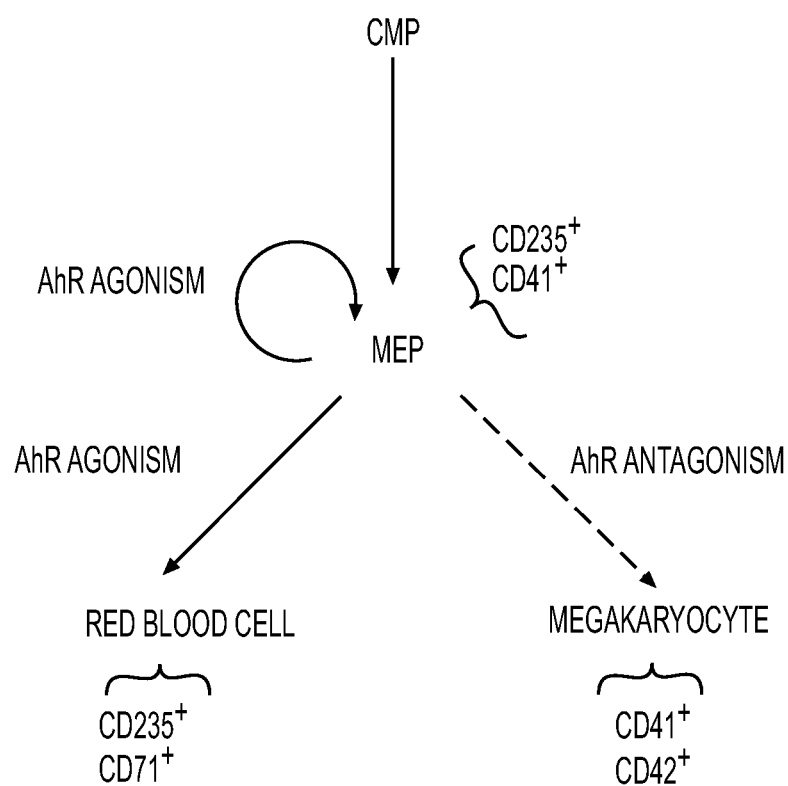
FIG. 7 shows a mechanistic diagram of AhR involvement in nominal hematopoietic development. AhR agonism allows for the production and expansion of a megakaryocyte erythroid progenitor (MEP) population. Continued AhR agonism is permissive for red cell development whereas AhR antagonism preferentially directs the MEPs to become megakaryocytes.

FIG. 7 presents a mechanistic diagram of the role of AhR agonism in the differentiation and expansion of MEPs and the roles of AhR agonism and antagonism in the differentiation of RBCs and megakaryocytes from MEPs.

Example 7: Characterization of iPSC-Derived RBCs

Figure 8A:
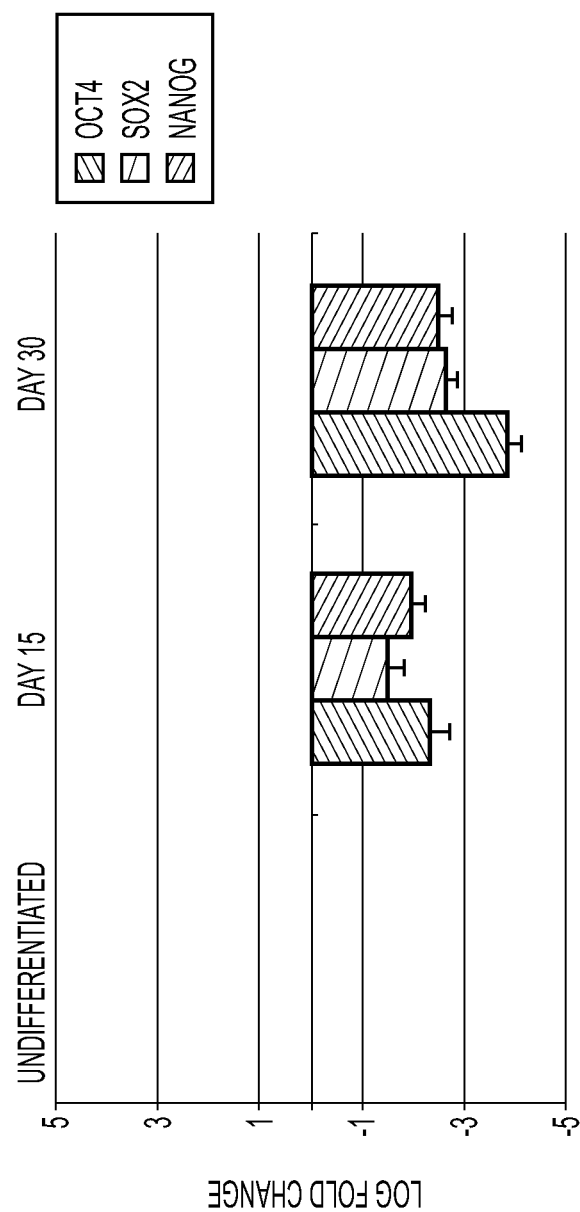
FIGS. 8A and 8B shows the expression of genes involved in the reprogramming of iPSCs and the genes involved in RBC differentiation. (A) embryonic genes (including those such as Oct4, Sox2, and Nanog that are responsible for the reprogramming process are downregulated as cells are directly differentiated into RBCs. (B) At days 15 and 30 of erythroid specification in this directed differentiation system the cells exhibit a complementary heavy upregulation of genes of critical import to RBCs.

Expression of genes involved in reprogramming of iPSCs and genes involved in RBC differentiation were analyzed to further characterize iPSC-derived RBCs made according to the methods of Example 6. The results show that embryonic genes (including those such as Oct4, Sox2, and Nanog that are responsible for the reprogramming process are downregulated as cells are directly differentiated into RBCs (FIG. 8A and data not shown).

Figure 8B:
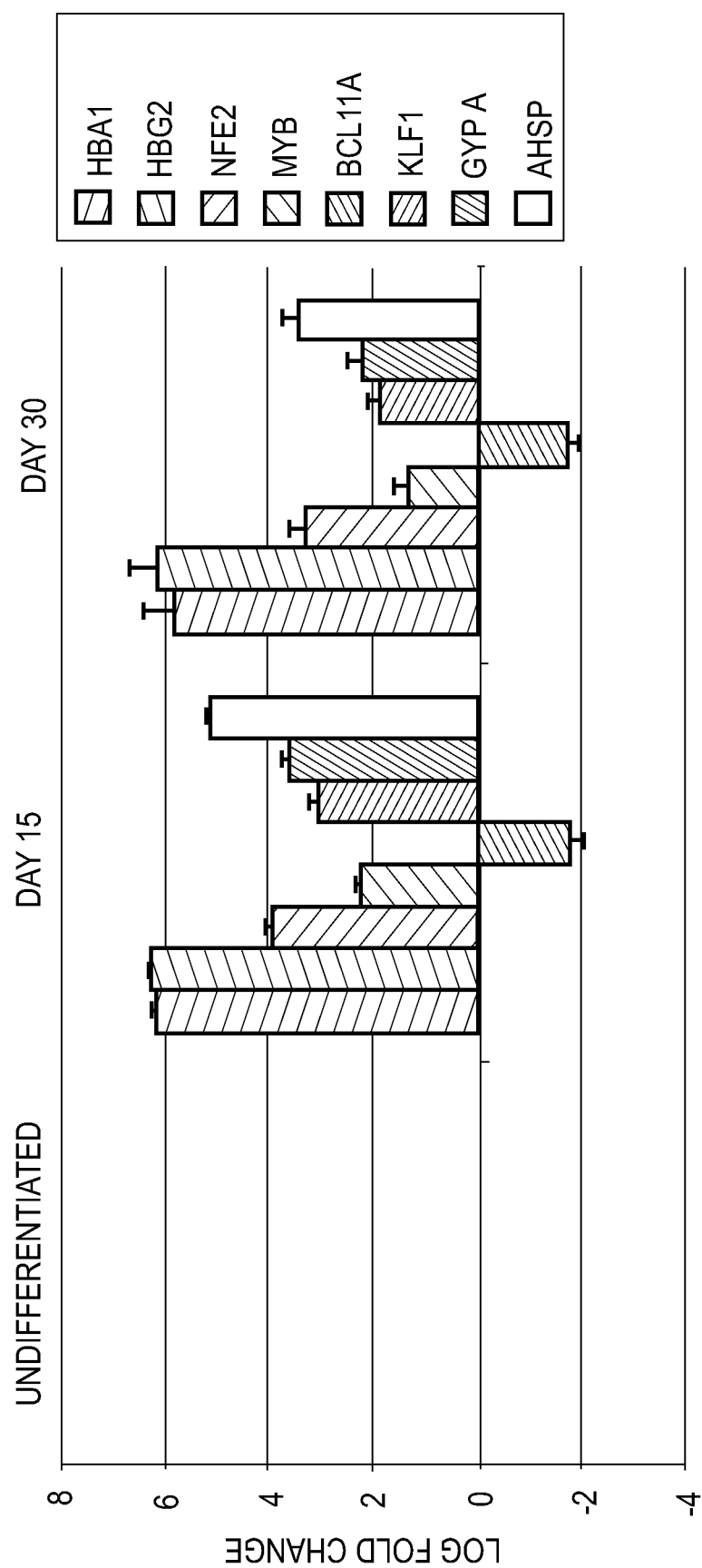

At days 15 and 30 of erythroid specification in this directed differentiation strategy the cells exhibit a complementary upregulation of genes of critical import to the RBCs (FIG. 8B).

By microarray analysis, Day 15 and Day 30 iPSC-derived RBCs upregulate a panel of hemoglobins (alpha 1 and gamma 2), and other genes involved in the regulation of the erythroid-lineage (p45, NFE2; c-Myb; Kruppel-like factor 1, KLF-1; alpha hemoglobin stabilizing protein, AHSP; and CD235, Glycophorin A. In addition, BCL-11A is downregulated upon differentiation which is commensurate with erythroid maturation.

Example 8: Characterization of iPSC-Derived RBCs

In normal hematopoietic development, embryonic globins (epsilon and zeta) are expressed early on in development and downregulated pre-birth. Alpha globin is expressed at high levels both pre and post birth. Fetal hemoglobin (gamma) is expressed at high levels pre-birth, and is rapidly downregulated (with less than 5% expressed by 5 years of age. Adult globin (beta) is expressed reciprocally with fetal hemoglobin, and is the predominant form of hemoglobin expressed in adult cells. Importantly, the ability to increase fetal hemoglobin in an adult ameliorates the symptomology of sickle cell anemia.

Figure 9A:
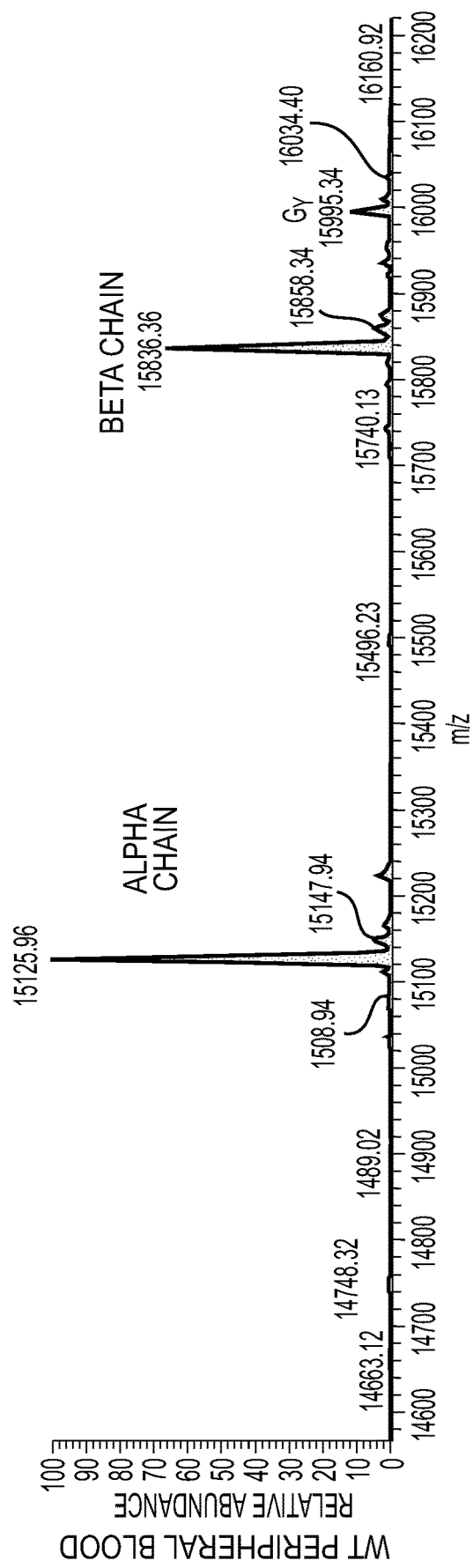
FIGS. 9A and 9B shows mass spectrophotometric analyses of globin gene expression in human whole blood. Analyses of whole peripheral blood of a control patient (A) and a patient suffering from sickle cell disease (9B) is shown.
Figure 9B:
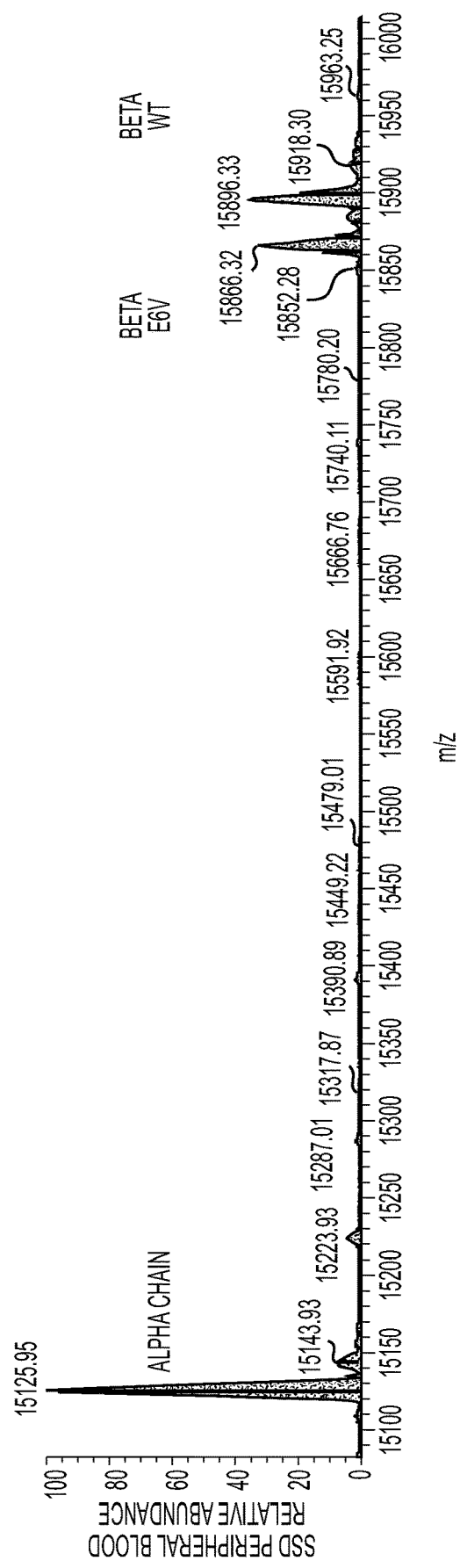
Figure 10:
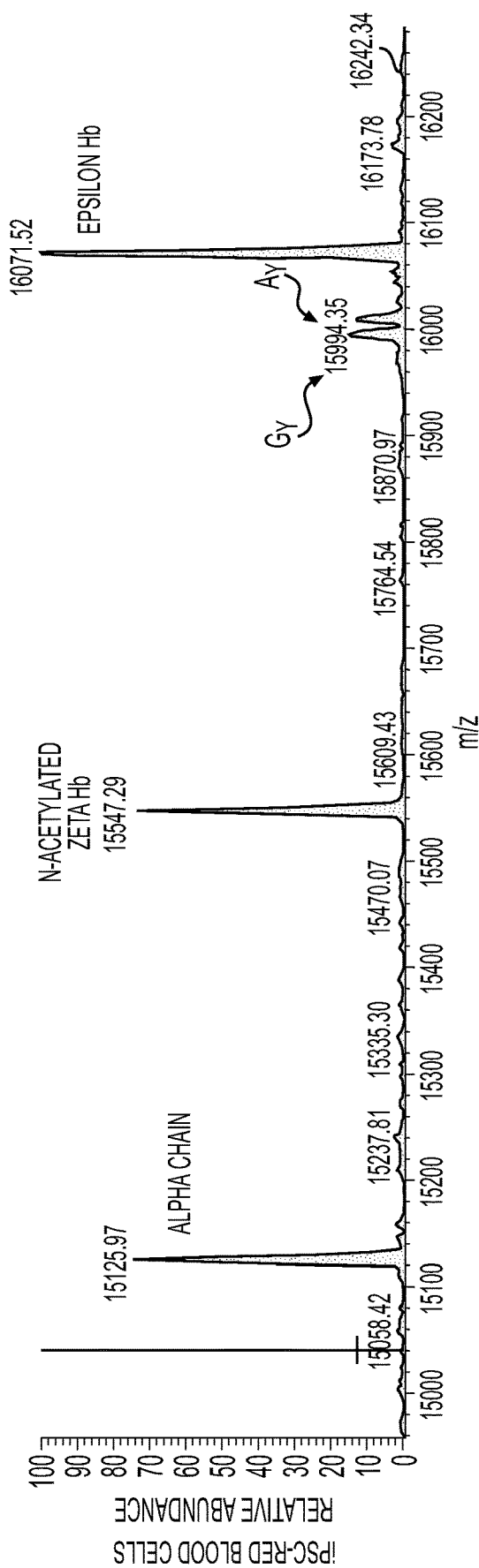
FIG. 10 shows mass spectrophotometric analyses of globin gene expression in iPSC-derived RBCs made by methods of this disclosure.

We utilized mass spectrophotometric analyses to study the types of globins that are being produced by iPSC-derived RBCs using the methods of this disclosure. In FIG. 9, results of the analyses of whole peripheral blood of a control patient (FIG. 9A) and a patient suffering from sickle cell disease (FIG. 9B). Clear peaks for alpha globin, gamma globin, and beta globin (adult globin) are evident. In the sickle cell patient the mutation that produces sickle cell (hemoglobin S) is clearly visible (FIG. 9B). The results of a similar analysis of day 30 iPSC-derived RBCs is shown in FIG. 10. The predominantly expressed proteins are the globins. The cells clearly express alpha robustly. Interestingly, the cells are apparently at an embryonic/fetal stage of differentiation, in that they express both embryonic globins (epsilon and zeta) as well as fetal (gamma; there are two peaks here as there are two isoforms of gamma), but no adult globin (beta). iPSC-derived RBCs have not been previously analyzed in this manner, and these mass spectrophotometric analyses provide evidence that the cells express the appropriate genes at the protein level.

Example 9: iPSC-Derived RBCs Respond to HbF Inducers

Figure 11:
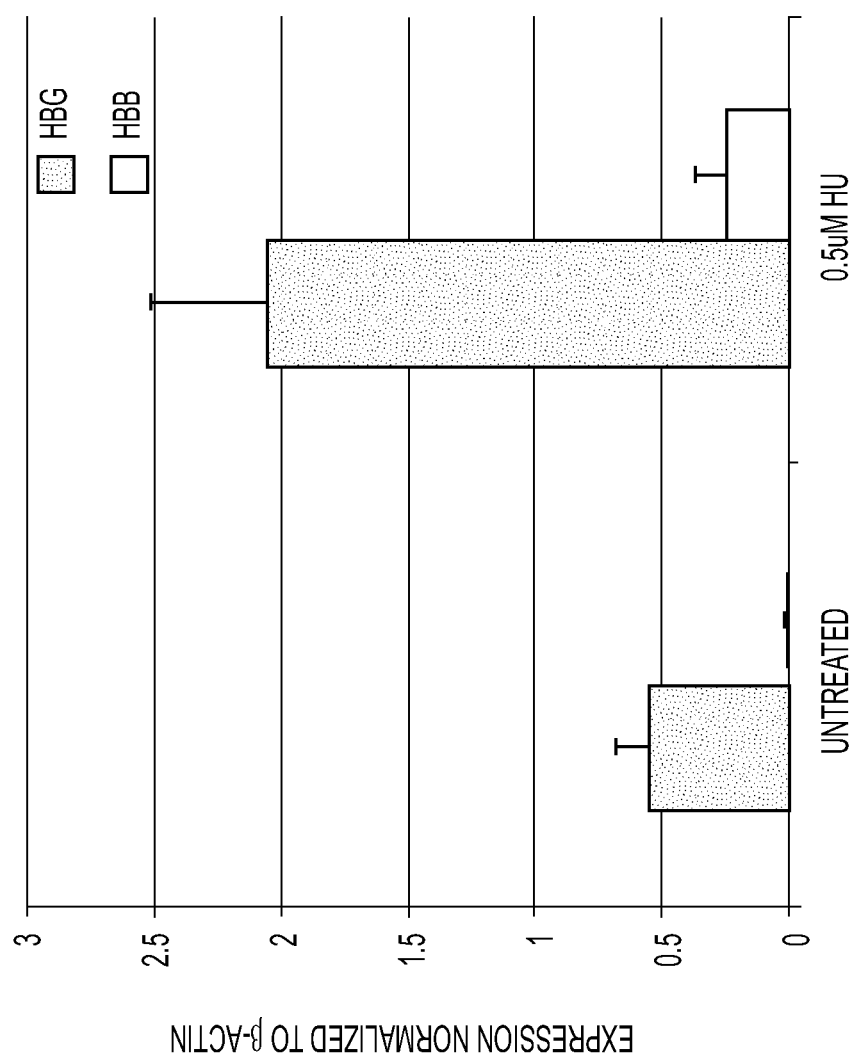
FIG. 11 shows that exposure of iPSC-derived RBCs to 0.5 μM hydroxyurea HU causes an approximately 4-fold increase in expression of fetal hemoglobin (HbF; gamma) indicating that iPSC-derived RBCs are responsive to HbF inducers.

The ability to increase fetal hemoglobin in an adult ameliorates the symptomology of sickle cell anemia. Hydroxyurea (HU) is the only FDA-approved drug that does this, presumably by initiating stress erythropoiesis (this is a process by which new red cells are rapidly birthed under stress; as they are recently emerged RBCs they express a bit more fetal hemoglobin). As discussed above, our iPSC-derived RBCs already express fetal hemoglobin, so the question arose as to whether or not the cells would be responsive to HU (and could therefore be used as a patient-specific screening platform for novel inducers of HbF). As shown in FIG. 11, exposure of iPSC-derived RBCs to 0.5 µM HU causes a 4-fold increase in expression of fetal hemoglobin (gamma) (HBG in FIG. 11). This data illustrates the fact that the cells are indeed responsive to therapeutic doses of HU.

Figure 12:
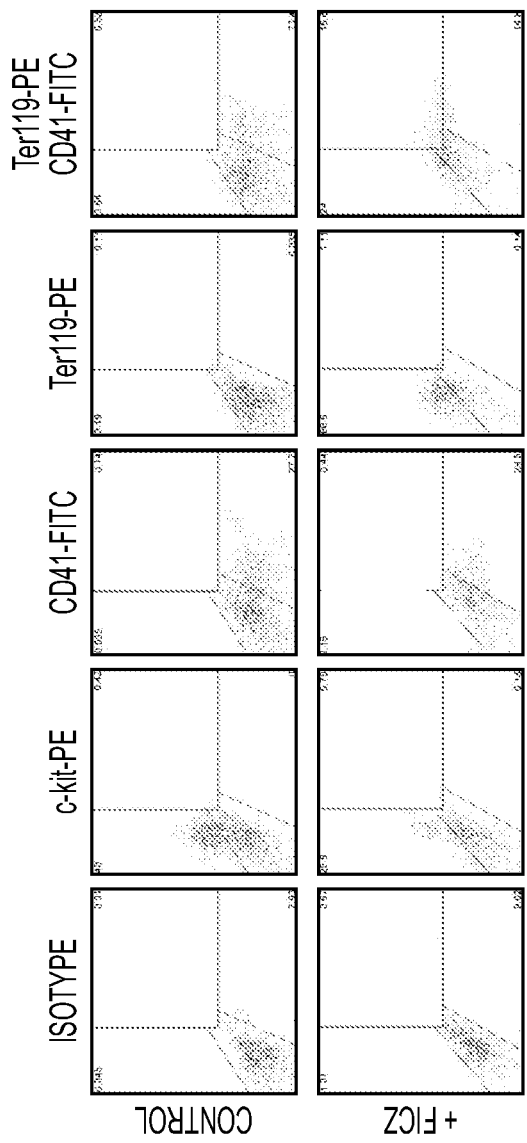
FIG. 12 shows that AhR agonism promotes MEP production and expansion in murine bone marrow. Representative FACS analysis dot plots of red cell depleted C57B6 bone marrow grown for 3 days in +/−0.2 μM FICZ. 1×10^5 cells were initially treated with CD16/32 Fc receptor block, followed by directly conjugated monoclonal antibodies for the designated markers.

Example 10: AhR Agonism Promotes MEP Production and Expansion in Murine Bone Marrow To determine if AhR agonism would result in MEP production and expansion from bone marrow precursors (as opposed to iPSCs) in a murine system, red cell-depleted, bone marrow from C57BL/6 mice was cultured for 3 days in the presence or absence of vehicle or 0.2 µM FICZ. Remarkably, in contrast to vehicle-treated controls, distinct populations of primary, CD41$^+$/Ter119$^+$ MEPs were noted in the cultures following just 3 days of FICZ treatment (FIG. 12).

Example 11: iPSC-Derived Mks Upregulate Key Megakaryocyte-Specific Genes

Figure 14:
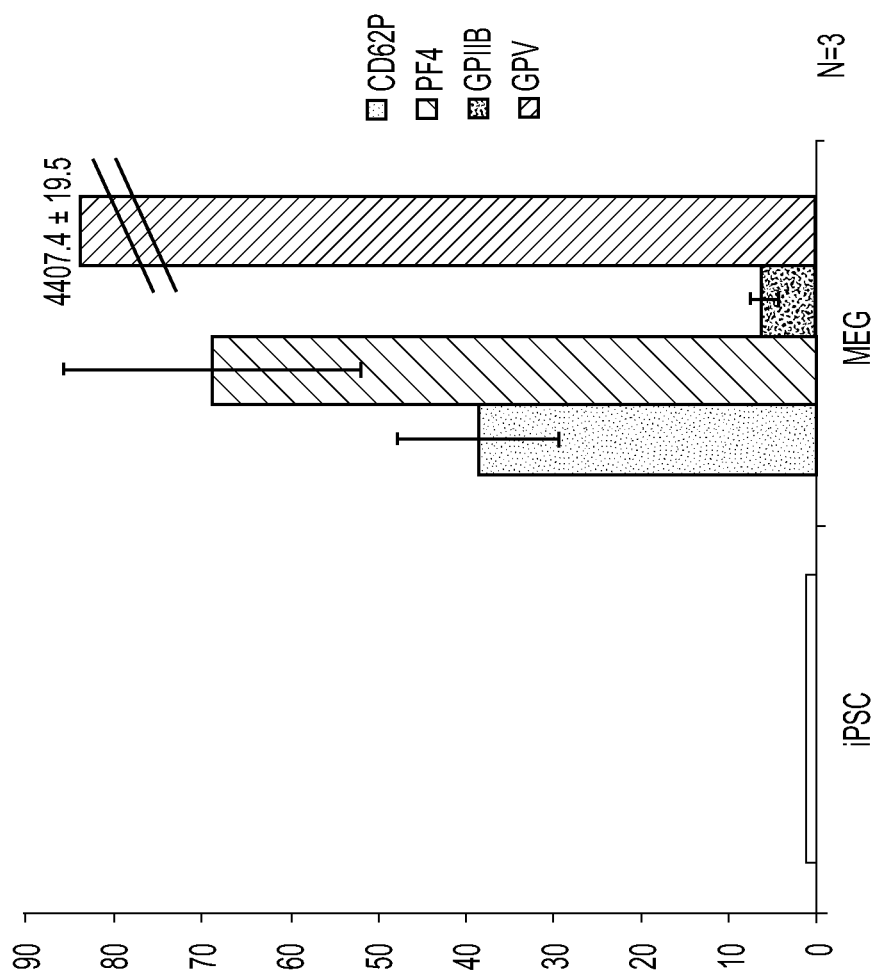
FIG. 14 shows that iPSC-Mks, created using AhR antagonism, express a series of hallmark and characteristic MK markers.

To further characterize iPSC-derived Mks made according to methods of this disclosure Quantitative PCR analysis was performed following purification using a discontinuous BSA gradient. iPSC-Mks, created using AhR anatagonism, express a series of hallmark and characteristic MK markers. (FIG. 14). By quantitative PCR analysis, these cells express hallmark and characteristic MK markers such as CD62P (P-selectin), Platelet Factor 4 (PF4), GPIIb, and GPV.

Example 12: iPSC-Derived Mks Produce Functional Platelets

Figure 15:
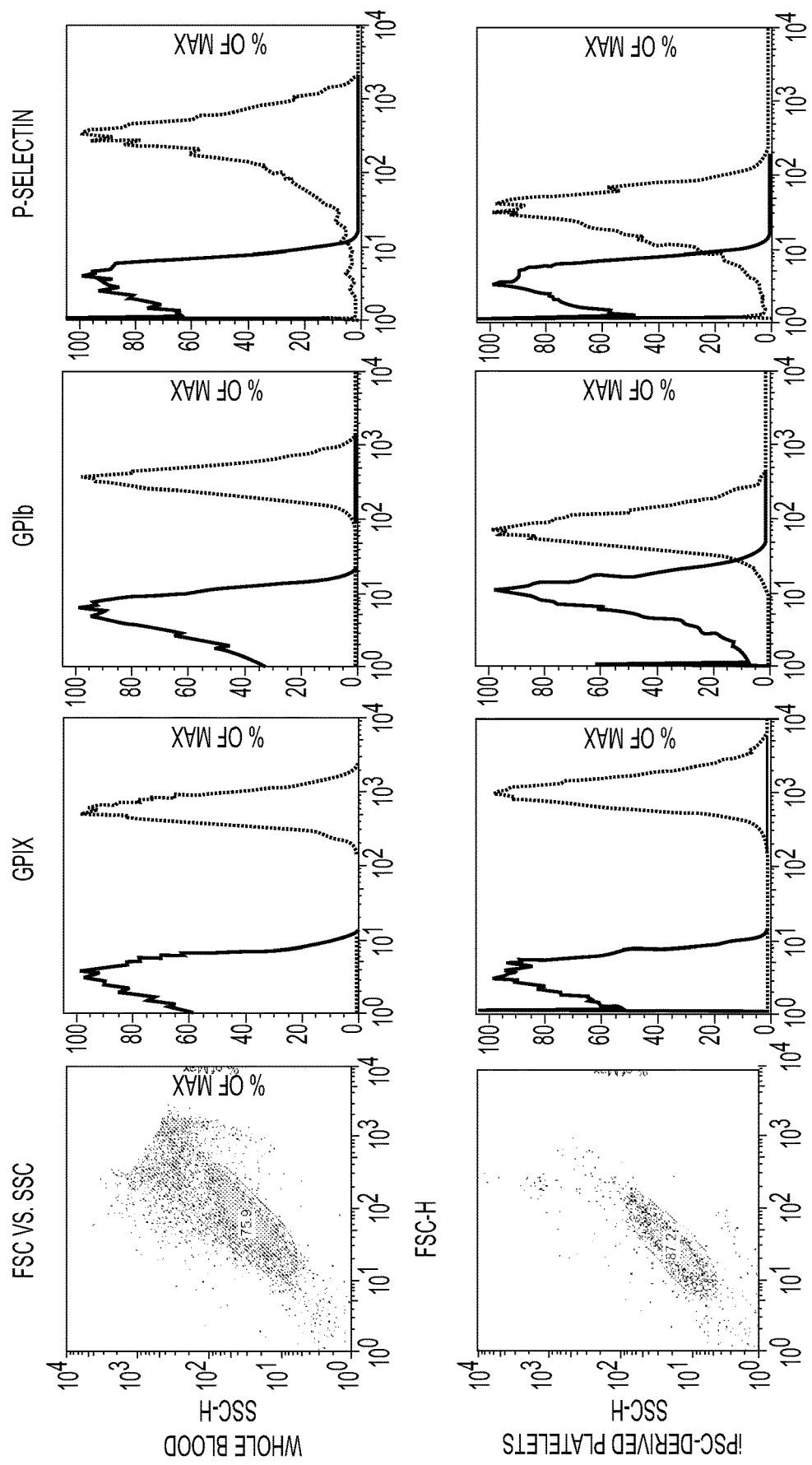
FIG. 15 shows that iPSC-derived platelets are remarkably similar to those derived from whole blood.

Flow cytometry was used to compare platelets from whole blood and iPSC-derived platelets. The results reveal that iPSC-derived platelets are remarkably similar to those derived from whole blood. The FSC vs. SSC profile is extremely similar, and iPSC-derived platelets express the hallmark platelet markers GPIX, GPIb, and P-Selectin. (FIG. 15).

Figure 16A:
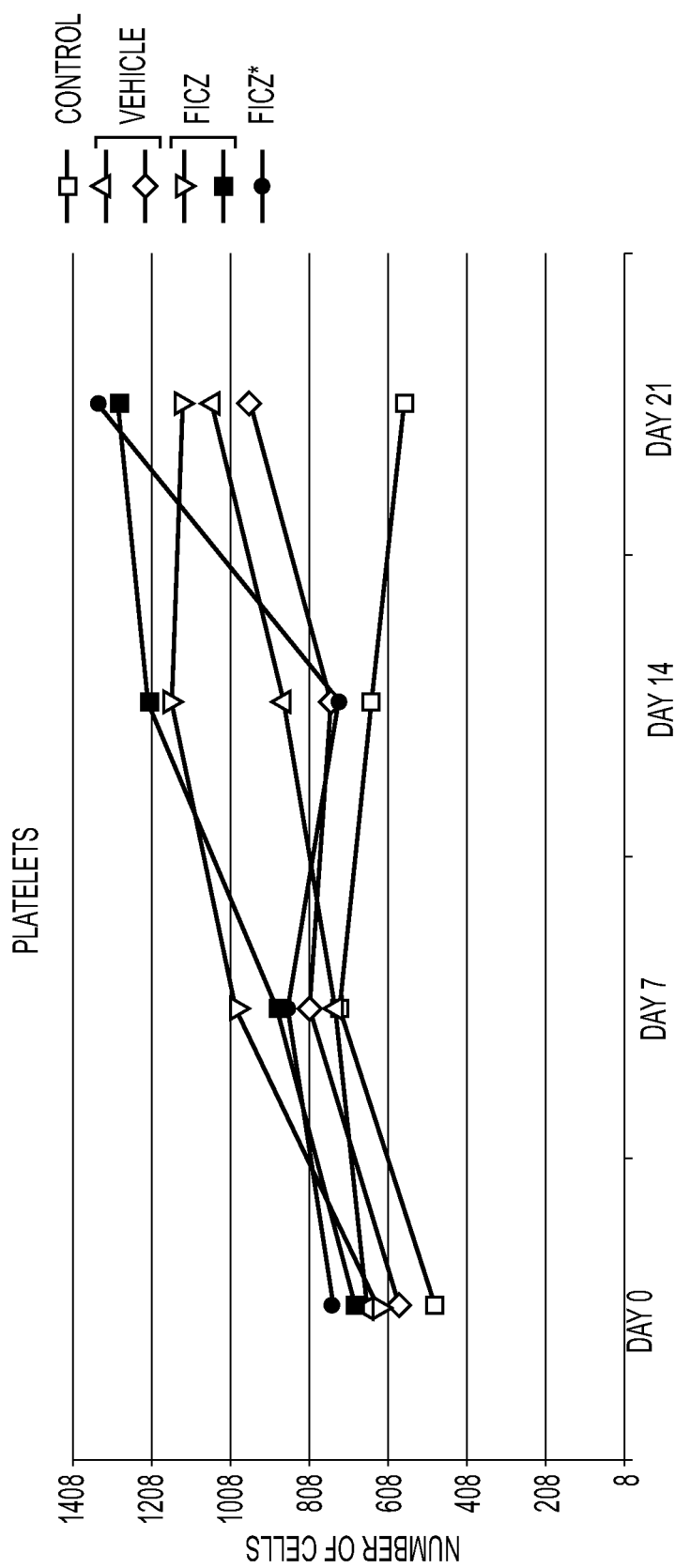
FIGS. 16A to 16C shows that AhR agonist FICZ is active in vivo and results in increased platelet counts in normal mice. (A) C57B6 mice were injected daily intraperitoneally with FICZ suspended in vegetable oil using a weekly dose escalation scheme (Week 1: 1 mg/kg; Week 2: 2 mg/kg; Week 3: 4 mg/kg). Hemavet quantification of peripheral blood bleeds were done at 3 time points (Day 7, 14, and 21) Interestingly, a mouse that was immediately exposed to higher doses of FICZ and did not undergo week 1 escalation demonstrated a more immediate and prolific platelet response. (B) Following the 3 week time point, mice were sacrificed and their livers were harvested for quantitative RT-PCR analysis for CYP1B1 target gene expression. (C) Following the 3 week time point, mice were sacrificed and their spleens were harvested for quantitative RT-PCR analysis for CYP1B1 target gene expression.
Figure 16B:
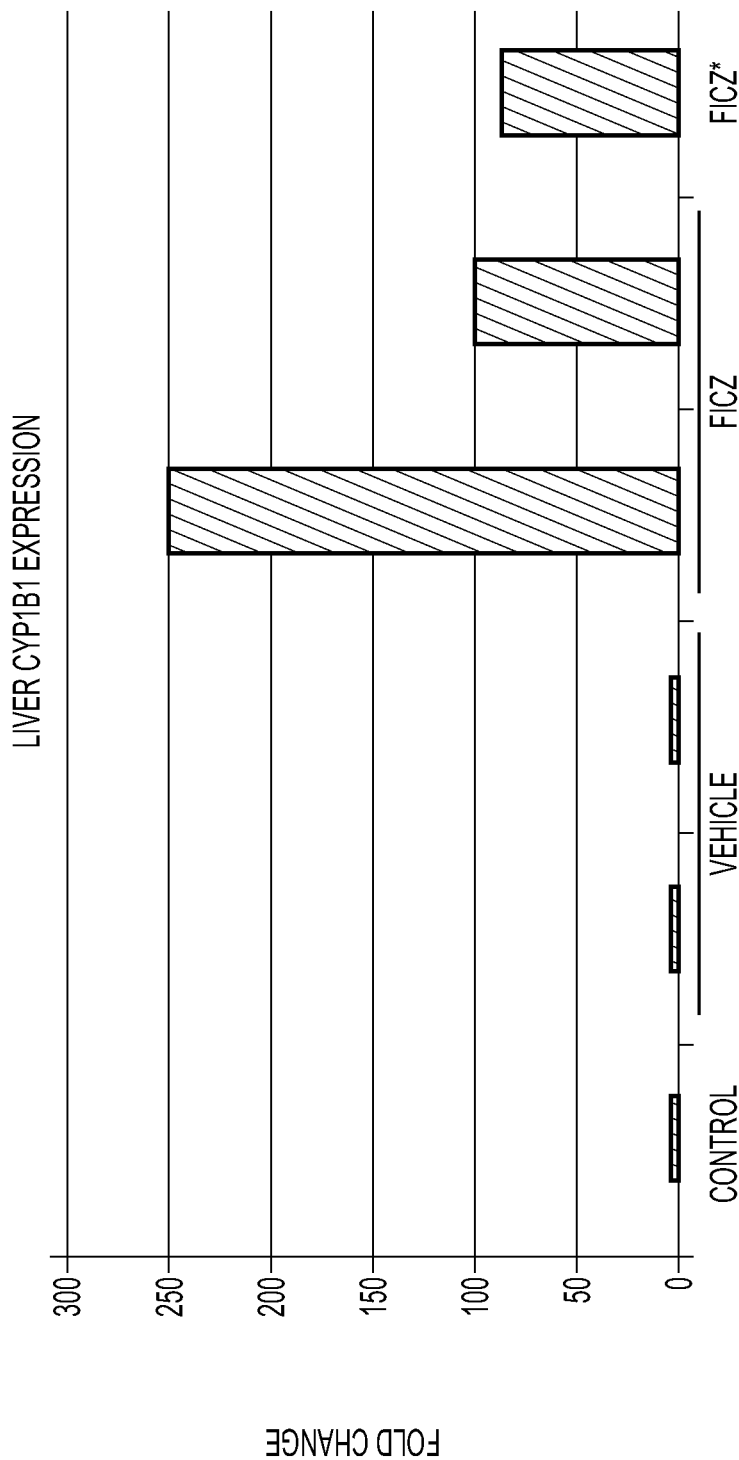
Figure 16C:
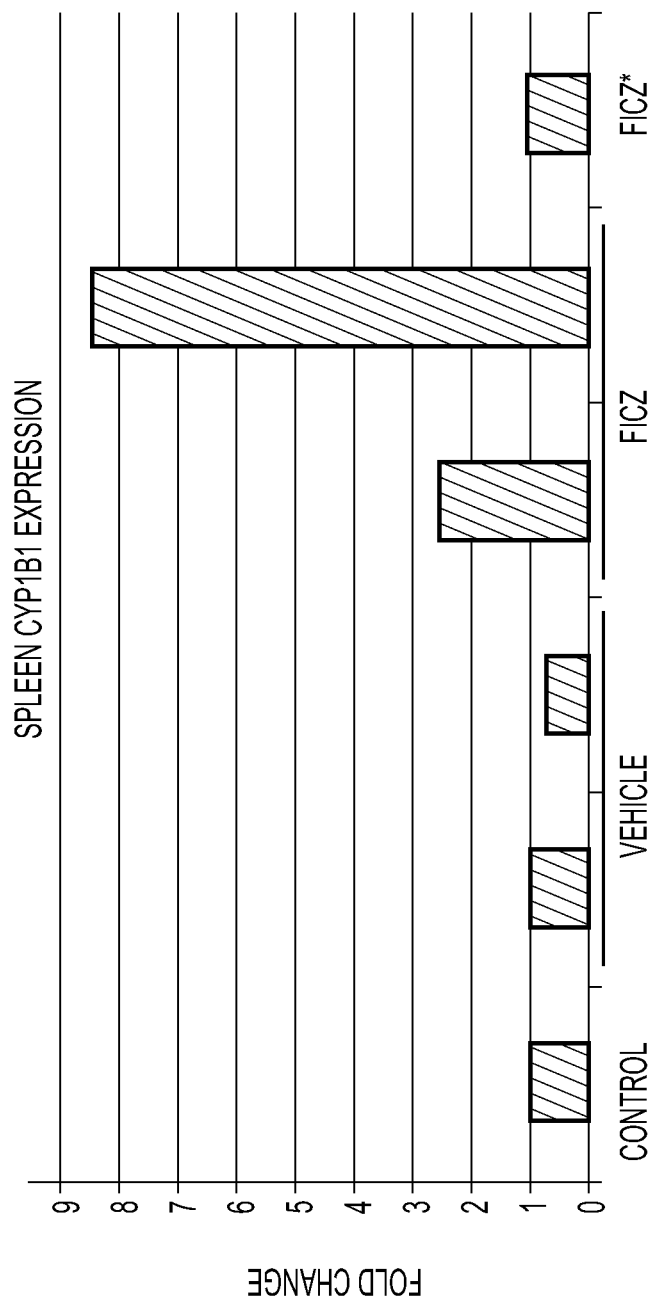

Example 13: The AhR Agonist FICZ is Active In Vivo and Results in Increased Platelet Counts in Normal Mice To determine if FICZ treatment or whole animals would affect RBC or platelet production, C57Bl6 mice were injected daily intraperitoneally with FICZ suspended in vegetable oil using a weekly dose escalation scheme (Week 1: 1 mg/kg; Week 2: 2 mg/kg; Week 3: 4 mg/kg). In contrast to mock-injected mice or mice injected with vehicle only, mice injected with FICZ showed increased platelet counts, as assayed by Hemavet quantification of peripheral blood bleeds, at all 3 time points (Day 7, 14, and 21) (FIG. 16A). Interestingly, a mouse that was immediately exposed to higher doses of FICZ (4 mg/kg) and did not undergo week 1 escalation demonstrated a more immediate and prolific platelet response. None of the mice in the study showed significant variations in either white blood cell (WBC) or red blood cell (RBC) counts (not shown). Following the 3 week time point, mice were sacrificed and livers and spleens harvested. Quantitative RT-PCR analyses for CYP1B1 target gene expression revealed robust upregulation in the liver and spleen of FICZ treated animals confirming that we had reached biologically meaningful FICZ doses in vivo (FIGS. 16B and 16C).

Figure 17:
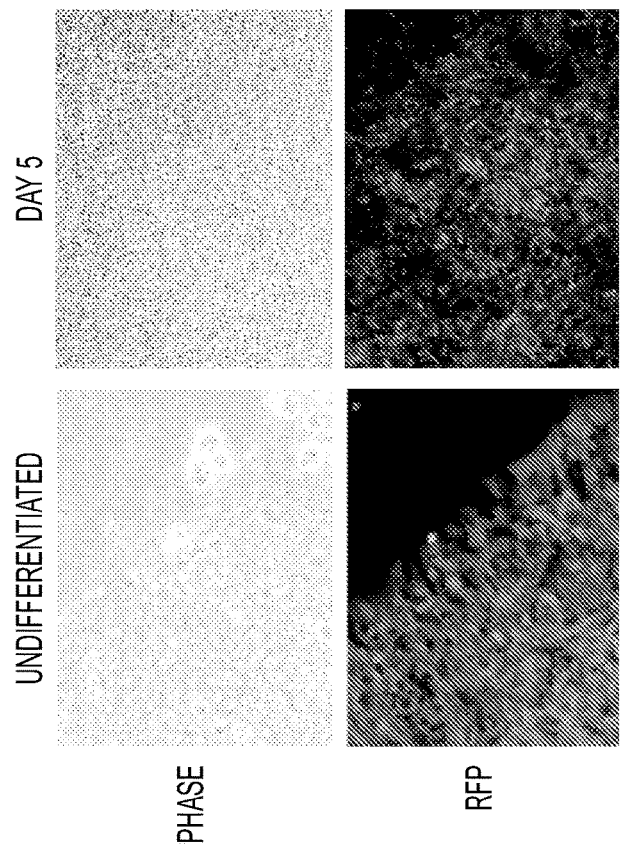
FIG. 17 shows a short hairpin RNA (RNAi) for AhR construct (bottom) which can be turned on in undifferentiated and differentiating iPSCs (top).
Figure 17:
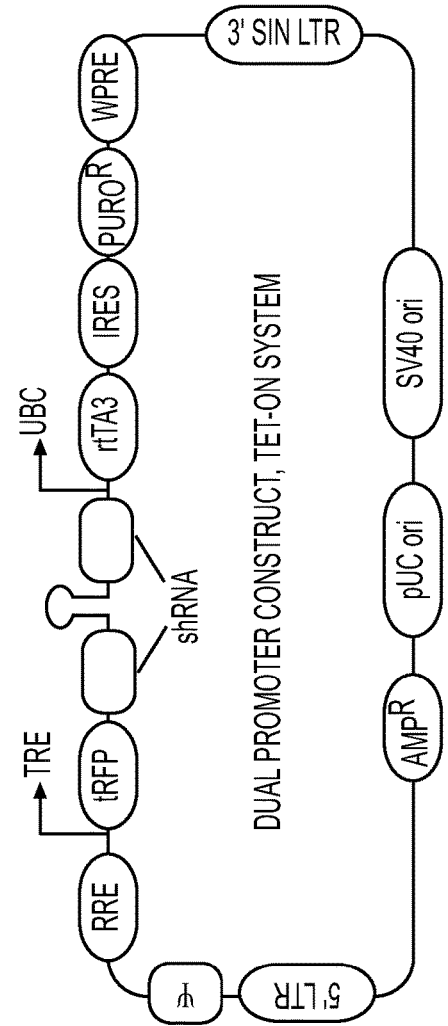

Example 14: AhR Inhibition in iPSC Cells iPSC cell lines were produced that allow selective down-regulation of expression of AhR using a molecular approach. FIG. 17 shows the construct used, which contains a short hairpin RNA (RNAi) for AhR which is expressed when the cells are treated with a doxicycline inducer. A red florescent reporter is also turned on to track the expression. The top panel of FIG. 17 shows that the RNAi can be turned on in the undifferentiated cells and at Day 5 of the differentiation.

Figure 18:
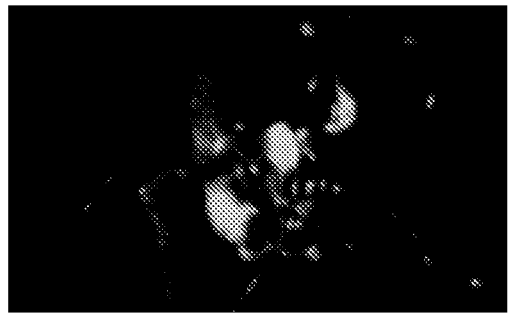
FIG. 18 shows that activation of the construct in Mks causes a dramatic increase in proplatelet formation.
Figure 18:
Figure 18:
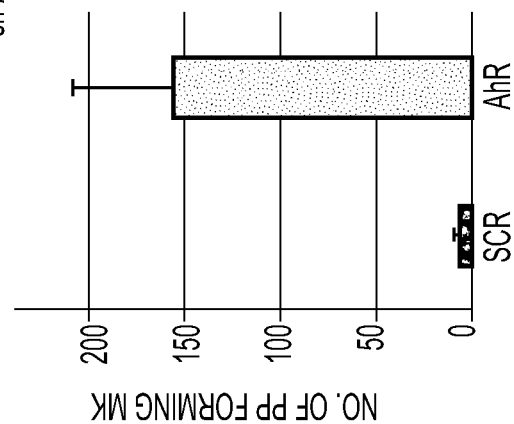
Figure 18:
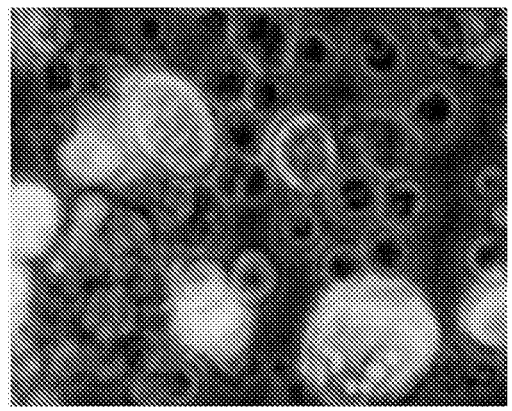

The RNAi for AhR was activated in end stage MKs made using the techniques of this disclosure. The result is an increase in production of proplatelets compared to control cells expressing a scrambled RNAi sequence (SCR). Images of the fluorescent reporter are shown in FIG. 18 (top) and the dramatic increase in proplatelet formation is presented graphically (FIG. 18 (bottom)).

This result demonstrates that inhibition of AhR in Mks increases platelet maturation from Mks. Thus, AhR antagonism drives MEPs to differentiate into Mks and then also acts to promote differentiation of Mks into platelets.

DISCUSSION

Our results indicate that AhR has a physiological and functional role in nominal hematopoietic development, and that modulation of the receptor in bi-potential hematopoietic progenitors can direct cell fate. We demonstrate a novel methodology for the directed differentiation of pluripotent stem cells in serum and feeder-free defined culture conditions into MEPs capable of final specification into Mks and/or erythroid-lineage cells.

As a starting point for these studies, we utilized human hematopoietic cell differentiation genomic (dMap) array data as a roadmap for assessing the possible role of AhR in hematopoietic cells. These analyses were a powerful tool that suggested that the AhR plays an important role in blood cell development and were consistent with previous studies and the considerable amount of data presented here.

Although several teams have published proof-of-principle examples for the derivation of hematopoietic cells from ESC and iPSC these protocols are technically demanding and result in the production of limited numbers of cells. Our conceptual approach has been to mimic the natural sequences of development in vitro in order to derive the range and number of cell types needed for the creation of a robust iPSC-based platform. This protocol utilizes a relatively simple 2D culture approach and eliminates the need for embryoid body formation, often a problematic step when using human pluripotent stem cells. Furthermore, this protocol is short (~10 days), completely chemically defined, and requires no xenobiotic feeder cells or growth factors thereby making GMP production and clinical translation feasible.

Importantly, we have also found that the use of a non-toxic aryl hydrocarbon receptor agonist in our directed differentiation scheme dramatically increases the number of MEPs and resultant cells. This is an extremely important finding in that traditionally, the evolutionarily conserved AhR has been studied for its role in environmental chemical-induced toxicity, and in our system it is shown to be intricately involved in the growth and the differentiation of at least two crucial blood cell types. Following the addition of the potent AhR ligand FICZ to our cultures, we observed exponential expansion of MEPs from a few thousand to a billion cells in a few weeks. Importantly, the role of AhR in the MEP population was confirmed using a highly specific AhR inhibitor. This logarithmic expansion of cells appears to be a function of decreased cell death and is consistent with previous studies which suggest that the AhR can control apoptosis.

Interestingly, FICZ, the AhR ligand utilized throughout this work, is a photo-metabolite of tryptophan originally described by Rannug and colleagues (Rannug, U. et al. Structure elucidation of two tryptophan-derived, high affinity Ah receptor ligands. *Chem Biol.* 2, 841-845. (1995)). Based on previous studies demonstrating the ubiquity of FICZ (Wincent, E. et al. The suggested physiologic aryl hydrocarbon receptor activator and cytochrome P4501 substrate 6-formylindolo[3,2-b]carbazole is present in humans. *J Biol Chem* 284, 2690-2696 (2009)) and taken together with our data demonstrating the in vivo activity of this ligand, it is not inconceivable that FICZ plays a role in regulating hematopoiesis in vivo, possibly with other endogenous AhR ligands also playing a role. The ability to expand MEPs with an AhR ligand also suggests that blood cell development may be affected by a variety of environmental ligands.

In addition to allowing for the exponential expansion of MEPs, our results indicate that AhR modulation is also involved in the further specification of both the erythroid and Mk lineages with AhR agonism permissive to the development of erythroblasts and antagonism or down regulation of AhR leading to Mk development. Although erythropoietin (EPO) and thrombopoietin (TPO) are the major drivers in RBC and platelet development, the data presented herein points to a cytokine-independent role for AhR in the development and specification of these lineages.

During the course of our studies we derived putative progenitors known to express markers of both the Mk and erythroid lineages. A particularly striking outcome of our experiments is the development of a simple protocol for the rapid and highly efficient derivation of putative MEPs which expand exponentially under AhR agonism. In addition to the ability to answer basic biological questions concerning hematopoietic development, a useful outcome for this work will be the utilization of this in vitro platform for the clinically relevant production of blood products. Blood transfusion is an indispensable cell therapy, and the safety and adequacy of the blood supply are national and international concerns. An iPSC-based system, such as the one described here in which sufficient numbers of cells can be produced, could allow for red blood cell and platelet transfusion without problems related to immunogenicity, contamination, or supply. Furthermore, the ability to produce both populations of cells from a single source, and the fact that both platelets and mature RBCs contain no nuclear genetic material decreases safety concerns with the use of iPSC-derived cells and paves the way for clinical translation.

In conclusion, we present the development of a novel, chemically defined, and feeder-free methodology for the production of iPSC-derived hematopoietic cells. This methodology allows for exponentially greater production of RBCs and platelets in comparison to existing methodologies and relies on the first of its kind definition of the role of the AhR receptor in nominal hematopoietic development using specialized ligands in hematopoietic progenitor cells.

Without wishing to be bound by theory, in part based on the data reported herein, we have defined distinct roles for AhR agonism and AhR antagonism in the differntiation of the platelet and erythrocyte lineages. A schematic is provided in FIG. 19. The right side of the figure shows the differentiation pathway from a hematopoietic stem cell (HSC) to a platelet or an erythrocyte (RBC). In the figure "AHR−" indicates antagonism of AhR and "AHR+" indicates agonism of AhR. In adult (blood tissue-specific) hepatopoietic stem cells (HSCs), AhR antagonism leads to increases in the number of cells capable of repopulation. Exposure of this population to AhR agonists leads to differentiation/specification and exponential increases in the numbers of common myeloid progenitor cells (CMPs) and megakaryocyte-erythroid progenitor cells (Meg-erythroid progenitors or MEPs). Continuous AhR agonism leads to RBC production, while conversely, AhR antagonism promotes platelet production at two points in the final specification of the MK: from the MEP to the MK and also from the maturing MK to the platelet.

An alternate way of making all of the cell types shown on the right portion of the figure involves the use of PSCs (pluripotent stem cells; e.g., iPSCs). Specification of iPSCs to the hematopoietic lineage is mediated by the formation of mesoderm and a hematopoietic/endothelial precursor known as the hemangioblast. AhR antagonism in the hemangioblast likely acts to maintain those cells in a multipotent state.

In FIG. 19, the process of differentiation from an iPSC to a platetlet or RBC is indicated as 20 days. Each stage is labeled with the approximate day on which such cells would be produced in an exemplary method. For example, iPSCs on day 0 (D0), HSCs on day 5 (D5), and MEPTs on day 10 (D10). The 20 day total time and the individual times indicted for the emergence of each cell type are exemplary only. Several factors in the methods disclosed herein may be varied in order to change the timeline.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of making a platelet, comprising culturing a megakaryocyte (Mk) in the presence of an aryl hydrocarbon receptor (AhR) antagonist, wherein the AhR antagonist is an agent that inhibits expression of an AhR-driven protein reporter in a HI G1 mouse hepatoma line in the presence of an AhR agonist, but does not induce a reporter response on its own.

2. The method of claim 1, wherein the AhR antagonist has the effect of increasing the rate of production of proplatelets in the culture.

3. A method of making a platelet, comprising culturing an Mk in the presence of an AhR antagonist, wherein the AhR antagonist is an agent that binds to the AhR.

4. The method of claim 3, wherein the AhR antagonist has the effect of increasing the rate of production of proplatelets in the culture.

* * * * *